US009173396B2

(12) United States Patent
Bretschneider et al.

(10) Patent No.: US 9,173,396 B2
(45) Date of Patent: Nov. 3, 2015

(54) HETEROCYCLIC COMPOUNDS AS PESTICIDES

(75) Inventors: Thomas Bretschneider, Lohmar (DE);
Adeline Köhler, Langefeld (DE);
Joachim Kluth, Langefeld (DE);
Martin Füβlein, Düsseldorf (DE); Peter Jeschke, Bergisch Gladbach (DE);
Reiner Fischer, Monheim (DE);
Friedrich August Mühlthau,
Kelkheim-Fischbach (DE); Olga Malsam, Rösrath (DE); Arnd Voerste,
Köln (DE); Klaus-Helmut Müller,
Düsseldorf (DE); Yoshitaka Sato,
Ibaraki (JP)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 13/878,193

(22) PCT Filed: Oct. 17, 2011

(86) PCT No.: PCT/EP2011/068129
§ 371 (c)(1),
(2), (4) Date: Jun. 18, 2013

(87) PCT Pub. No.: WO2012/052412
PCT Pub. Date: Apr. 26, 2012

(65) Prior Publication Data
US 2013/0261141 A1 Oct. 3, 2013

Related U.S. Application Data

(60) Provisional application No. 61/405,802, filed on Oct. 22, 2010.

(30) Foreign Application Priority Data

Oct. 22, 2010 (EP) .................................. 10188470

(51) Int. Cl.
| C07D 413/14 | (2006.01) |
| A01N 43/40 | (2006.01) |
| A01N 43/54 | (2006.01) |
| C07D 401/04 | (2006.01) |
| C07D 401/14 | (2006.01) |
| C07D 413/04 | (2006.01) |
| A01N 43/56 | (2006.01) |
| A01N 43/76 | (2006.01) |
| A01N 43/78 | (2006.01) |
| A01N 43/80 | (2006.01) |
| A01N 43/82 | (2006.01) |
| C07D 403/04 | (2006.01) |

(52) U.S. Cl.
CPC .............. *A01N 43/54* (2013.01); *A01N 43/40* (2013.01); *A01N 43/56* (2013.01); *A01N 43/76* (2013.01); *A01N 43/78* (2013.01); *A01N 43/80*
(2013.01); *A01N 43/82* (2013.01); *C07D 401/04* (2013.01); *C07D 401/14* (2013.01); *C07D 403/04* (2013.01); *C07D 413/04* (2013.01); *C07D 413/14* (2013.01)

(58) Field of Classification Search
CPC .............................. C07D 413/14; A01N 43/40
USPC .......................................... 544/333; 514/256
See application file for complete search history.

(56) References Cited

U.S. PATENT DOCUMENTS

| 2,847,417 | A | 8/1958 | William |
| 2,929,819 | A | 3/1960 | Erlenmeyer et al. |
| 3,542,798 | A | 11/1970 | Doebel et al. |
| 3,666,765 | A | 5/1972 | Berijckere et al. |
| 3,850,945 | A | 11/1974 | Edwards |
| 3,927,008 | A | 12/1975 | Bailey |
| 4,089,865 | A | 5/1978 | Edwards |
| 4,144,343 | A | 3/1979 | Baldwin et al. |
| 4,892,880 | A | 1/1990 | Kristiansen et al. |
| 4,987,146 | A | 1/1991 | Rohde et al. |
| 5,273,958 | A | 12/1993 | Kuhnt et al. |
| 5,536,720 | A | 7/1996 | Dekeyser et al. |
| 5,710,278 | A | 1/1998 | Goto et al. |
| 5,990,139 | A | 11/1999 | Yano et al. |
| 6,353,108 | B1 | 3/2002 | Bouchet et al. |
| 6,468,979 | B1 | 10/2002 | Pellacini et al. |
| 8,252,817 | B2 | 8/2012 | Flamme et al. |

(Continued)

FOREIGN PATENT DOCUMENTS

| DE | 1112076 B | 8/1961 |
| DE | 42938 | 11/1966 |

(Continued)

OTHER PUBLICATIONS

Dorwald, Side Reactions in Organic Synthesis, 2005, Wiley: VCH Weinheim Preface, pp. 1-15 & Chapter 8, pp. 279-308.*
International Search Report for PCT/EP2011/068129 Mailed Nov. 15, 2011.
Verrier, et al. "Palladium-Catalyzed Direct (Hetero)arylation of Ethyl Oxazole-4-carboxylate: An Efficient Access to (Hetero)aryloxazoles", J. Org. Chem. 2008, vol. 73, pp. 7383-7386.
Hemming "Product class 6:1,2,4-Oxadiazoles", Science of Synthesis, 2004, vol. 13, pp. 127-184.
Chen, et al. "Mild Conditions for Copper-Catalyzed N-Arylation of Imidazoles", Synthesis, 2010, vol. 9, pp. 1505-1511.
Schnürch, et al. "A Systematic Study of Suzuki-Miyaura Cross-Coupling Reactions on Thiazoleboronic Esters in the 4- and 5-Position", Synthesis, 2010, vol. 5, pp. 0837-0843.
Martin, et al. "Direct C-2 Arylation of Alkyl 4-Thiazolecarboxylates: New Insights in Synthesis of Heterocyclic Core of Thiopeptide Antibiotics", Organic Letters, 2008, vol. 10, No. 13, pp. 2909-2912.
Pu, et al. "An efficient copper-catalyzed N-arylation of pyridazinones with a structurally well-defined copper complex", Tetrahedron Letters, 2006, vol. 47, pp. 149-153.

(Continued)

*Primary Examiner* — Patricia L Morris
(74) *Attorney, Agent, or Firm* — Miles & Stockbridge P.C.

(57) ABSTRACT

The present application relates to novel heterocyclic compounds, to processes for preparation thereof and to the use thereof for controlling animal pests, which also include arthropods and especially insects.

3 Claims, No Drawings

(56) References Cited

U.S. PATENT DOCUMENTS

| | | |
|---|---|---|
| 2003/0055085 A1 | 3/2003 | Wagenen et al. |
| 2003/0125267 A1 | 7/2003 | Grant et al. |
| 2003/0220272 A1 | 11/2003 | Henninger et al. |
| 2004/0033970 A1 | 2/2004 | Clark et al. |
| 2004/0082611 A1 | 4/2004 | Kobayashi et al. |
| 2004/0171657 A1 | 9/2004 | Holzl et al. |
| 2005/0096362 A1 | 5/2005 | Kuo et al. |
| 2006/0287341 A1 | 12/2006 | Wu et al. |
| 2008/0171754 A1 | 7/2008 | Adams et al. |
| 2009/0076282 A1 | 3/2009 | Toriyabe et al. |
| 2009/0149517 A1 | 6/2009 | Bothe et al. |
| 2009/0247551 A1 | 10/2009 | Jeschke et al. |
| 2010/0035906 A1 | 2/2010 | Flamme et al. |
| 2010/0160323 A1 | 6/2010 | Bischoff et al. |
| 2010/0240705 A1 | 9/2010 | Jeschke et al. |
| 2011/0034404 A1 | 2/2011 | Goto et al. |
| 2011/0098287 A1 | 4/2011 | Bretschneider et al. |
| 2011/0160208 A1 | 6/2011 | Hirata et al. |
| 2011/0166143 A1 | 7/2011 | Bretschneider et al. |
| 2011/0190493 A1 | 8/2011 | Bretschneider et al. |
| 2011/0212949 A1 | 9/2011 | Bretschneider et al. |
| 2011/0306499 A1 | 12/2011 | Bretschneider et al. |
| 2012/0322772 A1 | 12/2012 | Flamme et al. |
| 2013/0123506 A1 | 5/2013 | Jeschke et al. |

FOREIGN PATENT DOCUMENTS

| | | |
|---|---|---|
| DE | 1965320 A1 | 7/1970 |
| DE | 2052536 | 5/1971 |
| DE | 2158615 A1 | 5/1973 |
| DE | 2252070 A1 | 5/1973 |
| DE | 3824658 A1 | 1/1990 |
| EP | 0122693 B1 | 7/1987 |
| EP | 0116515 B1 | 9/1988 |
| EP | 0296721 A2 | 12/1988 |
| EP | 0358595 A1 | 3/1990 |
| EP | 0296721 A3 | 4/1990 |
| EP | 0127371 B1 | 11/1990 |
| EP | 0511569 A1 | 11/1992 |
| EP | 0525879 A1 | 2/1993 |
| EP | 0539588 A1 | 5/1993 |
| EP | 0641797 A1 | 3/1995 |
| EP | 0692482 A2 | 1/1996 |
| EP | 1004592 A1 | 5/2000 |
| GB | 1417411 A | 12/1975 |
| JP | H-02142788 A | 5/1990 |
| JP | 07138258 A | 5/1995 |
| JP | 2002/504127 A | 2/2002 |
| JP | 2005223238 A | 8/2005 |
| JP | 2007145806 A | 6/2007 |
| JP | 2008-539180 A | 11/2008 |
| JP | 2010-507619 A | 3/2010 |
| JP | 2010-523654 A | 7/2010 |
| RU | 15525 U1 | 10/2000 |
| WO | 9304050 A1 | 3/1993 |
| WO | 9429300 A1 | 12/1994 |
| WO | 9701552 A1 | 1/1997 |
| WO | 9825912 A1 | 6/1998 |
| WO | 98/56785 A1 | 12/1998 |
| WO | 98/57969 A1 | 12/1998 |
| WO | 0002875 A1 | 1/2000 |
| WO | 0007446 A1 | 2/2000 |
| WO | 0009480 A1 | 2/2000 |
| WO | 0138332 A1 | 5/2001 |
| WO | 0145240 A1 | 6/2001 |
| WO | 01/56974 A2 | 8/2001 |
| WO | 02/090335 A1 | 11/2002 |
| WO | 03004509 A2 | 1/2003 |
| WO | 03022821 A1 | 3/2003 |
| WO | 03/027101 A1 | 4/2003 |
| WO | 03/027107 A1 | 4/2003 |
| WO | 03029210 A2 | 4/2003 |
| WO | 03077918 A1 | 9/2003 |
| WO | 2004013130 A1 | 2/2004 |
| WO | 2005005435 A1 | 1/2005 |
| WO | 2005035486 A1 | 4/2005 |
| WO | 2005047281 A1 | 5/2005 |
| WO | 2005061510 A1 | 7/2005 |
| WO | 2005066162 A1 | 7/2005 |
| WO | 2005085214 A1 | 9/2005 |
| WO | 2006/038100 A1 | 4/2006 |
| WO | 2006043635 A1 | 4/2006 |
| WO | 2006056433 A2 | 6/2006 |
| WO | 2006089633 A2 | 8/2006 |
| WO | 2006100288 A2 | 9/2006 |
| WO | 2006104141 A2 | 10/2006 |
| WO | 2006114213 A1 | 11/2006 |
| WO | 2006129714 A1 | 12/2006 |
| WO | 2006135604 A2 | 12/2006 |
| WO | 2007/043400 A1 | 4/2007 |
| WO | 2007043677 A1 | 4/2007 |
| WO | 2007057407 A2 | 5/2007 |
| WO | 2007067836 A2 | 6/2007 |
| WO | 2007115643 A1 | 10/2007 |
| WO | 2007115644 A1 | 10/2007 |
| WO | 2007115646 A1 | 10/2007 |
| WO | 2007149134 A1 | 12/2007 |
| WO | 2008004117 A1 | 1/2008 |
| WO | 2008028903 A2 | 3/2008 |
| WO | 2008049864 A1 | 5/2008 |
| WO | 2008054702 A1 | 5/2008 |
| WO | 2008067911 A1 | 6/2008 |
| WO | 2008104503 A1 | 9/2008 |
| WO | 2008127464 A1 | 10/2008 |
| WO | 2009/032861 A1 | 3/2009 |
| WO | 2009028727 A1 | 3/2009 |
| WO | 2009/051705 A1 | 4/2009 |
| WO | 2009105500 A1 | 8/2009 |
| WO | 2009112845 A1 | 9/2009 |
| WO | 2009127669 A1 | 10/2009 |
| WO | 2009129036 A1 | 10/2009 |
| WO | 2009/146343 A1 | 12/2009 |
| WO | 2009148452 A1 | 12/2009 |
| WO | 2009149135 A1 | 12/2009 |
| WO | 2009149858 A1 | 12/2009 |
| WO | 2010005572 A2 | 1/2010 |
| WO | 2010006713 A1 | 1/2010 |
| WO | 2010006713 A2 | 1/2010 |
| WO | 2010018113 A1 | 2/2010 |
| WO | 2010/026134 A1 | 3/2010 |
| WO | 2010025553 A1 | 3/2010 |
| WO | 2010074747 A1 | 7/2010 |
| WO | 2010074751 A1 | 7/2010 |
| WO | 2010075270 A1 | 7/2010 |
| WO | 2011045224 A1 | 4/2011 |

OTHER PUBLICATIONS

Kondo, et al. "Synthesis and Reactions of 5-(Tributylstannyl)/Soxazoles", Tetrahedron Letters,1989, vol. 30, No. 32, pp. 4249-4250.

Hargreaves, et al. "The synthesis of substituted pyridylpyrimidine fungicides using palladium-catalysed cross-coupling reactions", Tetrahedron Letters, 2000, vol. 41, pp. 1653-1656.

Kotha, et al. "Recent applications of the Suzuki-Miyaura cross-coupling reaction in organic synthesis", Tetrahedron, 2002, vol. 58, pp. 9633-9695.

Zhang, et al. "Pyridine-Substituted Hydroxythiophenes. IV. Preparation of 3- and 4-(2-, 3- and 4-Pyridyl)-2-hydroxythiophenes", J. Heterocyclic Chem., 1995, vol. 32, pp. 435-444.

Kost, et al. "Synthesis and Some Conversions of Etitynylcarbinols of the Pyridine Series", Zhurnal Ohshchei Khimii, vol. 32, No. 8, pp. 2606-2612, Aug. 1962.

De Meijere, et al. "Metal-Catalyzed Cross-Coupling Reactions 2nd ed, Wiley-VCH, Weinheim", 2004.

Bodansky, et al. "Houben-Weyl, Methods of Organic Chemistry, Peptide Synthesis2nd ed", 1976.

Gross, et al. "The Peptided: Analysis", 1979.

Greene, et al. "Protective Groups in Organic Synthesis", John Wiley & Sons, Inc., 1999, 494ff.

(56) References Cited

OTHER PUBLICATIONS

Pomel, et al. "Furan-2-ylmethylene Thiazolidinediones as Novel, Potent, and Selective Inhibitors of Phosphoinositide 3-Kinase", J. Med. Chem. 2006, vol. 49, pp. 3857 3871.
Dowlatshahi "1,4,5,6-Tetrahydro-1-Phenylpyridazin-3(2H)-One, a Homologue of Phenidone", Synthetic Communications,1987, vol. 17, pp. 1253-1259.
Grimes, et al. "Copper(II)-Catalyzed Conversion of Aryl/Heteroaryl Boronic Acids, Boronates, and Trifluoroborates into the Corresponding Azides: Substrate Scope and Limitations", Synthesis, 2010, vol. 9, pp. 1441-1448.
European Search Report dated Mar. 3, 2011.
Ikeda, et al. "Synthesis and Cytoprotective Antiulcer Activity of 2- or 4-(1H-Pyrazol-1-YL) Pyrimidine Derivatives Related to Mepirizole and Dulcerozine", Chem. Pharm. Bull. vol. 44(9), 1996, p. 1700-1706.
Kudo, et al. "A Versatile Method for Suzuki Cross-Coupling Reactions of Nitrogen Heterocycles", Angew. Chem. 2006, vol. 118, p. 1304-1306.
Araki, at al. "Synthesis and Reaction of the First Oxazol-4-Ylboronates: Useful Reagents for the Preparation of the Oxazole-Containing Biaryl Compaunds", Synlett 2006, vol. 4, pp. 0555-0558.
Bookser "2-Benzyloxymethyl-5-(Tributylstannyl)Tetrazole. A Reagent for the Preparation of 5-Aryl-and 5-Heteroaryl-1H-Tetrazoles Via the Stille Reaction", Terahedron Letters, vol. 41 (2000), pp. 2805-2809.
El-Badawi, et al. "Synthesis and Reactivity of Some Pyridyl Isoxazol-5-Ones", Bulgarian Chemical Communications, vol. 40, Nov. 1, 2008, pp. 70-77.
Miyaura, et al. "Palladium-Catalyzed Cross-Coupling Reactions of Organoboron Compounds", Chem. Rev. 1995, vol. 95, pp. 2457-2483.
Fisera, et al. "Synthesis and Mass Spectra of Some Pyridylfuran Derivatives. The Determination of 6m Constants of 2-X-5-Furyl Substituents", Collection Czechoslov. Chem. Commun. vol. 42, 1977, pp. 105-111.
Alberico, et al. "Aryl-Aryl Bond Formation by Transition-Metal-Catalyzed Direct Arylation", Chem. Rev. 2007, vol. 107, pp. 174-238.
Boger, et al. "Discovery of a Potent, Selective, and Efficacious Class of Reversible a-Ketoheterocycle Inhibitors of Fatty Acid Amide Hydrolase Effective as Analgesics", J. Med. Chem. 2005, 48, pp. 1849-1856.
Gauthier, et al. "Synthesis of 5-Pyridyl-2-furaldehydes via Palladium-Catalyzed Cross-Coupling with Triorganozincates", Organic Letters, vol. 4, No. 3, 2002, pp. 375-378.
Flegeau, et al. "Regioselective Palladium Cross-Coupling of 2,4-Dihalooxazoles: Convergent Synthesis of Trisoxazoles", J. Org. Chem. 2008, vol. 73, pp. 33033-3306.
Gebauer, et al. "Total Synthesis of Cystothiazole A by Microwave-Assisted Olefin Cross-Metathesis", Eur. J. Org. Chem. 2008, vol. 16, pp. 2701-2704.
Cristau, et al. "Mild Conditions for Copper-Catalysed N-Arylation of Pyrazoles", Eur. J. Org. Chem. 2004, vol. 4, pp. 695-709.
Rosen, et al. "The Reaction of Carboxylic Acid Hydrazides with Formaldehyde", J. Heterocyclic Chem., 1975, vol. 12, pp. 619-622.
McGlacken, et al. "Recent advances in aryl-aryl bond formation by direct arylation", Chem. Soc. Rev., 2009, vol. 38, pp. 2447-2464.
Humphrey, et al. "A Novel Synthesis of 3-Bromo-1,2,4-oxadiazoles ", J. Heterocyclic Chem., 1989, vol. 26, pp. 23-24.
Brunner, et al. "Neue optisch aktive Pyrazolderivate fiir die enantioselektive Katalyse", Chem. Ber. 1992, vol. 125, pp. 701-709.
Wynberg, et al. "The Synthesis, Structure Proof, and Spectral Properties of the Six Pyridylthiophenes", J. Org. Chem, vol. 34, No. 10, Oct. 1969, pp. 3175-3178.
Wang, et al. "Microwave-assisted cross-coupling of 3-chloro-2-pyrazolines and 3-chloro-1-phenyl-1,4,5,6-tetrahydropyridazine with aryl boronic acids", Tetrahedron Letters, 2005, vol. 46, pp. 2631-2634.

Dadkhah, et al. "IJber Pyridyloxazole, eine neue Klasse Dipyridylahnlicher Verbindungen", Helv. Chim. Acta, 1962, vol. 42, 375-381.
Belgodere, et al. "Studies on Isomeric Pyridylisoxazoles",Heterocycles, vol. 20, No. 3, 1983, pp. 501-504.
Seregin, et al. "Direct transition metal-catalyzed functionalization of heteroaromatic compounds", Chemical Society Reviews, 2007, vol. 36, pp. 1173-1193.
Yoburn, et al. "Chemoselective Arylamidine Cyclizations: Mild Formation of 2-Arylimidazole-4-carboxylic Acids", Organic Letters, 2005, vol. 7, No. 17, pp. 3801-3803.
Naflsa, et al. "Syntheses and Characterization of Some Carbobutoxythio Compounds and Substituted Oxathiazolones", Journal of chemical and engineering data, vol. 30, 1985, pp. 507-509.
Khan, et al. "Syntheses of Heterocyclic Compounds. Part IL, N-Arylazoles by Ullmann Condensation", J. Chem.Soc., 1970, vol. 1, pp. 85-91.
Evans, et al. "Thiadiazoles and Dihydrothiadiazoles. Part 5. Synthesis of 2,3-Dihydro-1,3,4-thiadiazoles by Reaction of Aldehydes or Ketones with Thioaroylhydrazines", J. Chem. Soc. vol. 8,1986, pp. 1499-1505.
Goerdeler, et al. "Darstellung und Eigensehaften des 1.2.4- und des 1.3.4-Thiodiazolsu", Chem Ber., 1956, vol. 89, pp. 1534-1543.
Lin, et al. "New Synthesis of 1,2,4-Triazoles and 1,2,4-Oxadiazoles", J. Org. Chem., vol. 44, No. 23, 1979, pp. 4160-4164.
Irie, et al. "Photochromism of dithiazolylethenes having pyridyl and N-methylpyridinium groups", J. Phys. Org. Chem., 2007; vol. 20, pp. 894-899.
Wittenbrook, et al. "The Chemistry of N-Cyanodithioimidoearbonic Acid. II. Synthesis of 3-Halo-1,2,4-thiadiazoles", J. Org. Chem., 1973 vol. 38, No. 3, pp. 465-471.
Nicolaou,et al. "Synthesis and Biological Evaluation of 12,13-Cyclopropyl and 12,13-Cyclobutyl Epothilones", Chembiochem, 2001, vol. 2, pp. 69-75.
Hodgetts, et al. "Ethyl 2-Chlorooxazole-4-carboxylate: A Versatile Intermediate for the Synthesis of Substituted Oxazoles", Organic Letters, 2002, vol. 4, No. 17, pp. 2905-2907.
Vallin, et al. "Efficient Chemoenzymatic Dynamic Kinetic Resolution of 1-Heteroaryl Ethanols", J. Org. Chem., 2009, vol. 74, pp. 9328-9336.
Ismail, et al. "Synthesis and Antiprotozoal Activity of Aza-Analogues of Furamidine", J. Med. Chem., 2003, vol. 46, pp. 4761-4769.
Gezginci, et al. "Antimycobacterial Activity of Substituted Isosteres of Pyridine- and Pyrazinecarboxylic Acids. 2.1", J. Med. Chem., 2001, vol. 44, pp. 1560-1563.
Curtis, et al. "A convenient and rapid approach for the synthesis of 1-benzyl-3-heterocyclic pyrazoles", Tetrahedron Letters, 2009, vol. 50, pp. 5479-5481.
Giudice, et al. "Synthesis of 1-Methyl-5-(pyrazol-3-and-5-yl-and 1,2,4-triazol-3-and 5-y1)-1,2,3,6-tetrahydropyridine Derivatives and Their Evaluation as Muscarinic Receptor Ligands", Arch. Pharm. Pharm. Med. Chem. 2003, vol. 336, pp. 143-154.
Burger, et al. "Synthesis and Antibacterial Activity of Novel C12 Vinyl Ketolides", J. Med. Chem. 2006, vol. 49, pp. 1730-1743.
Sorokin "Copper (I) Catalyzed N-Arylation of Azoles, the Recent Developments", Mini-Reviews in Organic Chemistry, 2008, vol. 5, pp. 323-330.
Kim, et al. "Highly Efficient and Reusable Copper-Catalyzed N-Arylation of Nitrogen-Containing Heterocycles with Aryl Halides", Molecules, 2009, vol. 14, pp. 5169-5178.
Langille, et al. "Sonogashira Coupling of Functionalized Trifloyl Oxazoles and Thiazoles with Terminal Alkynes: Synthesis of Disubstituted Heterocycles", Organic Letters, 2002, vol. 4, No. 15, pp. 2485-2488.
Haginoya, et al. "Design, synthesis, and biological activity of non-amidine factor Xa inhibitors containing pyridine N-oxide and 2-carbamoylthiazole units", Bioorg. Med. Chem., 2004, vol. 12, pp. 5579-5586.
Leonard,et al. "Synthesis of Cytosine Radiolysis Products: cis- and trans-1-Carbamoy1-4,5-dihydroxyimidazolidin-2-one", Journal of the American Chemical Society, 1976, vol. 98, pp. 8218-8221.
Primas, et al. "Synthesis of 2-TIPS-oxazol-5-ylboronic acid pinacol ester: efficient route to 5-(het)aryloxazoles via Suzuki cross-coupling reaction", Tetrahedron, 2009, vol. 65, pp. 6348-6353.

(56) References Cited

OTHER PUBLICATIONS

Hacser, et al. "The Acetoacetic Ester Condensation and Certain Related Reactions", J. Art. Chem. Soc., vol. 1, 1942, pp. 266-302.

Thomas, et al. "Dark-Field Oxidative Addition-Based Chemosensing: New Bis-cyclometalated Pt(II) Complexes and Phosphorescent Detection of Cyanogen Halides", J. Am. Chem. Soc., 2006, vol. 128, pp. 16641-16648.

Huisgen, et al., Angew. Chem., 1962, vol. 74, p. 30.

De Graaff, et al. "Synthesis of the Racemic Mixtures of the Diasiereomeric Nicotine-2-Carboxylic Acids", Rec. Travaux Chim. Des Pay-Bas, 1964, vol. 83, pp. 910-918.

Zwart, et al. "Chemical Behaviour of 3-Aminopyridine and of 3,5-Diaminopyridine. Syntheses of (3-Pyridyl)-Pyrazolones", Rec. Travaux Chim. Des Pay-Bas et de la Belgique, 1995, vol. 74, pp. 1062-1069.

Watterson, et al. "Small Molecule Antagonist of Leukocyte Function Associated Antigen-1 (LFA-1): Structure—Activity Relationships Leading to the Identification of 6-((5S,9R)-9-(4-Cyanophenyl)-3-(3,5-dichlorophenyl)-1-methyl-2,4-dioxo-1,3,7-triazaspiro[4.4]nonan-7-yl)nicotinic Acid (BMS-688521)†", J. Med. Chem., 2010, vol. 53, pp. 3814-3830.

Branowska, Danuta et al., "Synthesis and antiprotozoal activity of 2,5-bis [amidinoaryl] thiazoles", Bioorganic & Medicinal Chemistry, vol. 18(10), p. 3551-3558, Mar. 2010.

Santos et al., "Unconventional oxazole formation from isocyanides", Chemical Communications (Cambridge, United Kingdom), vol. 26, p. 3907-3909, 2009.

Min, Jaeki; et al. Combinatorial Dapoxyl Dye Library and its Application to Site Selective Probe for Human Serum Albumin, Journal of Combinatorial Chemistry, vol. 9(6), pp. 1079-1083, Supporting information, 2007.

Kerr, V. N. "Liquid scintillators. VIII. The effect of the dialkylamino group", Journal of Organic Chemistry, vol. 24, p. 1864-1866, 1959.

\* cited by examiner

HETEROCYCLIC COMPOUNDS AS PESTICIDES

CROSS REFERENCE TO RELATED APPLICATIONS

This application is a §371 National Stage Application of PCT/EP2011/068129, filed Oct. 17, 2011, which claims priority to European Application No. 10188470.8, filed Oct. 22, 2010, and U.S. Provisional Application No. 61/405,802 filed Oct. 22, 2010.

BACKGROUND OF THE INVENTION

1. Field of the Invention

The present invention relates to novel heterocyclic compounds, to processes for preparation thereof and to the use thereof for controlling animal pests, which also include arthropods and especially insects.

2. Description of Related Art

WO 2008/028903 A2, WO 2003/077918 A1 and WO 2003/029210 A2 disclose heterocyclic compounds for which pharmaceutical applications are described.

Further heterocycles which may be used in plant protection are described in WO 2009/149858, WO 2010/006713, WO 2011/045240 and WO 2011/045224.

Modern crop protection compositions have to meet many demands, for example in relation to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons alone, the search for novel crop protection agents cannot be considered as having been concluded, and there is a constant need for novel compounds having properties which, compared to the known compounds, are improved at least in respect of individual aspects.

SUMMARY

It was an object of the present invention to provide compounds which widen the spectrum of the pesticides under various aspects.

This object, and further objects which are not stated explicitly but can be discerned or derived from the connections discussed herein, are achieved by novel compounds of the formula (I)

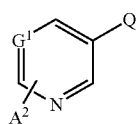

(I)

in which
$G^1$ represents N or C-$A^1$,
$A^1$ represents hydrogen, halogen, cyano, nitro, alkyl, haloalkyl, alkoxy or optionally substituted cycloalkyl or cycloalkenyl, where one or more ring members in the cycloalkyl ring and in the cycloalkenyl ring may in each case be replaced by a heteroatom,
$A^2$ represents hydrogen, halogen, cyano, nitro, alkyl, haloalkyl, alkoxy or optionally substituted cycloalkyl or cycloalkenyl, where one or more ring members in the cycloalkyl ring and in the cycloalkenyl ring may in each case be replaced by a heteroatom, Q represents one of the radicals (Q-1) to (Q-64)

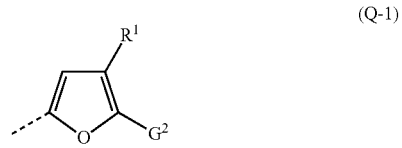

(Q-12) 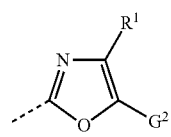
(Q-13) 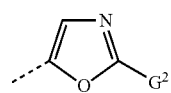
(Q-14) 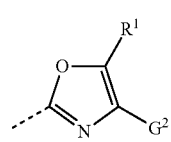
(Q-15) 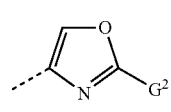
(Q-16) 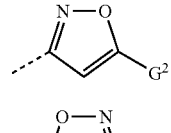
(Q-17) 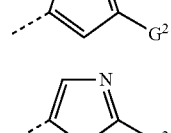
(Q-18) 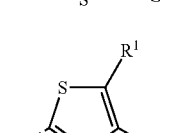
(Q-19) 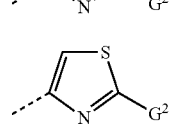
(Q-20) 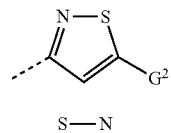
(Q-21) 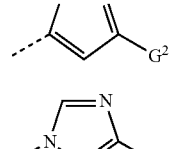
(Q-22) 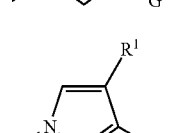
(Q-23) 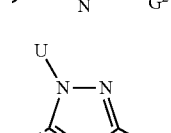
(Q-24) 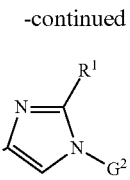
(Q-25) 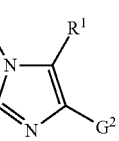
(Q-26) 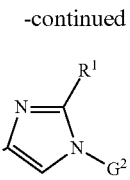
(Q-27) 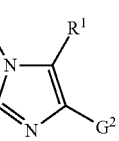
(Q-28) 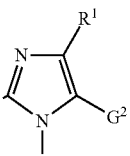
(Q-29) 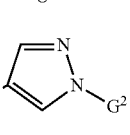
(Q-30) 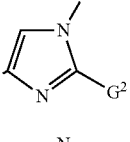
(Q-31) 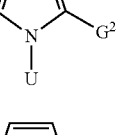
(Q-32) 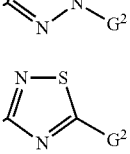
(Q-33) 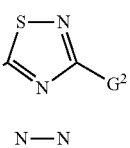
(Q-34) 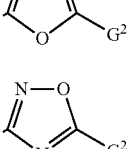
(Q-35) 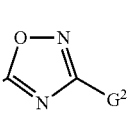
(Q-36) 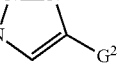
(Q-37)
(Q-38)

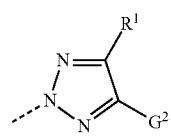
(Q-39)
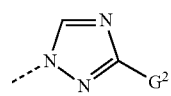
(Q-40)
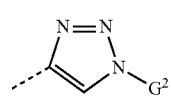
(Q-41)
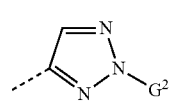
(Q-42)
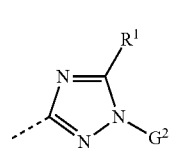
(Q-43)
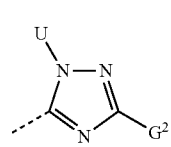
(Q-44)
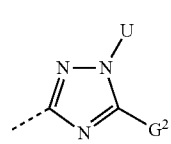
(Q-45)
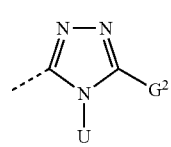
(Q-46)
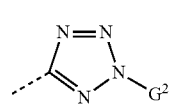
(Q-47)
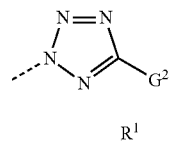
(Q-48)
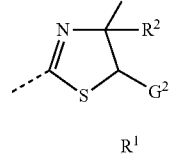
(Q-49)
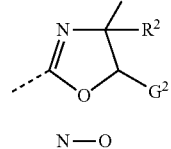
(Q-50)
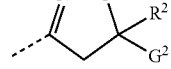
(Q-51)
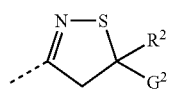
(Q-52)
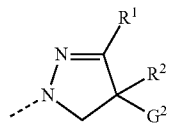
(Q-53)
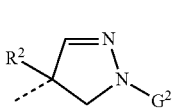
(Q-54)
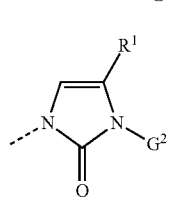
(Q-55)
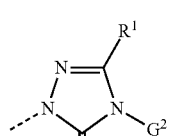
(Q-56)
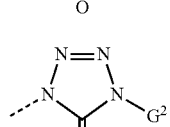
(Q-57)
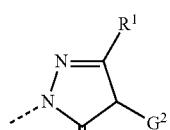
(Q-58)
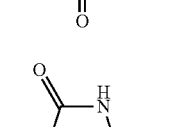
(Q-59)
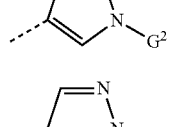
(Q-60)
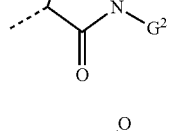
(Q-61)
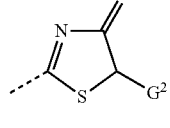
(Q-62)
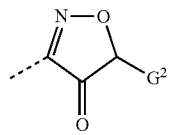

-continued

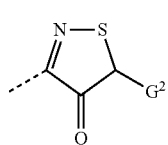
(Q-63)

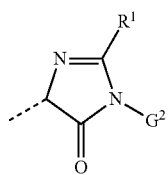
(Q-64)

in which
U represents hydrogen, alkyl, haloalkyl or cycloalkyl,
$R^1$ represents hydrogen, halogen, cyano, hydroxyl, alkyl, haloalkyl, alkoxy or cycloalkyl,
$R^2$ represents hydrogen, halogen, cyano, hydroxyl, alkyl, haloalkyl, alkoxy, alkoxycarbonyl or cycloalkyl,
and where in the radicals Q-1, Q-2, Q-3, Q-4, Q-5, Q-6, Q-7, Q-8, Q-9, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-33, Q-34, Q-35, Q-36, Q-37, Q-38, Q-39, Q-40, Q-44, Q-45, Q-46, Q-48, Q-49, Q-50, Q-51, Q-52, Q-53, Q-58, Q-61, Q-62 and Q-63
$G^2$ represents a radical from the group consisting of ($G^2$-1) to ($G^2$-30)
and in the radicals Q-10, Q-26, Q-29, Q-32, Q-41, Q-42, Q-43, Q-47, Q-54, Q-55, Q-56, Q-57, Q-59, Q-60 and Q-64
$G^2$ represents a radical from the group consisting of $G^2$-2, $G^2$-3, $G^2$-4, $G^2$-5, $G^2$-6, $G^2$-7, $G^2$-9, $G^2$-10, $G^2$-11, $G^2$-12, $G^2$-13, $G^2$-14, $G^2$-15, $G^2$-16, $G^2$-17, $G^2$-18, $G^2$-19, $G^2$-20, $G^2$-21, $G^2$-22, $G^2$-23, $G^2$-24, $G^2$-25, $G^2$-26, $G^2$-27, $G^2$-29 and $G^2$-30,
where the radicals ($G^2$-1) to ($G^2$-30) have the following meanings

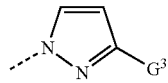
($G^2$-1)

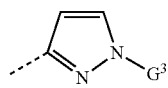
($G^2$-2)

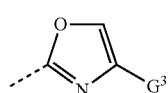
($G^2$-3)

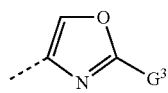
($G^2$-4)

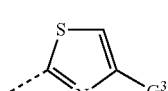
($G^2$-5)

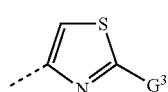
($G^2$-6)

-continued

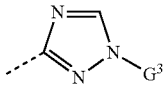
($G^2$-7)

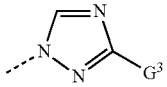
($G^2$-8)

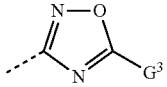
($G^2$-9)

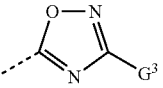
($G^2$-10)

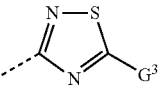
($G^2$-11)

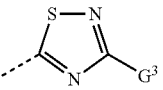
($G^2$-12)

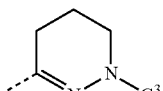
($G^2$-13)

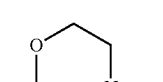
($G^2$-14)

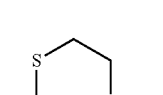
($G^2$-15)

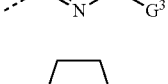
($G^2$-16)

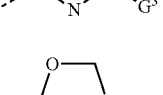
($G^2$-17)

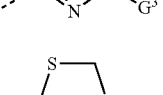
($G^2$-18)

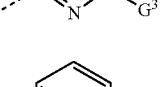
($G^2$-19)

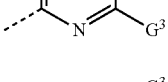
($G^2$-20)

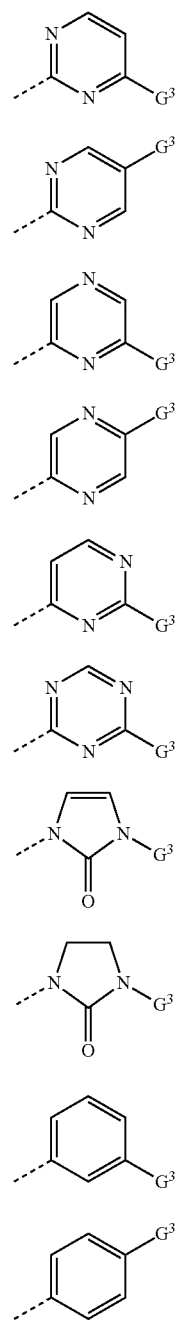

where the broken line marks the bond to the heterocycle in (Q-1) to (Q-64),

G³ represents a radical from the group consisting of halogen, nitro, amino, cyano, alkylamino, haloalkylamino, dialkylamino, alkyl, haloalkyl, optionally substituted saturated or unsaturated cycloalkyl which is optionally interrupted by one or more heteroatoms, cycloalkylalkyl, alkoxy, haloalkoxy, alkoxyalkyl, halogenated alkoxyalkyl, bis(alkoxy)alkyl, bis(haloalkoxy)alkyl, alkoxy(alkylsulfanyl)alkyl, alkoxy(alkylsulfinyl)alkyl, alkoxy(alkylsulfonyl)alkyl, bis(alkylsulfanyl)alkyl, bis(haloalkylsulfanyl)alkyl, bis(hydroxyalkylsulfanyl)alkyl, alkoxycarbonyl, alkoxycarbonylalkyl, alpha-hydroxyiminoalkoxycarbonylalkyl, alpha-alkoxyiminoalkoxycarbonylalkyl, C(X)NR³R⁴ (in which X represents oxygen, sulfur, NR⁵ or NOH, R³ represents hydrogen or alkyl and R⁴ and R⁵ independently of one another represent a radical from the group consisting of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, aryl, arylalkyl and hetarylalkyl or R³ and R⁴ together with the nitrogen atom to which they are attached form a ring which may contain one or more further heteroatoms from the group consisting of nitrogen, oxygen and sulfur or R³ and R⁵ together with the nitrogen atoms to which they are attached form a ring), NR⁶R⁷ (in which R⁶ represents hydrogen or alkyl and R⁷ represents a radical from the group consisting of hydrogen, alkyl, haloalkyl, cyanoalkyl, alkynyl, cycloalkyl, cycloalkylalkyl, alkoxy, haloalkoxy, alkoxyalkyl, alkoxycarbonyl, alkoxycarbonylalkyl, alkylthioalkyl, aryl, arylalkyl and hetarylalkyl or R⁶ and R⁷ together with the nitrogen atom to which they are attached form a ring which may contain one or more further heteroatoms from the group consisting of nitrogen, oxygen and sulfur) alkylthio, alkylsulfinyl, alkylsulfonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by alkyl, haloalkyl, alkoxy and alkoxyalkyl), phenyl (which for its part may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may be substituted by halogen and alkyl), or G³ represents a radical from the group consisting of (B-1) to (B-9)

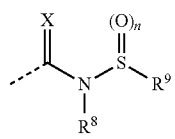

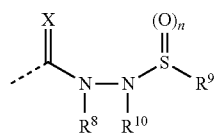

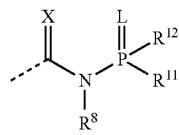

-continued

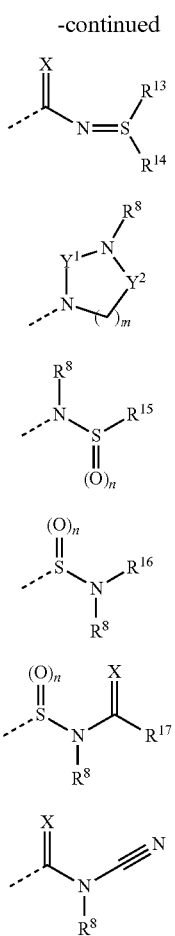

where the broken line marks the bond to the adjacent ring in the radicals (G²-1) to (G²-30)

X represents oxygen or sulfur, n represents 1 or 2, $R^8$ represents a radical from the group of hydrogen, alkyl, haloalkyl, cyanoalkyl, alkoxy, haloalkoxy, alkenyl, alkoxyalkyl, in each case optionally halogen-substituted alkylcarbonyl and alkylsulfonyl, optionally halogen-substituted alkoxycarbonyl, optionally halogen-, alkyl-, alkoxy-, haloalkyl- and cyano-substituted cycloalkylcarbonyl, or a cation, for example a mono- or divalent metal ion or an optionally alkyl- or arylalkyl-substituted ammonium ion, $R^{15}$ and $R^9$ independently of one another represent a radical from the group consisting of in each case optionally substituted alkyl, alkenyl and alkynyl, in each case optionally substituted cycloalkyl, cycloalkylalkyl and cycloalkenyl, in which the rings may contain at least one heteroatom from the group consisting of sulfur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{15}$ may also, together with the N—S(O)$_n$ group to which they are attached, form a saturated or unsaturated and optionally substituted 4- to 8-membered ring which may contain one or more further heteroatoms from the group consisting of sulfur, oxygen (where oxygen atoms must not be directly adjacent to one another) and nitrogen and/or at least one carbonyl group, $R^{17}$ represents a radical from the group consisting of in each case optionally substituted alkyl, alkoxy, alkenyl and alkynyl, in each case optionally substituted cycloalkyl, cycloalkylalkyl and cycloalkenyl, in which the rings may contain at least one heteroatom from the group consisting of sulfur, oxygen (where oxygen atoms must not be directly adjacent to one another) and nitrogen, in each case optionally substituted aryl, heteroaryl, arylalkyl and heteroarylalkyl and an optionally substituted amino group, $R^{16}$ represents a radical from the group consisting of hydrogen, in each case optionally substituted alkyl, alkoxy, alkenyl and alkynyl, in each case optionally substituted cycloalkyl, cycloalkylalkyl and cycloalkenyl, in which the rings may contain at least one heteroatom from the group consisting of sulfur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{17}$ may also, together with the N—C(X) group to which they are attached, form a saturated or unsaturated and optionally substituted 4- to 8-membered ring which may contain one or more further heteroatoms from the group consisting of sulfur, oxygen (where oxygen atoms must not be directly adjacent to one another) and nitrogen and/or at least one carbonyl group, $R^{10}$ represents hydrogen or alkyl, $R^8$ and $R^{10}$ may also represent, together with the nitrogen atoms to which they are attached, a saturated or unsaturated and optionally substituted 4- to 8-membered ring which may contain at least one further heteroatom from the group consisting of sulfur, oxygen (where oxygen atoms must not be directly adjacent to one another) and nitrogen and/or at least one carbonyl group, $R^8$ and $R^9$ in the radical (B-1) may also form, together with the N—S(O)$_n$ group to which they are attached, a saturated or unsaturated and optionally substituted 4- to 8-membered ring which may contain one or more further heteroatoms from the group of sulfur, oxygen (where oxygen atoms must not be directly adjacent to one another) and nitrogen and/or at least one carbonyl group, $R^9$ and $R^{10}$ may also form, together with the N—S(O)$_n$ group to which they are attached, a saturated or unsaturated and optionally substituted 4- to 8-membered ring which may contain one or more further heteroatoms from the group of sulfur, oxygen (where oxygen atoms must not be directly adjacent to one another) and nitrogen and/or at least one carbonyl group, $R^8$ and $R^{16}$ may also form, together with the nitrogen atom to which they are attached, a saturated or unsaturated and optionally substituted 4- to 8-membered ring which may contain one or more further heteroatoms from the group of sulfur, oxygen (where oxygen atoms must not be directly adjacent to one another) and nitrogen and/or at least one carbonyl group, L represents oxygen or sulfur, $R^{11}$ and $R^{12}$ independently of one another represent an in each case optionally substituted radical from the group consisting of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^{11}$ and $R^{12}$ may also form, together with the phosphorus atom to which they are attached, a saturated or unsaturated and optionally substituted 5- to 7-membered ring which may contain one or two heteroatoms from the group of oxygen (where oxygen atoms must not be directly adjacent to one another) and sulfur, and $R^{13}$ and $R^{14}$ independently of one another represent an in each case optionally substituted radical from the group consisting of alkyl, alkenyl, alkynyl, phenyl and phenylalkyl, $Y^1$ and $Y^2$ independently of one another represent C=O or $S(O)_2$ and m represents 1, 2, 3 or 4, and also salts, tautomeric and/or isomeric forms and N-oxides of the compounds of the formula (I).

DETAILED DESCRIPTION OF A PREFERRED EMBODIMENT

Preferred substituents or ranges for the radicals mentioned in the compounds of the formula (I) are illustrated below.

$G^1$ represents N or $C-A^1$.

$A^1$ represents hydrogen, halogen, cyano, nitro, $C_1$-$C_6$-alkyl, $C_1$-$C_6$-haloalkyl, $C_1$-$C_6$-alkoxy or in each case optionally halogen-, $C_1$-$C_6$-alkyl-, $C_1$-$C_6$-haloalkyl-, $C_1$-$C_6$-alkoxy-, $C_1$-$C_6$-haloalkoxy-substituted $C_3$-$C_6$-cycloalkyl or $C_3$-$C_6$-cycloalkenyl in which one or two ring members may in each case be replaced by a heteroatom from the group consisting of nitrogen, oxygen and sulfur, where two oxygen atoms must not be directly adjacent to one another.

$A^2$ represents hydrogen, halogen, cyano, nitro, $C_1$-$C_6$-alkyl, $C_1$-$C_6$-haloalkyl, $C_1$-$C_6$-alkoxy or in each case optionally halogen-, $C_1$-$C_6$-alkyl-, $C_1$-$C_6$-haloalkyl-, $C_1$-$C_6$-alkoxy-, $C_1$-$C_6$-haloalkoxy-substituted $C_3$-$C_6$-cycloalkyl or $C_3$-$C_6$-cycloalkenyl in which one or more ring members may in each case be replaced by a heteroatom from the group consisting of nitrogen, oxygen and sulfur, where two oxygen atoms must not be directly adjacent to one another.

Q represents one of the radicals (Q-1) to (Q-64)

(Q-1)
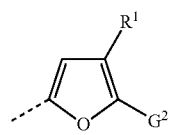

(Q-2)
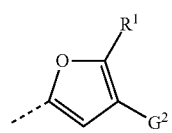

(Q-3)
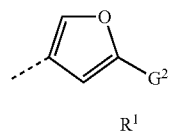

(Q-4)
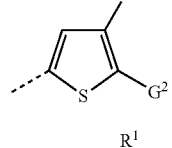

(Q-5)
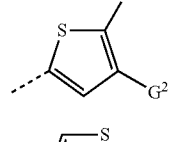

(Q-6)
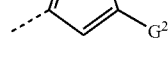

(Q-7)
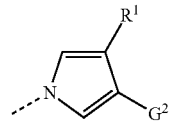

(Q-8)
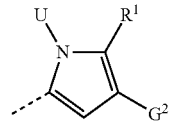

(Q-9)
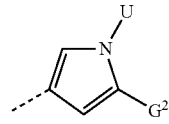

(Q-10)
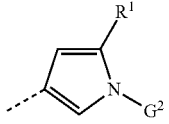

(Q-11)
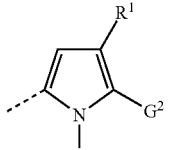

(Q-12)
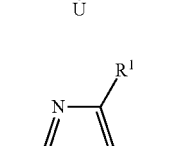

(Q-13)
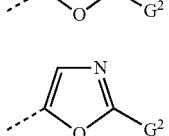

(Q-14)
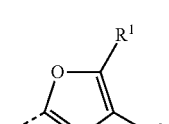

(Q-15)
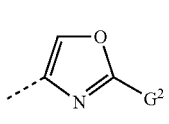

(Q-16)
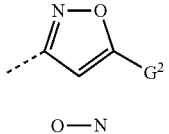

(Q-17)

(Q-18)
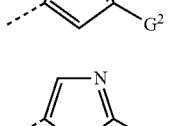

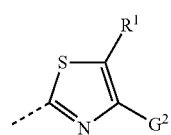
(Q-19)
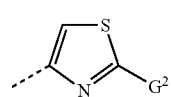
(Q-20)
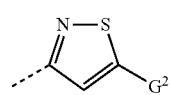
(Q-21)
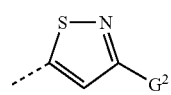
(Q-22)
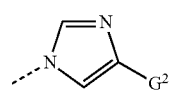
(Q-23)
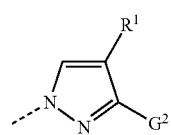
(Q-24)
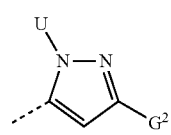
(Q-25)
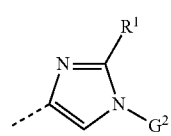
(Q-26)
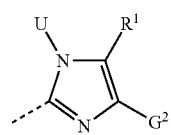
(Q-27)
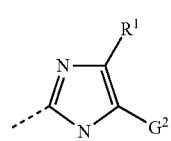
(Q-28)
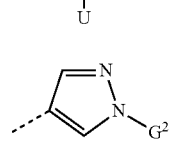
(Q-29)
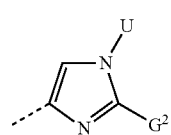
(Q-30)
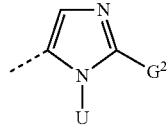
(Q-31)
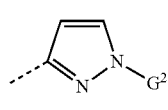
(Q-32)
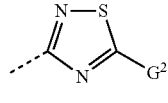
(Q-33)
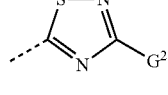
(Q-34)
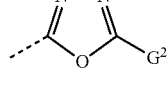
(Q-35)
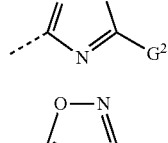
(Q-36)
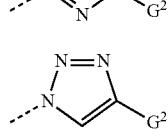
(Q-37)
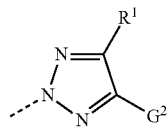
(Q-38)
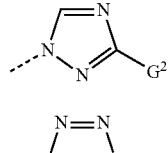
(Q-39)
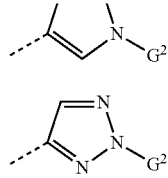
(Q-40)
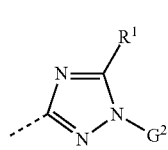
(Q-41)
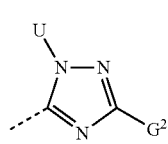
(Q-42)
(Q-43)
(Q-44)

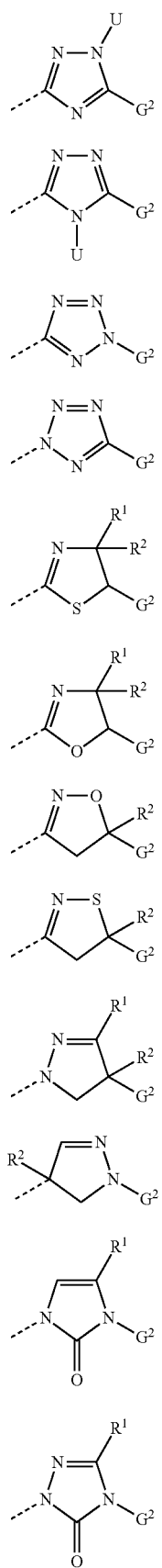
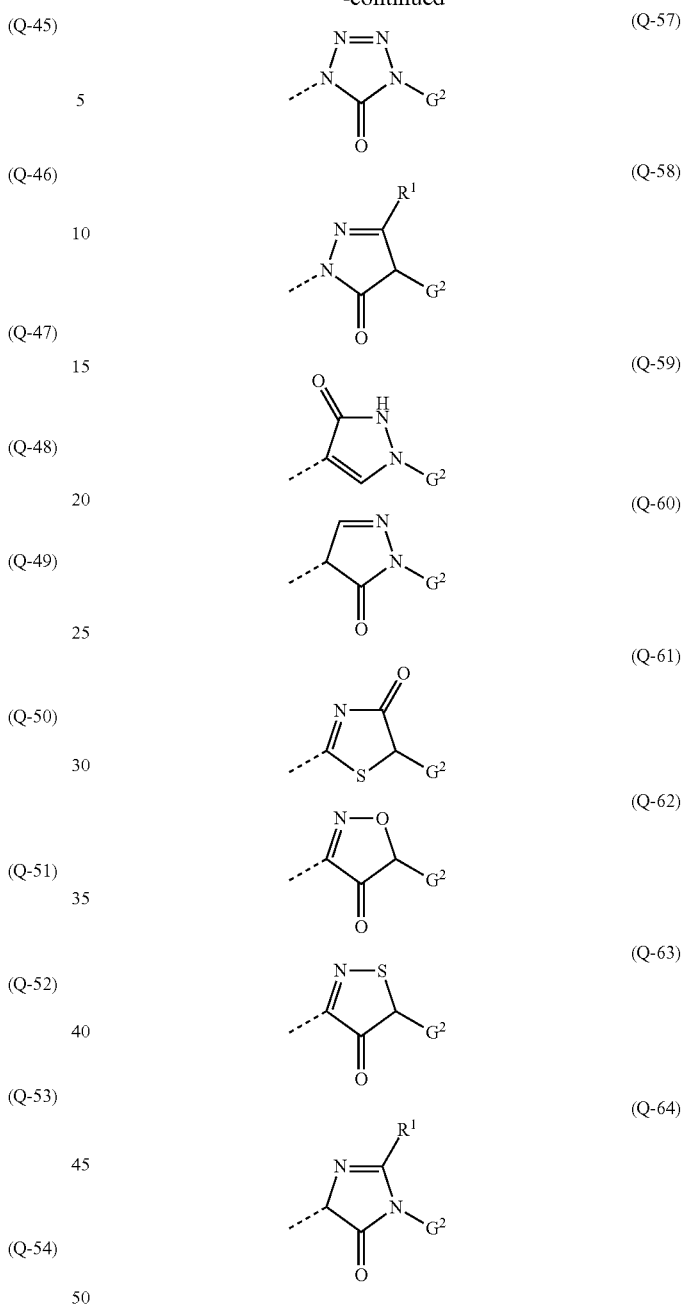

where the broken line marks the bond between Q and the adjacent pyridyl or pyrimidyl ring in the formula (I).

U represents hydrogen, $C_1$-$C_6$-alkyl, $C_1$-$C_6$-haloalkyl or $C_3$-$C_6$-cycloalkyl.

$R^1$ represents hydrogen, halogen, cyano, hydroxyl, $C_1$-$C_6$-alkyl, $C_1$-$C_6$-haloalkyl, $C_1$-$C_6$-alkoxy or $C_3$-$C_6$-cycloalkyl.

$R^2$ represents hydrogen, halogen, cyano, hydroxyl, $C_1$-$C_6$-alkyl, $C_1$-$C_6$-haloalkyl, $C_1$-$C_6$-alkoxy, $C_1$-$C_6$-alkoxycarbonyl or $C_3$-$C_6$-cycloalkyl.

In the radicals Q-1, Q-2, Q-3, Q-4, Q-5, Q-6, Q-7, Q-8, Q-9, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-33, Q-34, Q-35, Q-36, Q-37, Q-38, Q-39, Q-40, Q-44, Q-45, Q-46, Q-48, Q-49, Q-50, Q-51, Q-52, Q-53, Q-58, Q-61, Q-62 and Q-63

$G^2$ represents a radical from the group consisting of ($G^2$-1) to ($G^2$-30).

In the radicals Q-10, Q-26, Q-29, Q-32, Q-41, Q-42, Q-43, Q-47, Q-54, Q-55, Q-56, Q-57, Q-59, Q-60 and Q-64 $G^2$ represents a radical from the group consisting of $G^2$-2, $G^2$-3, $G^2$-4, $G^2$-5, $G^2$-6, $G^2$-7, $G^2$-9, $G^2$-10, $G^2$-11, $G^2$-12, $G^2$-13, $G^2$-14, $G^2$-15, $G^2$-16, $G^2$-17, $G^2$-18, $G^2$-19, $G^2$-20, $G^2$-21, $G^2$-22, $G^2$-23, $G^2$-24, $G^2$-25, $G^2$-26, $G^2$-27, $G^2$-29 and $G^2$-30.

The radicals ($G^2$-1) to ($G^2$-30) have the following meanings:

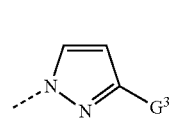
($G^2$-1)

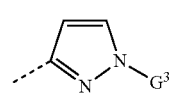
($G^2$-2)

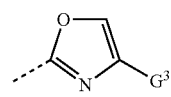
($G^2$-3)

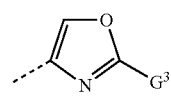
($G^2$-4)

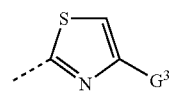
($G^2$-5)

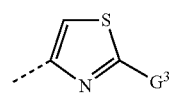
($G^2$-6)

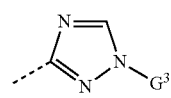
($G^2$-7)

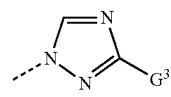
($G^2$-8)

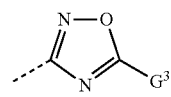
($G^2$-9)

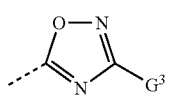
($G^2$-10)

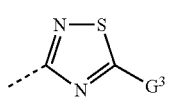
($G^2$-11)

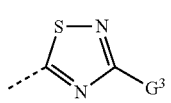
($G^2$-12)

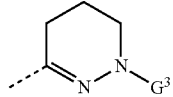
($G^2$-13)

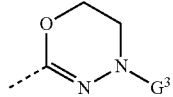
($G^2$-14)

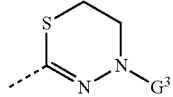
($G^2$-15)

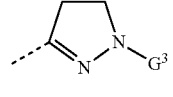
($G^2$-16)

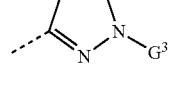
($G^2$-17)

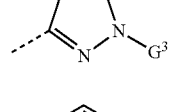
($G^2$-18)

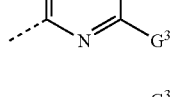
($G^2$-19)

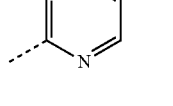
($G^2$-20)

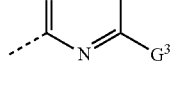
($G^2$-21)

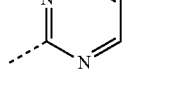
($G^2$-22)

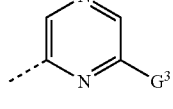
($G^2$-23)

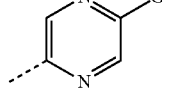
($G^2$-24)

($G^2$-25)

-continued

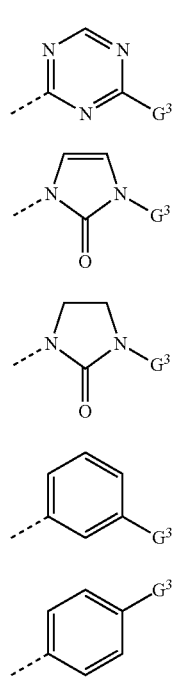

(G²-26)

(G²-27)

(G²-28)

(G²-29)

(G²-30)

where the broken line marks the bond between G² and the adjacent heterocycle in the radicals (Q-1) to (Q-64).

G³ represents a radical from the group consisting of halogen, nitro, amino, cyano, $C_1$-$C_6$-alkylamino, $C_1$-$C_6$-haloalkylamino, di-($C_1$-$C_6$)-alkylamino, $C_1$-$C_6$-alkyl, $C_1$-$C_6$-haloalkyl, optionally halogen-, $C_1$-$C_6$-alkyl-, $C_1$-$C_6$-haloalkyl-, $C_1$-$C_6$-alkoxy-, $C_1$-$C_6$-haloalkoxy-substituted $C_3$-$C_6$-cycloalkyl in which one or two ring members may in each case be replaced by a heteroatom from the group consisting of nitrogen, oxygen and sulfur, where two oxygen atoms must not be directly adjacent to one another, optionally halogen-, $C_1$-$C_6$-alkyl-, $C_1$-$C_6$-haloalkyl-, $C_1$-$C_6$-alkoxy-, $C_1$-$C_6$-haloalkoxy-substituted $C_3$-$C_6$-cycloalkenyl in which one or two ring members may in each case be replaced by a heteroatom from the group consisting of nitrogen, oxygen and sulfur, where two oxygen atoms must not be directly adjacent to one another, $C_3$-$C_6$-cycloalkyl-$C_1$-$C_6$-alkyl in which one or two ring members may in each case be replaced by a heteroatom from the group consisting of nitrogen, oxygen and sulfur, where two oxygen atoms must not be directly adjacent to one another, $C_1$-$C_6$-alkoxy, $C_1$-$C_6$-haloalkoxy, $C_1$-$C_6$-alkoxy-$C_1$-$C_6$-alkyl, halogenated $C_1$-$C_6$-alkoxy-$C_1$-$C_6$-alkyl, bis($C_1$-$C_6$-alkoxy)-$C_1$-$C_6$-alkyl, bis($C_1$-$C_6$-haloalkoxy)-$C_1$-$C_6$-alkyl, $C_1$-$C_6$-alkoxy($C_1$-$C_6$-alkylsulfanyl)-$C_1$-$C_6$-alkyl, $C_1$-$C_6$-alkoxy($C_1$-$C_6$-alkylsulfinyl)-$C_1$-$C_6$-alkyl, $C_1$-$C_6$-alkoxy($C_1$-$C_6$-alkylsulfonyl)-$C_1$-$C_6$-alkyl, bis($C_1$-$C_6$-alkylsulfanyl)-$C_1$-$C_6$-alkyl, bis($C_1$-$C_6$-haloalkylsulfanyl)-$C_1$-$C_6$-alkyl, bis($C_1$-$C_6$-hydroxyalkylsulfanyl)-$C_1$-$C_6$-alkyl, $C_1$-$C_6$-alkoxycarbonyl, $C_1$-$C_6$-alkoxycarbonyl-$C_1$-$C_6$-alkyl, alpha-hydroxyimino-$C_1$-$C_6$-alkoxycarbonyl-$C_1$-$C_6$-alkyl, alpha-$C_1$-$C_6$-alkoxyimino-$C_1$-$C_6$-alkoxycarbonyl-$C_1$-$C_6$-alkyl, $C(X)NR^3R^4$ (in which X represents oxygen, sulfur, $NR^5$ or NOH, $R^3$ represents hydrogen or $C_1$-$C_6$-alkyl and $R^4$ and $R^5$ independently of one another represent a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkoxycarbonyl, $C_1$-$C_6$-alkoxycarbonyl-$C_1$-$C_6$-alkyl, $C_1$-$C_6$-alkylthio-$C_1$-$C_6$-alkyl, aryl, aryl-$C_1$-$C_6$-alkyl and hetaryl-$C_1$-$C_6$-alkyl or $R^3$ and $R^4$ together with the nitrogen atom to which they are attached form a 4- to 7-membered ring which may contain one or two further heteroatoms from the group consisting of nitrogen, oxygen and sulfur, where two oxygen atoms must not be directly adjacent to one another, or $R^3$ and $R^5$ together with the nitrogen atoms to which they are attached form a 4- to 7-membered ring which, in addition to the nitrogen atoms, does not contain any further heteroatoms as ring members, $NR^6R^7$ (in which $R^6$ represents hydrogen or $C_1$-$C_6$-alkyl and $R^7$ represents a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-alkoxycarbonyl-$C_1$-$C_6$-alkyl, $C_1$-$C_6$-alkylthio-$C_1$-$C_6$-alkyl, aryl, aryl-$C_1$-$C_6$-alkyl or hetaryl-$C_1$-$C_6$-alkyl or $R^6$ and $R^7$ together with the nitrogen atom to which they are attached form a ring which may contain one or two further heteroatoms from the group consisting of nitrogen, oxygen and sulfur, where two oxygen atoms must not be directly adjacent to one another), $C_1$-$C_6$-alkylthio, $C_1$-$C_6$-alkylsulfinyl, $C_1$-$C_6$-alkylsulfonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by $C_1$-$C_6$-alkyl, $C_1$-$C_6$-haloalkyl, $C_1$-$C_6$-alkoxy and $C_1$-$C_6$-alkoxy-$C_1$-$C_6$-alkyl), phenyl (which for its part may be substituted by halogen, cyano, nitro, $C_1$-$C_6$-alkyl and $C_1$-$C_6$-haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl) and the heteroarylalkyl radicals triazolylalkyl, pyridylalkyl, pyrimidylalkyl and oxadiazolylalkyl (which for their part may be substituted by halogen and $C_1$-$C_6$-alkyl), or G³ represents a radical from the group consisting of (B-1) to (B-9)

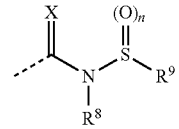

(B-1)

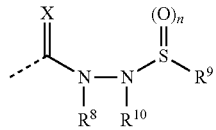

(B-2)

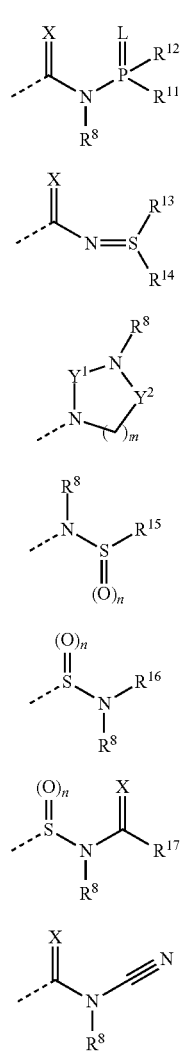

(B-3)

(B-4)

(B-5)

(B-6)

(B-7)

(B-8)

(B-9)

where the broken line marks the bond between G³ and the adjacent ring in the radicals (G²-1) to (G²-30).

X represents oxygen or sulfur.

n represents 1 or 2.

R⁸ represents a radical from the group consisting of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, optionally halogen-substituted $C_1$-$C_6$-alkylcarbonyl and $C_1$-$C_6$-alkylsulfonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or represents a cation such as, for example a mono- or divalent metal ion or an optionally $C_1$-$C_6$-alkyl- or aryl-$C_1$-$C_6$-alkyl-substituted ammonium ion.

R⁹ and R¹⁵ independently of one another represent a radical from the group consisting of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulfinyl-, $C_1$-$C_6$-haloalkylsulfinyl-, $C_1$-$C_6$-alkylsulfonyl- and $C_1$-$C_6$-haloalkylsulfonyl-substituted $C_1$-$C_6$-alkyl, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl in which one ring member may be replaced by a heteroatom from the group consisting of sulfur, oxygen (where oxygen atoms must not be directly adjacent to one another) and nitrogen (and here in particular represent

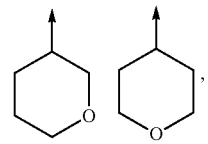

where the arrow in each case marks the bond to the sulfur atom in the radicals (B-1), (B-2) and (B-6)), in each case optionally halogen-, cyano- (also in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulfinyl-, $C_1$-$C_6$-haloalkylsulfinyl-, $C_1$-$C_6$-alkylsulfonyl-, $C_1$-$C_6$-haloalkylsulfonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl or represent NR'R" in which R' and R" independently of one another represent a radical from the group consisting of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

R⁸ and R¹⁵ may also form, together with the N—S(O)ₙ group to which they are attached, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two further heteroatoms from the group consisting of sulfur, oxygen (where oxygen atoms must not be directly adjacent to one another) and nitrogen and/or at least one carbonyl group, in particular, R⁸ and R¹⁵ together with the N—S(O)ₙ group to which they are attached may represent a radical from the group consisting of

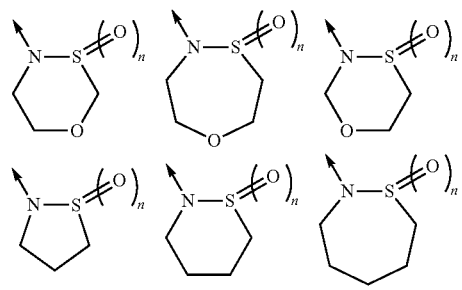

(where the arrow in each case marks the bond to the adjacent ring in the radicals (G²-1) to (G²-30)).

R¹⁷ represents a radical from the group consisting of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulfinyl-, $C_1$-$C_6$-haloalkylsulfinyl-, $C_1$-$C_6$-alkylsulfonyl- or $C_1$-$C_6$-haloalkylsulfonyl-substituted $C_1$-$C_6$-alkyl, $C_1$-$C_6$-alkoxy, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl in which one or two ring members may in each case be replaced by a heteroatom from the group consisting of sulfur, oxygen (where oxygen atoms must not be directly adjacent to one another) and nitrogen, in each case optionally halogen-, cyano- (also in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulfinyl-, $C_1$-$C_6$-haloalkylsulfinyl-, $C_1$-$C_6$-alkylsulfonyl-, $C_1$-$C_6$-haloalkylsulfonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl or represent NR'R" in which R' and R" independently of one another represent a radical from the group consisting of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

$R^{16}$ represents a radical from the group consisting of hydrogen, in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulfinyl-, $C_1$-$C_6$-haloalkylsulfinyl-, $C_1$-$C_6$-alkylsulfonyl- or $C_1$-$C_6$-haloalkylsulfonyl-substituted $C_1$-$C_6$-alkyl, $C_1$-$C_6$-alkoxy, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl in which one or two ring members may in each case be replaced by a heteroatom from the group consisting of sulfur, oxygen (where oxygen atoms must not be directly adjacent to one another) and nitrogen, in each case optionally halogen-, cyano- (also in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulfinyl-, $C_1$-$C_6$-haloalkylsulfinyl-, $C_1$-$C_6$-alkylsulfonyl-, $C_1$-$C_6$-haloalkylsulfonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl or represent NR'R" in which R' and R" independently of one another represent a radical from the group consisting of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

$R^8$ and $R^{17}$ may also form, together with the N—C(X) group to which they are attached, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two further heteroatoms from the group consisting of sulfur, oxygen (where oxygen atoms must not be directly adjacent to one another) and nitrogen and/or one carbonyl group, in particular, $R^8$ and $R^{17}$ together with the N—C(X) group to which they are attached may represent a radical from the group consisting of

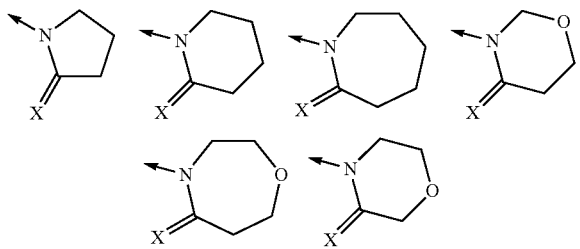

(where the arrow in each case marks the bond to the sulfur atom in the radical (B-8)).

$R^{10}$ represents hydrogen or $C_1$-$C_6$-alkyl, $R^8$ and $R^{10}$ may also represent, together with the nitrogen atoms to which they are attached, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two further heteroatoms from the group consisting of sulfur, oxygen (where oxygen atoms must not be directly adjacent to one another) and nitrogen and/or one carbonyl group, in particular, $R^8$ and $R^{10}$ together with the N—N group to which they are attached may represent a radical from the group consisting of

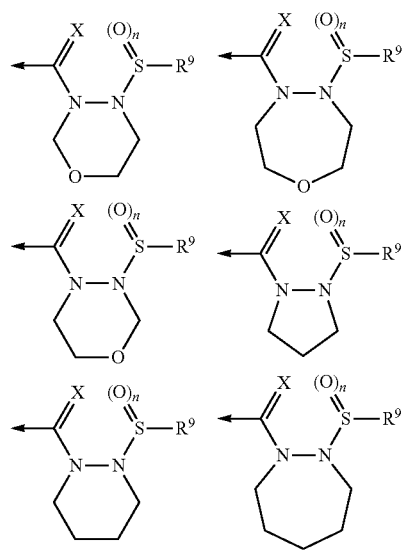

(where the arrow in each case marks the bond to the adjacent ring in the radicals ($G^2$-1) to ($G^2$-30)).

$R^8$ and $R^9$ in the radical (B-1) may also form, together with the N—S(O)$_n$ group to which they are attached, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group consisting of sulfur, oxygen (where oxygen atoms must not be directly adjacent to one another) and nitrogen and/or at least one and preferably one carbonyl group, in particular, $R^8$ and $R^9$ together with the N—S(O)$_n$ group to which they are attached may represent a radical from the group consisting of

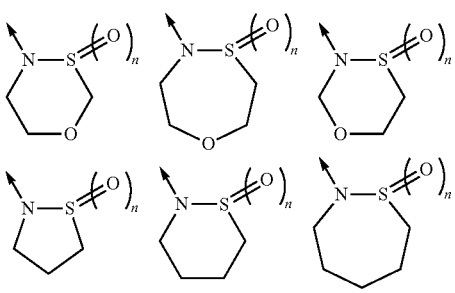

(where the arrow in each case marks the bond to the C(X) group).

R$^9$ and R$^{10}$ may also form, together with the N—S(O)$_n$ group to which they are attached, a saturated or unsaturated and optionally halogen-, C$_1$-C$_6$-alkyl-, C$_1$-C$_6$-haloalkyl-, C$_1$-C$_6$-alkoxy-, C$_1$-C$_6$-haloalkoxy-substituted 5- to 7-membered ring which may contain one or more further heteroatoms from the group consisting of sulfur, oxygen (where oxygen atoms must not be directly adjacent to one another) and nitrogen and/or at least one and preferably one carbonyl group, in particular, R$^9$ and R$^{10}$ together with the N—S(O)$_n$ group to which they are attached may represent a radical from the group consisting of

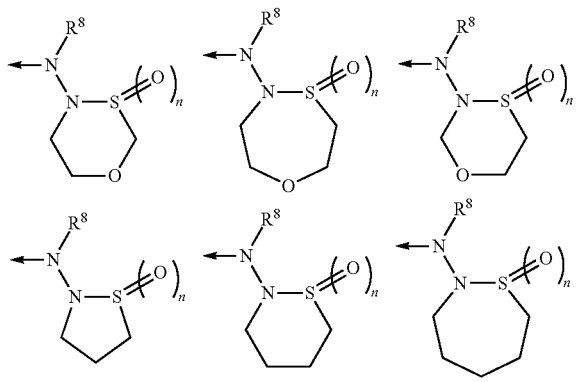

(where the arrow in each case marks the bond to the C(X) group).

R$^8$ and R$^{16}$ may also form, together with the nitrogen atom to which they are attached, a saturated or unsaturated and optionally halogen-, C$_1$-C$_6$-alkyl-, C$_1$-C$_6$-haloalkyl-, C$_1$-C$_6$-alkoxy-, C$_1$-C$_6$-haloalkoxy-substituted 5- to 7-membered ring which may contain one or more further heteroatoms from the group consisting of sulfur, oxygen (where oxygen atoms must not be directly adjacent to one another) and nitrogen and/or at least one and preferably one carbonyl group, in particular, R$^8$ and R$^{16}$ together with the nitrogen atom to which they are attached may represent a radical from the group consisting of

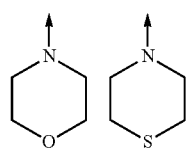

(where the arrow in each case marks the bond to the sulfur atom in the radical (B-7)).

L represents oxygen or sulfur.

R$^{11}$ and R$^{12}$ independently of one another represent an in each case optionally halogen-substituted radical from the group consisting of C$_1$-C$_6$-alkyl, C$_2$-C$_6$-alkenyl, C$_2$-C$_6$-alkynyl, C$_1$-C$_6$-alkoxy, C$_2$-C$_6$-alkenyloxy, C$_2$-C$_6$-alkynyloxy, C$_3$-C$_6$-cycloalkyl, C$_3$-C$_6$-cycloalkyloxy, C$_3$-C$_6$-cycloalkenyloxy, C$_3$-C$_6$-cycloalkyl-C$_1$-C$_6$-alkoxy, C$_1$-C$_6$-alkylthio, C$_2$-C$_6$-alkenylthio, phenoxy, phenylthio, benzyloxy, benzylthio, heteroaryloxy, heteroarylthio, heteroaryl-C$_1$-C$_6$-alkoxy and heteroaryl-C$_1$-C$_6$-alkylthio.

R$^{11}$ and R$^{12}$ may also form, together with the phosphorus atom to which they are attached, a saturated or unsaturated and optionally halogen-, C$_1$-C$_6$-alkyl-, C$_1$-C$_6$-haloalkyl-, C$_1$-C$_6$-alkoxy-, C$_1$-C$_6$-haloalkoxy-substituted 5- to 7-membered ring which may contain one or two heteroatoms from the group consisting of oxygen (where oxygen atoms must not be directly adjacent to one another) and sulfur, in particular, R$^{11}$ and R$^{12}$ together with the phosphorus atom to which they are attached may represent the radical

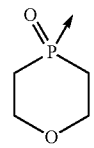

(where the arrow marks the bond to the nitrogen atom in the radical (B-3)).

R$^{13}$ and R$^{14}$ independently of one another represent an in each case optionally halogen-, C$_1$-C$_6$-alkyl-, C$_1$-C$_6$-haloalkyl-, C$_1$-C$_6$-alkoxy-, C$_1$-C$_6$-haloalkoxy-substituted radical from the group consisting of C$_1$-C$_6$-alkyl, C$_2$-C$_6$-alkenyl, C$_2$-C$_6$-alkynyl, phenyl and phenyl-C$_1$-C$_6$-alkyl.

Y$^1$ and Y$^2$ independently of one another represent C═O or S(O)$_2$.

m represents 1, 2, 3 or 4.

Particularly preferred substituents or ranges for the radicals mentioned in the compounds of the formula (I) are illustrated below.

G$^1$ represents N or C-A$^1$.

A$^1$ represents hydrogen, halogen, cyano, nitro, C$_1$-C$_4$-alkyl, C$_1$-C$_4$-haloalkyl, C$_1$-C$_4$-alkoxy or in each case optionally halogen-, C$_1$-C$_4$-alkyl-, C$_1$-C$_4$-haloalkyl-, C$_1$-C$_4$-alkoxy-, C$_1$-C$_4$-haloalkoxy-substituted C$_3$-C$_6$-cycloalkyl or C$_3$-C$_6$-cycloalkenyl in which one or two ring members may in each case be replaced by a heteroatom from the group consisting of nitrogen, oxygen and sulfur, where two oxygen atoms must not be directly adjacent to one another.

A$^2$ represents hydrogen, halogen, cyano, nitro, C$_1$-C$_4$-alkyl, C$_1$-C$_4$-haloalkyl, C$_1$-C$_4$-alkoxy or in each case optionally halogen-, C$_1$-C$_4$-alkyl-, C$_1$-C$_4$-haloalkyl-, C$_1$-C$_4$-alkoxy-, C$_1$-C$_4$-haloalkoxy-substituted C$_3$-C$_6$-cycloalkyl or C$_3$-C$_6$-cycloalkenyl in which one or two ring members may in each case be replaced by a heteroatom from the group consisting of nitrogen, oxygen and sulfur, where two oxygen atoms must not be directly adjacent to one another.

Q represents one of the radicals (Q-1) to (Q-64)
(Q-1) 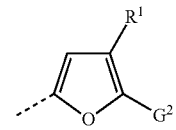
(Q-2) 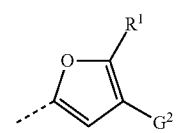
(Q-3) 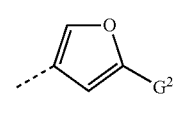
(Q-4) 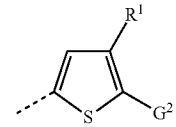
(Q-5) 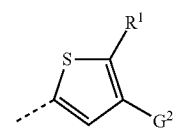
(Q-6) 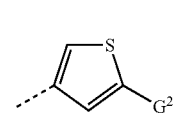
(Q-7) 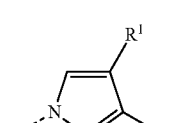
(Q-8) 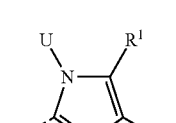
(Q-9) 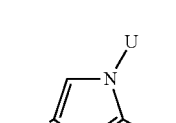
(Q-10) 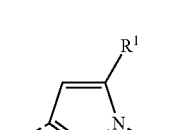
(Q-11) 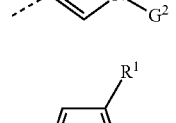
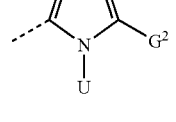
-continued
(Q-12) 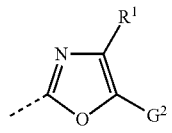
(Q-13) 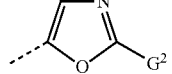
(Q-14) 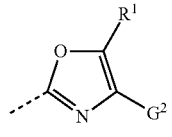
(Q-15) 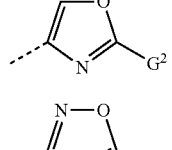
(Q-16) 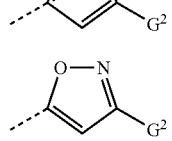
(Q-17) 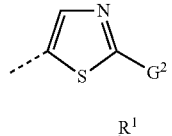
(Q-18) 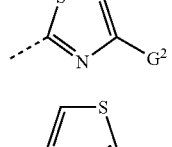
(Q-19) 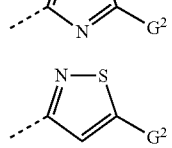
(Q-20) 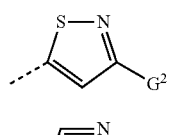
(Q-21) 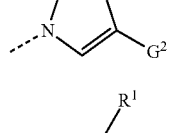
(Q-22) 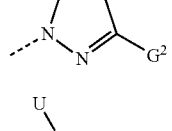
(Q-23) 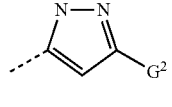
(Q-24)
(Q-25)

(Q-26) 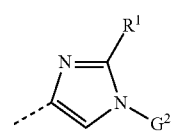
(Q-27) 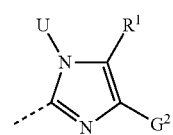
(Q-28) 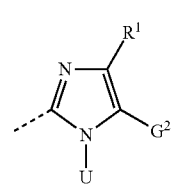
(Q-29) 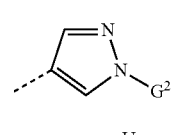
(Q-30) 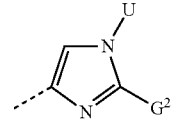
(Q-31) 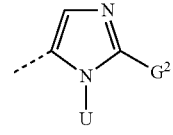
(Q-32) 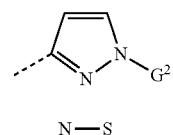
(Q-33) 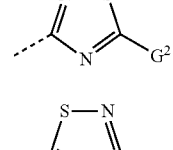
(Q-34) 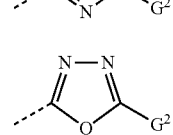
(Q-35) 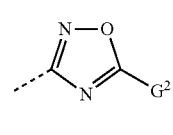
(Q-36) 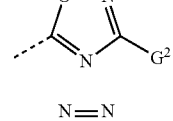
(Q-37) 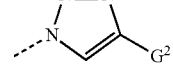
(Q-38) 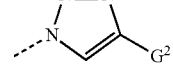
(Q-39) 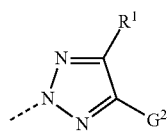
(Q-40) 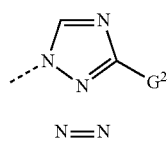
(Q-41) 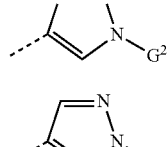
(Q-42) 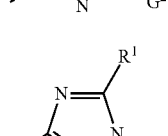
(Q-43) 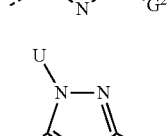
(Q-44) 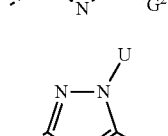
(Q-45) 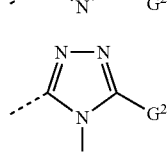
(Q-46) 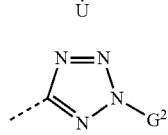
(Q-47) 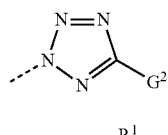
(Q-48) 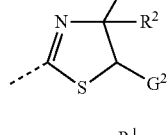
(Q-49) 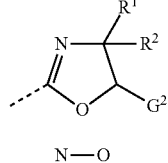
(Q-50) 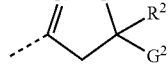
(Q-51) 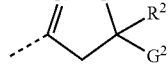

(Q-52) 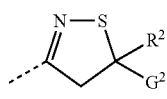

(Q-53) 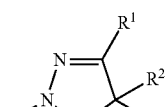

(Q-54) 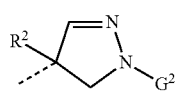

(Q-55) 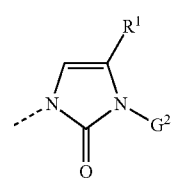

(Q-56) 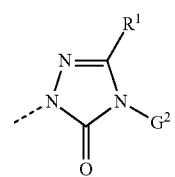

(Q-57) 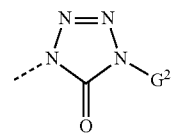

(Q-58) 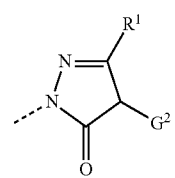

(Q-59) 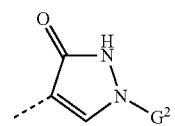

(Q-60) 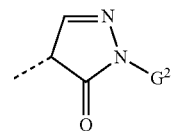

(Q-61) 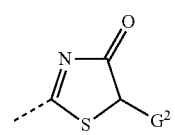

(Q-62) 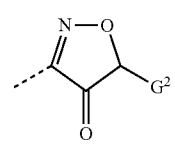

(Q-63) 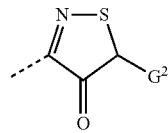

(Q-64) 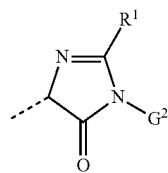

where the broken line marks the bond between Q and the adjacent pyridyl or pyrimidyl ring in the formula (I).

U represents hydrogen, $C_1$-$C_4$-alkyl, $C_1$-$C_4$-haloalkyl or $C_3$-$C_6$-cycloalkyl.

$R^1$ represents hydrogen, halogen, cyano, hydroxyl, $C_1$-$C_4$-alkyl, $C_1$-$C_4$-haloalkyl, $C_1$-$C_4$-alkoxy or $C_3$-$C_6$-cycloalkyl.

$R^2$ represents hydrogen, halogen, cyano, hydroxyl, $C_1$-$C_4$-alkyl, $C_1$-$C_4$-haloalkyl, $C_1$-$C_4$-alkoxy, $C_1$-$C_4$-alkoxycarbonyl or $C_3$-$C_6$-cycloalkyl.

In the radicals Q-1, Q-2, Q-3, Q-4, Q-5, Q-6, Q-7, Q-8, Q-9, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-33, Q-34, Q-35, Q-36, Q-37, Q-38, Q-39, Q-40, Q-44, Q-45, Q-46, Q-48, Q-49, Q-50, Q-51, Q-52, Q-53, Q-58, Q-61, Q-62 and Q-63

$G^2$ represents a radical from the group consisting of ($G^2$-1) to ($G^2$-30).

In the radicals Q-10, Q-26, Q-29, Q-32, Q-41, Q-42, Q-43, Q-47, Q-54, Q-55, Q-56, Q-57, Q-59, Q-60 and Q-64

$G^2$ represents a radical from the group consisting of $G^2$-2, $G^2$-3, $G^2$-4, $G^2$-5, $G^2$-6, $G^2$-7, $G^2$-9, $G^2$-10, $G^2$-11, $G^2$-12, $G^2$-13, $G^2$-14, $G^2$-15, $G^2$-16, $G^2$-17, $G^2$-18, $G^2$-19, $G^2$-20, $G^2$-21, $G^2$-22, $G^2$-23, $G^2$-24, $G^2$-25, $G^2$-26, $G^2$-27, $G^2$-29 and $G^2$-30.

The radicals ($G^2$-1) to ($G^2$-30) have the following meanings:

($G^2$-1) 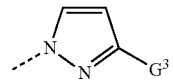

($G^2$-2) 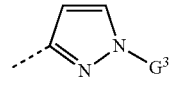

($G^2$-3) 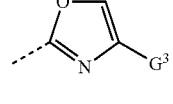

($G^2$-4) 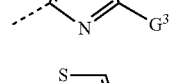

($G^2$-5) 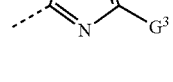

-continued

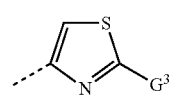 (G²-6)

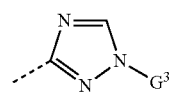 (G²-7)

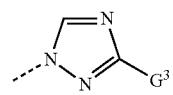 (G²-8)

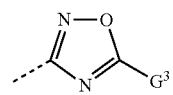 (G²-9)

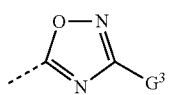 (G²-10)

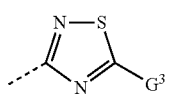 (G²-11)

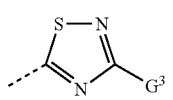 (G²-12)

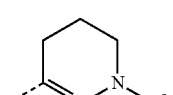 (G²-13)

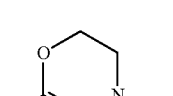 (G²-14)

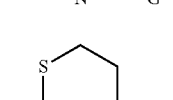 (G²-15)

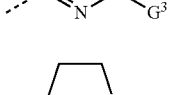 (G²-16)

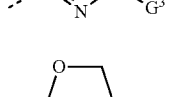 (G²-17)

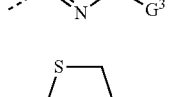 (G²-18)

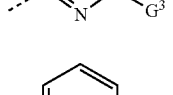 (G²-19)

-continued

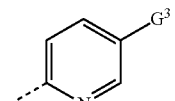 (G²-20)

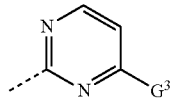 (G²-21)

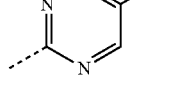 (G²-22)

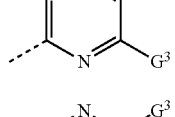 (G²-23)

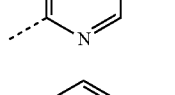 (G²-24)

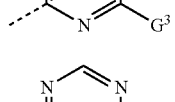 (G²-25)

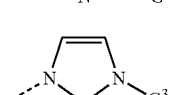 (G²-26)

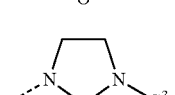 (G²-27)

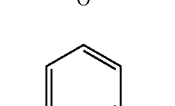 (G²-28)

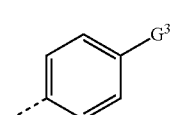 (G²-29)

(G²-30)

where the broken line marks the bond between G² and the adjacent heterocycle in the radicals (Q-1) to (Q-64).

G³ represents a radical from the group consisting of halogen, nitro, amino, cyano, $C_1$-$C_4$-alkylamino, $C_1$-$C_4$-haloalkylamino, di-($C_1$-$C_4$)-alkylamino, $C_1$-$C_4$-alkyl, $C_1$-$C_4$-haloalkyl, optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl in which one or two ring members may in each case be replaced by a heteroatom from the group consisting of nitrogen, oxygen and sulfur, where two oxygen atoms must not be directly adjacent to one another, optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkenyl in which one or two ring members may in each case be replaced by a heteroatom from the group consisting of nitrogen, oxygen and sulfur, where two oxygen atoms must not be directly adjacent to one another, $C_3$-$C_6$-cycloalkyl-$C_1$-$C_4$-alkyl in which one or two ring members may in each case be replaced by a heteroatom from the group consisting of nitrogen, oxygen and sulfur, where two oxygen atoms must not be directly adjacent to one another, $C_1$-$C_4$-alkoxy, $C_1$-$C_4$-haloalkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis($C_1$-$C_4$-haloalkoxy)-$C_1$-$C_4$-alkyl, $C_1$-$C_4$-alkoxy($C_1$-$C_4$-alkylsulfanyl)-$C_1$-$C_4$-alkyl, $C_1$-$C_4$-alkoxy($C_1$-$C_4$-alkylsulfinyl)-$C_1$-$C_4$-alkyl, $C_1$-$C_4$-alkoxy($C_1$-$C_4$-alkylsulfonyl)-$C_1$-$C_4$-alkyl, bis($C_1$-$C_4$-alkylsulfanyl)-$C_1$-$C_4$-alkyl, bis($C_1$-$C_4$-haloalkylsulfanyl)-$C_1$-$C_4$-alkyl, bis($C_1$-$C_4$-hydroxyalkylsulfanyl)-$C_1$-$C_4$-alkyl, $C_1$-$C_4$-alkoxycarbonyl, $C_1$-$C_4$-alkoxycarbonyl-$C_1$-$C_4$-alkyl, alpha-hydroxyimino-$C_1$-$C_4$-alkoxycarbonyl-$C_1$-$C_4$-alkyl, alpha-$C_1$-$C_4$-alkoxyimino-$C_1$-$C_4$-alkoxycarbonyl-$C_1$-$C_4$-alkyl, $C(X)NR^3R^4$ (in which X represents oxygen, sulfur, $NR^5$ or NOH, $R^3$ represents hydrogen or $C_1$-$C_4$-alkyl and $R^4$ and $R^5$ independently of one another represent a radical from the group consisting of hydrogen, $C_1$-$C_4$-alkyl, $C_1$-$C_4$-haloalkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl or $R^3$ and $R^4$ together with the nitrogen atom to which they are attached form a 4- to 7-membered ring which may contain one or two further heteroatoms from the group consisting of nitrogen, oxygen and sulfur, where two oxygen atoms must not be directly adjacent to one another, or $R^3$ and $R^5$ together with the nitrogen atoms to which they are attached form a 4- to 7-membered ring which, in addition to the nitrogen atoms, does not contain any further heteroatoms as ring members), $NR^6R^7$ (in which $R^6$ represents hydrogen or $C_1$-$C_4$-alkyl and $R^7$ represents a radical from the group consisting of hydrogen, $C_1$-$C_4$-alkyl, $C_1$-$C_4$-haloalkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl or hetaryl-$C_1$-$C_4$-alkyl or $R^6$ and $R^7$ together with the nitrogen atom to which they are attached form a ring which may contain one or two heteroatoms from the group consisting of nitrogen, oxygen and sulfur, where two oxygen atoms must not be directly adjacent to one another), $C_1$-$C_4$-alkylthio, $C_1$-$C_4$-alkylsulfinyl, $C_1$-$C_4$-alkylsulfonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by $C_1$-$C_4$-alkyl, $C_1$-$C_4$-haloalkyl, $C_1$-$C_4$-alkoxy and $C_1$-$C_4$-alkoxy-$C_1$-$C_4$-alkyl), phenyl (which for its part may be substituted by halogen, cyano, nitro, $C_1$-$C_4$-alkyl and $C_1$-$C_4$-haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroarylalkyl radicals triazolylalkyl, pyridylalkyl, pyrimidylalkyl and oxadiazolylalkyl (which for their part may be substituted by halogen and $C_1$-$C_4$-alkyl), or $G^3$ represents a radical from the group consisting of

(B-1)

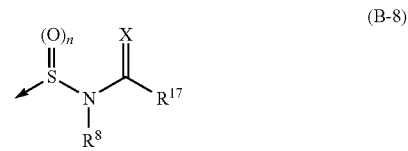

(B-8)

where the arrow marks the bond between $G^3$ and the adjacent ring in the radicals ($G^2$-1) to ($G^2$-30).

X represents oxygen.

n represents 2.

$R^8$ represents a radical from the group consisting of hydrogen, $C_1$-$C_4$-alkyl and $C_1$-$C_4$-alkoxy-$C_1$-$C_4$-alkyl, optionally halogen-substituted $C_1$-$C_4$-alkylcarbonyl or $C_1$-$C_4$-alkylsulfonyl, optionally halogen-substituted $C_1$-$C_4$-alkoxycarbonyl, optionally halogen-, $C_1$-$C_4$-alkyl-, $C_1$-$C_4$-alkoxy-, $C_1$-$C_4$-haloalkyl- and cyano-substituted $C_3$-$C_6$-cycloalkylcarbonyl, or represents a cation such as, for example a mono- or divalent metal ion or an optionally $C_1$-$C_4$-alkyl- or aryl-$C_1$-$C_4$-alkyl-substituted ammonium ion.

$R^{17}$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulfinyl-, $C_1$-$C_4$-haloalkylsulfinyl-, $C_1$-$C_4$-alkylsulfonyl- and $C_1$-$C_4$-haloalkylsulfonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl in which one or two ring members may in each case be replaced by a heteroatom from the group consisting of sulfur, oxygen (where oxygen atoms must not be directly adjacent to one another) and nitrogen (and here in particular represents

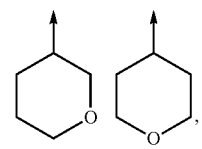

where the arrow in each case marks the bond to the C(X) group in the radical (B-8), in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulfinyl-, $C_1$-$C_4$- haloalkylsulfinyl-, $C_1$-$C_4$-alkylsulfonyl-, $C_1$-$C_4$-haloalkylsulfonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or represents NR'R" in which R' and R" independently of one another represent a radical from the group consisting of hydrogen and, $C_1$-$C_4$-alkyl. $R^9$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulfinyl-, $C_1$-$C_4$-haloalkylsulfinyl-, $C_1$-$C_4$-alkylsulfonyl- and $C_1$-$C_4$-haloalkylsulfonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl in which one or two ring members may in each case be replaced by a heteroatom from the group consisting of sulfur, oxygen (where oxygen atoms must not be directly adjacent to one another) and nitrogen (and here in particular represents

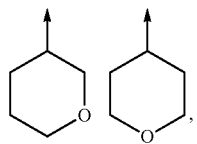

where the arrow in each case marks the bond to the sulfur atom in the radical (B-1), in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulfinyl-, $C_1$-$C_4$-haloalkylsulfinyl-, $C_1$-$C_4$-alkylsulfonyl-, $C_1$-$C_4$-haloalkylsulfonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl, heteroaryl-$C_1$-$C_4$-alkyl or represents NR'R" in which R' and R" independently of one another represent a radical from the group consisting of hydrogen and $C_1$-$C_4$-alkyl.

In a notable group of compounds of the formula (I), $G^1$ represents CH or CF, $A^2$ represents hydrogen, Q represents a radical from the group consisting of Q-2, Q-12, Q-16, Q-18, Q-25, Q-26, Q-29, Q-32, Q-38, Q-43 and Q-56, $G^2$ represents $G^2$-19 and $G^3$ represents pyrimidyl or dioxanyl.

If in the above definitions sulfur and/or nitrogen are present in rings, for example in expressions such as "in which the rings may contain at least one heteroatom from the group consisting of sulfur, oxygen (where oxygen atoms must not be directly adjacent to one another) and nitrogen" or "in which one or two ring members may in each case be replaced by a heteroatom from the group consisting of sulfur, oxygen (where oxygen atoms must not be directly adjacent to one another) and nitrogen", then the sulfur may optionally also be present as SO or $SO_2$ and the nitrogen, unless present as —N═, may, in addition to NH, also be present as N-alkyl (in particular N—$C_1$-$C_6$-alkyl).

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (including as part of a larger unit, for example hetarylalkyl) is selected from the group of pyrimidyl, oxadiazolyl, oxazolyl, pyrazinyl, imidazolyl, thiazolyl and furanyl.

In the very particularly preferred definitions, unless stated otherwise, halogen is selected from the group of fluorine, chlorine, bromine and iodine, preferably in turn from the group of fluorine, chlorine and bromine, hetaryl (including as part of a larger unit, for example hetarylalkyl) is selected from the group of pyrimidyl, oxadiazolyl, oxazolyl, pyrazinyl, imidazolyl, thiazolyl and furanyl.

Halogen-substituted radicals, for example haloalkyl, are mono- or polyhalogenated, up to the maximum number of possible substituents. In the case of polyhalogenation, the halogen atoms may be identical or different. Halogen denotes fluorine, chlorine, bromine and iodine, in particular fluorine, chlorine and bromine.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted groups can be mono or polysubstituted, where in the case of polysubstitutions the substituents can be identical or different.

The radical definitions or elucidations given above, in general terms or within areas of preference, apply both to the end products and correspondingly to the starting materials and intermediates.

These radical definitions can be combined with one another as desired, i.e. including combinations between the given preferred ranges.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

In a preferred embodiment, the invention relates to compounds of the formula (I-1a)

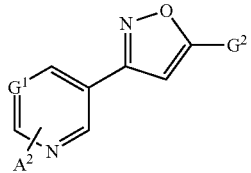

(I-1a)

in which $A^2$, $G^1$ and $G^2$ have the meaning given above.

In a further preferred embodiment, the invention relates to compounds of the formula (I-2a)

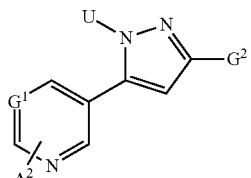

(I-2a)

in which $A^2$, $G^1$, $G^2$ and U have the meaning given above.

In a further preferred embodiment, the invention relates to compounds of the formula (I-3a)

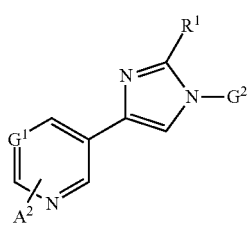

(I-3a)

in which $A^2$, $G^1$, $G^2$ and $R^1$ have the meaning given above.

In a further preferred embodiment, the invention relates to compounds of the formula (I-4-a)

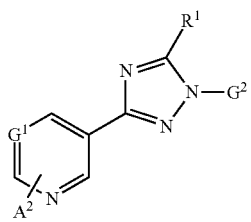

(I-4a)

in which $A^2$, $G^1$, $G^2$ and $R^1$ have the meaning given above.

In a further preferred embodiment, the invention relates to compounds of the formula (I-5a)

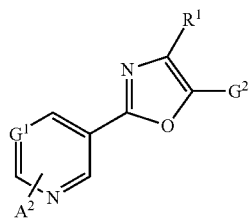

(I-5a)

in which $A^2$, $G^1$, $G^2$ and $R^1$ have the meaning given above.

In a further preferred embodiment, the invention relates to compounds of the formula (I-6a)

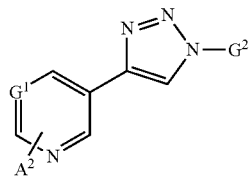

(I-6a)

in which $A^2$, $G^1$ and $G^2$ have the meaning given above.

In a further preferred embodiment, the invention relates to compounds of the formula (I-7a)

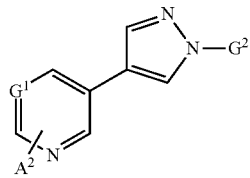

(I-7a)

in which $A^2$, $G^1$ and $G^2$ have the meaning given above.

In a further preferred embodiment, the invention relates to compounds of the formula (I-1b)

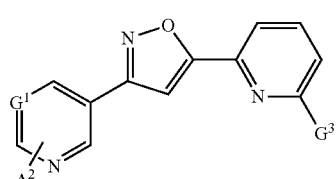

(I-1b)

in which $A^2$, $G^1$ and $G^3$ have the meaning given above.

In a further preferred embodiment, the invention relates to compounds of the formula (I-2b)

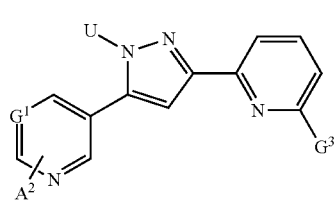

(I-2b)

in which $A^2$, $G^1$, $G^3$ and U have the meaning given above.

In a further preferred embodiment, the invention relates to compounds of the formula (I-3b)

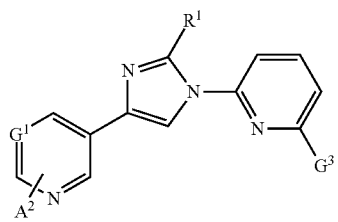
(I-3b)

in which $A^2$, $G^1$, $G^3$ and $R^1$ have the meaning given above.

In a further preferred embodiment, the invention relates to compounds of the formula (I-4-b)

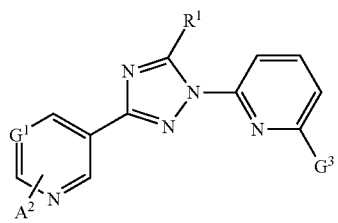
(I-4b)

in which $A^2$, $G^1$, $G^3$ and $R^1$ have the meaning given above.

In a further preferred embodiment, the invention relates to compounds of the formula (I-5b)

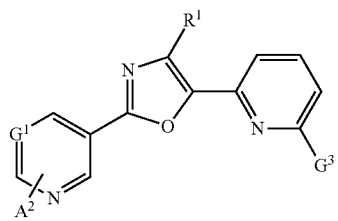
(I-5b)

in which $A^2$, $G^1$, $G^3$ and $R^1$ have the meaning given above.

In a further preferred embodiment, the invention relates to compounds of the formula (I-6b)

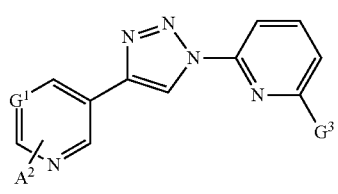
(I-6b)

in which $A^2$, $G^1$ and $G^3$ have the meaning given above.

In a further preferred embodiment, the invention relates to compounds of the formula (I-7b)

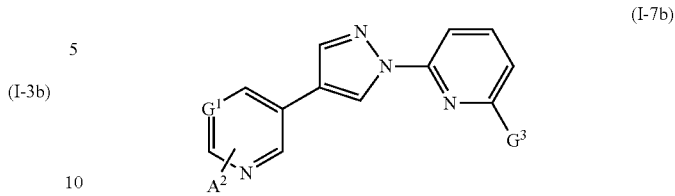
(I-7b)

in which $A^2$, $G^1$ and $G^3$ have the meaning given above.

In a further preferred embodiment, the invention relates to compounds of the formula (I-1c)

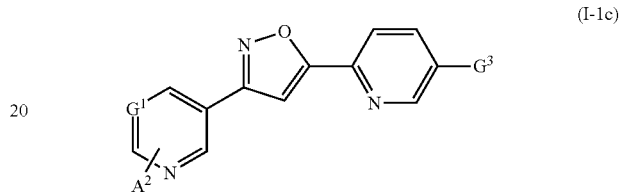
(I-1c)

in which $A^2$, $G^1$ and $G^3$ have the meaning given above.

In a further preferred embodiment, the invention relates to compounds of the formula (I-2c)

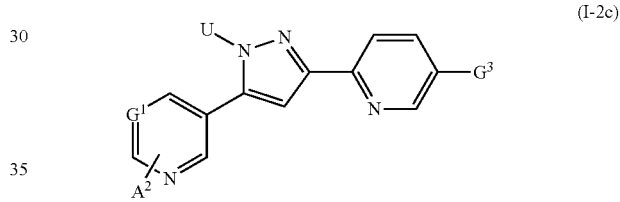
(I-2c)

in which $A^2$, $G^1$, $G^3$ and U have the meaning given above.

In a further preferred embodiment, the invention relates to compounds of the formula (I-3c)

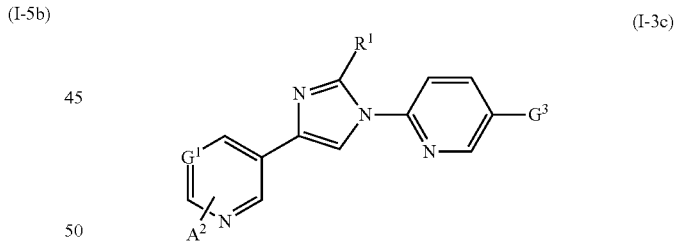
(I-3c)

in which $A^2$, $G^1$, $G^3$ and $R^1$ have the meaning given above.

In a further preferred embodiment, the invention relates to compounds of the formula (I-4-c)

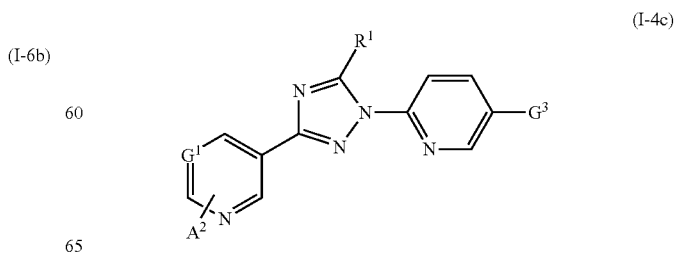
(I-4c)

in which $A^2$, $G^1$, $G^3$ and $R^1$ have the meaning given above.

In a further preferred embodiment, the invention relates to compounds of the formula (I-5c)

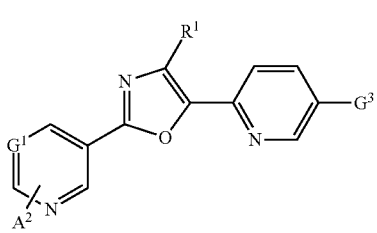

(I-5c)

in which $A^2$, $G^1$, $G^3$ and $R^1$ have the meaning given above.

In a further preferred embodiment, the invention relates to compounds of the formula (I-6c)

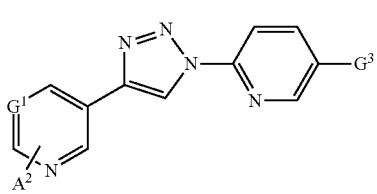

(I-6c)

in which $A^2$, $G^1$ and $G^3$ have the meaning given above.

In a further preferred embodiment, the invention relates to compounds of the formula (I-7c)

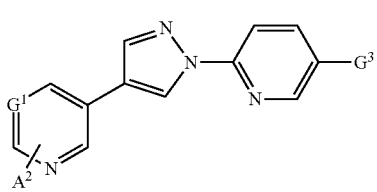

(I-7c)

in which $A^2$, $G^1$ and $G^3$ have the meaning given above.

In a further preferred embodiment, the invention relates to compounds of the formula (I-1d)

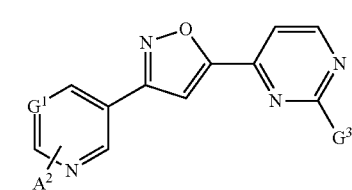

(I-1d)

in which $A^2$, $G^1$ and $G^3$ have the meaning given above.

In a further preferred embodiment, the invention relates to compounds of the formula (I-2d)

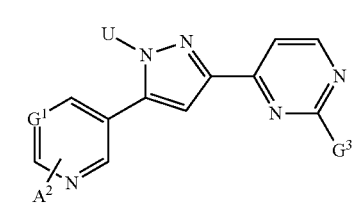

(I-2d)

in which $A^2$, $G^1$, $G^3$ and U have the meaning given above.

In a further preferred embodiment, the invention relates to compounds of the formula (I-3d)

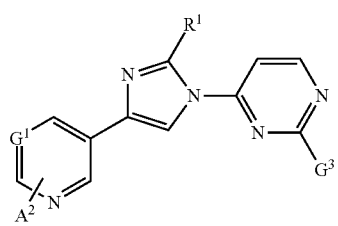

(I-3d)

in which $A^2$, $G^1$, $G^3$ and $R^1$ have the meaning given above.

In a further preferred embodiment, the invention relates to compounds of the formula (I-4-d)

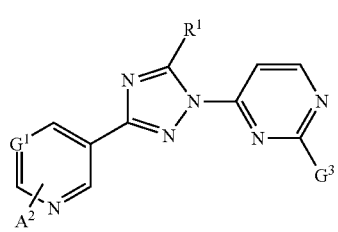

(I-4d)

in which $A^2$, $G^1$, $G^3$ and $R^1$ have the meaning given above.

In a further preferred embodiment, the invention relates to compounds of the formula (I-5d)

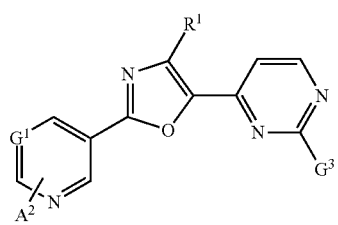

(I-5d)

in which $A^2$, $G^1$, $G^3$ and $R^1$ have the meaning given above.

In a further preferred embodiment, the invention relates to compounds of the formula (I-6d)

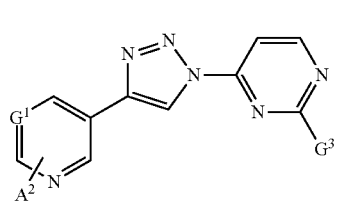

(I-6d)

in which $A^2$, $G^1$ and $G^3$ have the meaning given above.

In a further preferred embodiment, the invention relates to compounds of the formula (I-7d)

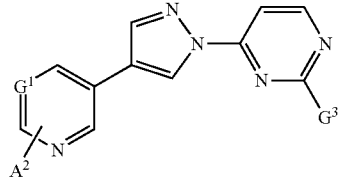
(I-7d)

in which $A^2$, $G^1$ and $G^3$ have the meaning given above.

In a further preferred embodiment, the invention relates to compounds of the formula (I-1e)

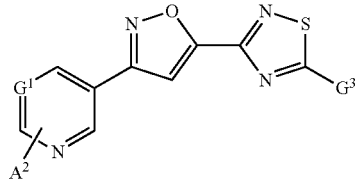
(I-1e)

in which $A^2$, $G^1$ and $G^3$ have the meaning given above.

In a further preferred embodiment, the invention relates to compounds of the formula (I-2e)

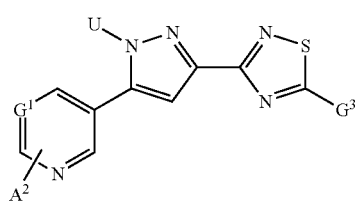
(I-2e)

in which $A^2$, $G^1$, $G^3$ and U have the meaning given above.

In a further preferred embodiment, the invention relates to compounds of the formula (I-3e)

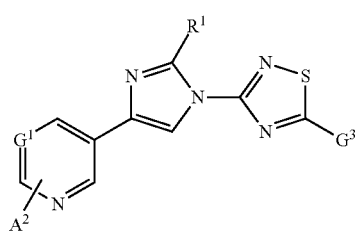
(I-3e)

in which $A^2$, $G^1$, $G^3$ and $R^1$ have the meaning given above.

In a further preferred embodiment, the invention relates to compounds of the formula (I-4-e)

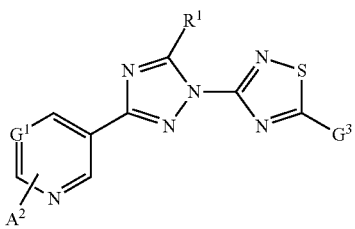
(I-4e)

in which $A^2$, $G^1$, $G^3$ and $R^1$ have the meaning given above.

In a further preferred embodiment, the invention relates to compounds of the formula (I-5e)

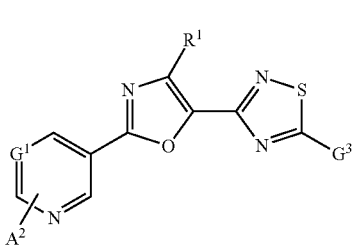
(I-5e)

in which $A^2$, $G^1$, $G^3$ and $R^1$ have the meaning given above.

In a further preferred embodiment, the invention relates to compounds of the formula (I-6e)

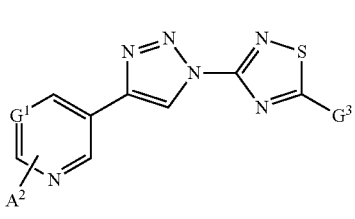
(I-6e)

in which $A^2$, $G^1$ and $G^3$ have the meaning given above.

In a further preferred embodiment, the invention relates to compounds of the formula (I-7e)

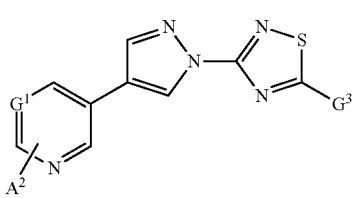
(I-7e)

in which $A^2$, $G^1$ and $G^3$ have the meaning given above.

In a further preferred embodiment, the invention relates to compounds of the formula (I-1f)

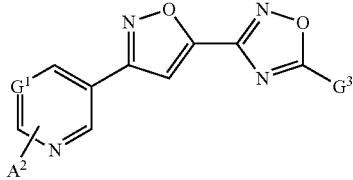

(I-1f)

in which $A^2$, $G^1$ and $G^3$ have the meaning given above.

In a further preferred embodiment, the invention relates to compounds of the formula (I-2f)

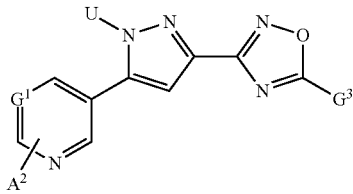

(I-2f)

in which $A^2$, $G^1$, $G^3$ and U have the meaning given above.

In a further preferred embodiment, the invention relates to compounds of the formula (I-3f)

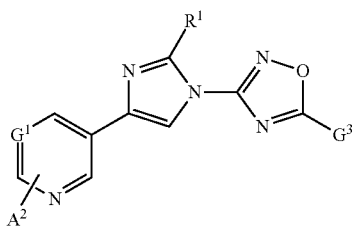

(I-3f)

in which $A^2$, $G^1$, $G^3$ and $R^1$ have the meaning given above.

In a further preferred embodiment, the invention relates to compounds of the formula (I-4-f)

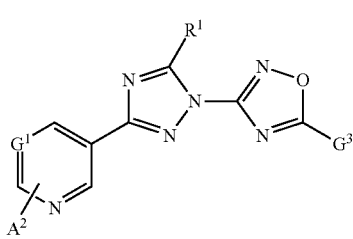

(I-4f)

in which $A^2$, $G^1$, $G^3$ and $R^1$ have the meaning given above.

In a further preferred embodiment, the invention relates to compounds of the formula (I-5f)

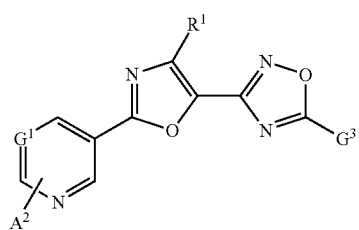

(I-5f)

in which $A^2$, $G^1$, $G^3$ and $R^1$ have the meaning given above.

In a further preferred embodiment, the invention relates to compounds of the formula (I-6f)

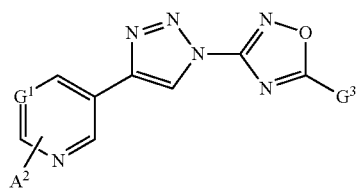

(I-6f)

in which $A^2$, $G^1$ and $G^3$ have the meaning given above.

In a further preferred embodiment, the invention relates to compounds of the formula (I-7f)

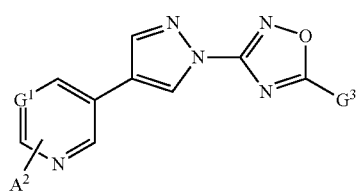

(I-7f)

in which $A^2$, $G^1$ and $G^3$ have the meaning given above.

In a further preferred embodiment, the invention relates to compounds of the formula (I-1g)

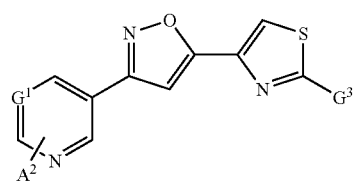

(I-1g)

in which $A^2$, $G^1$ and $G^3$ have the meaning given above.

In a further preferred embodiment, the invention relates to compounds of the formula (I-2g)

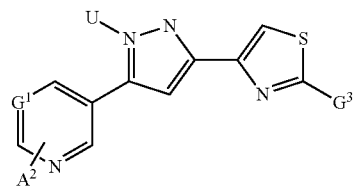

(I-2g)

in which $A^2$, $G^1$, $G^3$ and U have the meaning given above.

In a further preferred embodiment, the invention relates to compounds of the formula (I-3g)

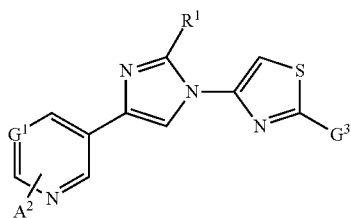

(I-3g)

in which $A^2$, $G^1$, $G^3$ and $R^1$ have the meaning given above.

In a further preferred embodiment, the invention relates to compounds of the formula (I-4-g)

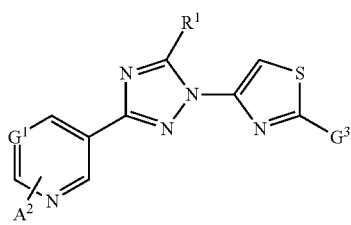

(I-4g)

in which $A^2$, $G^1$, $G^3$ and $R^1$ have the meaning given above.

In a further preferred embodiment, the invention relates to compounds of the formula (I-5g)

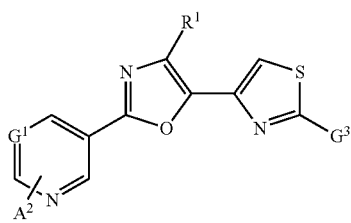

(I-5g)

in which $A^2$, $G^1$, $G^3$ and $R^1$ have the meaning given above.

In a further preferred embodiment, the invention relates to compounds of the formula (I-6g)

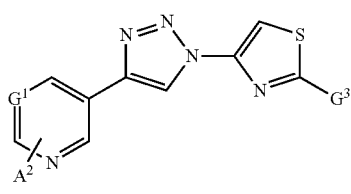

(I-6g)

in which $A^2$, $G^1$, $G^3$ and $R^1$ have the meaning given above.

In a further preferred embodiment, the invention relates to compounds of the formula (I-7g)

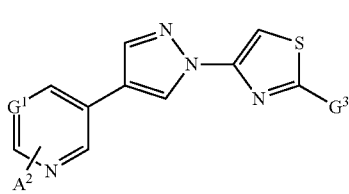

(I-7g)

in which $A^2$, $G^1$ and $G^3$ have the meaning given above.

In a further preferred embodiment, the invention relates to compounds of the formula (I-1 h)

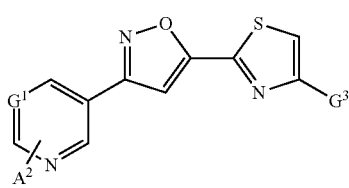

(I-1h)

in which $A^2$, $G^1$ and $G^3$ have the meaning given above.

In a further preferred embodiment, the invention relates to compounds of the formula (I-2h)

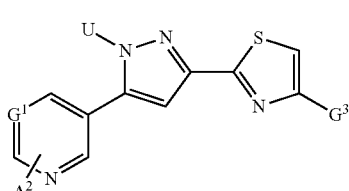

(I-2h)

in which $A^2$, $G^1$, $G^3$ and U have the meaning given above.

In a further preferred embodiment, the invention relates to compounds of the formula (I-3h)

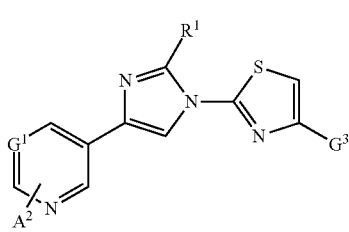

(I-3h)

in which $A^2$, $G^1$, $G^3$ and $R^1$ have the meaning given above.

In a further preferred embodiment, the invention relates to compounds of the formula (I-4-h)

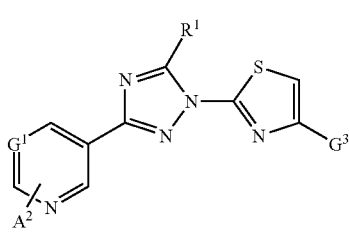

(I-4h)

in which $A^2$, $G^1$, $G^3$ and $R^1$ have the meaning given above.

In a further preferred embodiment, the invention relates to compounds of the formula (I-5h)

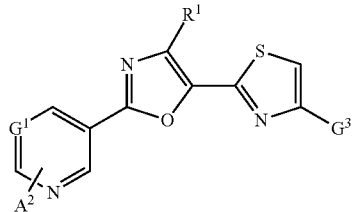
(I-5h)

in which $A^2$, $G^1$, $G^3$ and $R^1$ have the meaning given above.

In a further preferred embodiment, the invention relates to compounds of the formula (I-6h)

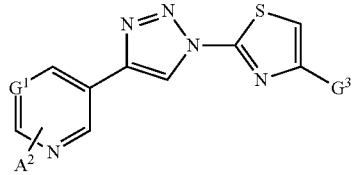
(I-6h)

in which $A^2$, $G^1$, $G^3$ and $R^1$ have the meaning given above.

In a further preferred embodiment, the invention relates to compounds of the formula (I-7h)

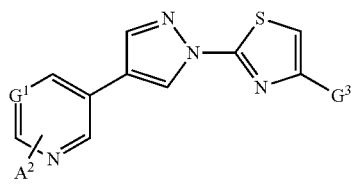
(I-7h)

in which $A^2$, $G^1$ and $G^3$ have the meaning given above.

In a further preferred embodiment, the invention relates to compounds of the formula (I-1i)

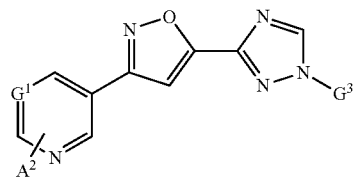
(I-1i)

in which $A^2$, $G^1$ and $G^3$ have the meaning given above.

In a further preferred embodiment, the invention relates to compounds of the formula (I-2i)

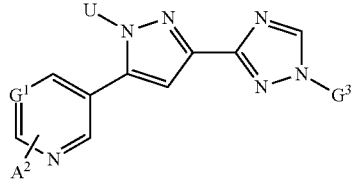
(I-2i)

in which $A^2$, $G^1$, $G^3$ and U have the meaning given above.

In a further preferred embodiment, the invention relates to compounds of the formula (I-3i)

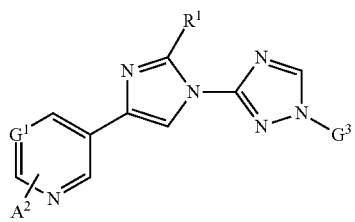
(I-3i)

in which $A^2$, $G^1$, $G^3$ and $R^1$ have the meaning given above.

In a further preferred embodiment, the invention relates to compounds of the formula (I-4i)

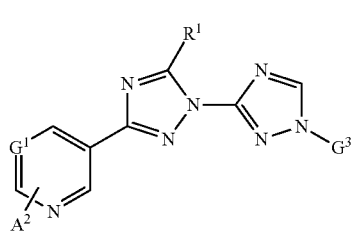
(I-4i)

in which $A^2$, $G^1$, $G^3$ and $R^1$ have the meaning given above.

In a further preferred embodiment, the invention relates to compounds of the formula (I-5i)

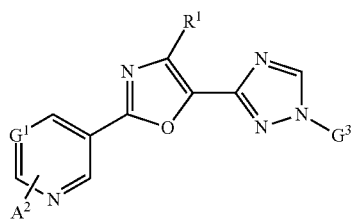
(I-5i)

in which $A^2$, $G^1$, $G^3$ and $R^1$ have the meaning given above.

In a further preferred embodiment, the invention relates to compounds of the formula (I-6i)

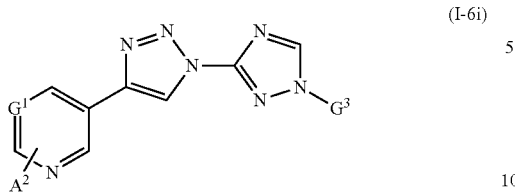
(I-6i)

in which $A^2$, $G^1$, $G^3$ and $R^1$ have the meaning given above.

In a further preferred embodiment, the invention relates to compounds of the formula (I-7i)

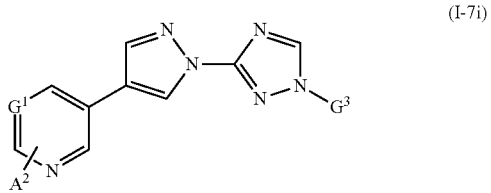
(I-7i)

in which A2, $G^1$ and $G^3$ have the meaning given above.

In a further preferred embodiment, the invention relates to compounds of the formula (I-1j)

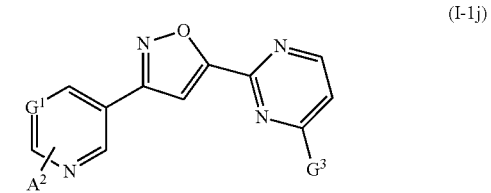
(I-1j)

in which $A^2$, $G^1$ and $G^3$ have the meaning given above.

In a further preferred embodiment, the invention relates to compounds of the formula (I-2j)

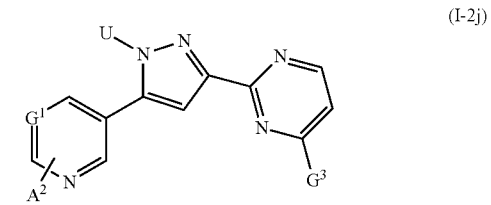
(I-2j)

in which $A^2$, $G^1$, $G^3$ and U have the meaning given above.

In a further preferred embodiment, the invention relates to compounds of the formula (I-3j)

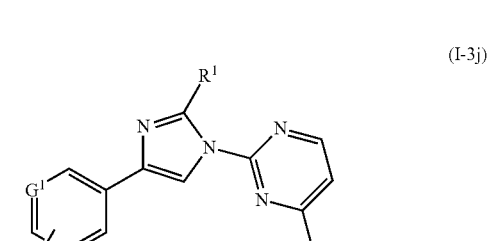
(I-3j)

in which $A^2$, $G^1$, $G^3$ and $R^1$ have the meaning given above.

In a further preferred embodiment, the invention relates to compounds of the formula (I-4-j)

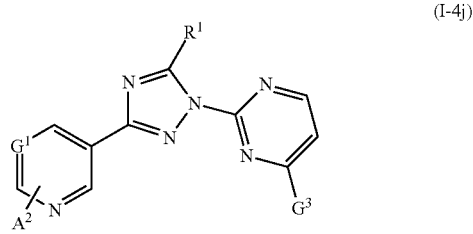
(I-4j)

in which $A^2$, $G^1$, $G^3$ and $R^1$ have the meaning given above.

In a further preferred embodiment, the invention relates to compounds of the formula (I-5j)

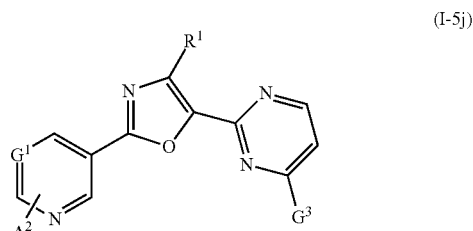
(I-5j)

in which $A^2$, $G^1$, $G^3$ and $R^1$ have the meaning given above.

In a further preferred embodiment, the invention relates to compounds of the formula (I-6j)

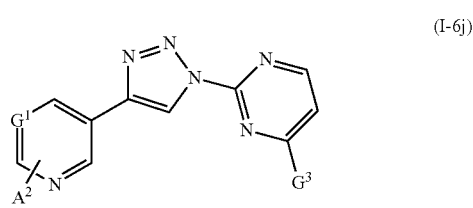
(I-6j)

in which $A^2$, $G^1$, $G^3$ and $R^1$ have the meaning given above.

In a further preferred embodiment, the invention relates to compounds of the formula (I-7j)

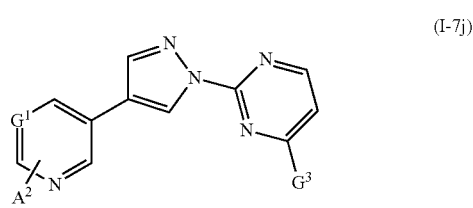
(I-7j)

in which $A^2$, $G^1$ and $G^3$ have the meaning given above.

In a further preferred embodiment, the invention relates to compounds of the formula (I-1k)

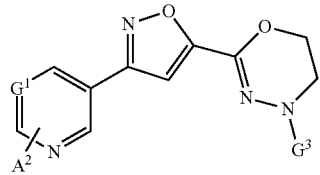

in which $A^2$, $G^1$ and $G^3$ have the meaning given above.

In a further preferred embodiment, the invention relates to compounds of the formula (I-2k)

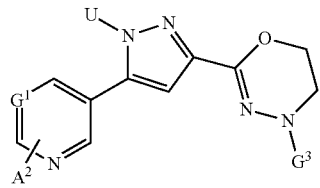

in which $A^2$, $G^1$, $G^3$ and U have the meaning given above.

In a further preferred embodiment, the invention relates to compounds of the formula (I-3k)

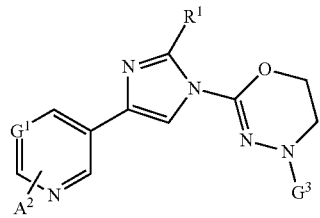

in which $A^2$, $G^1$, $G^3$ and $R^1$ have the meaning given above.

In a further preferred embodiment, the invention relates to compounds of the formula (I-4-k)

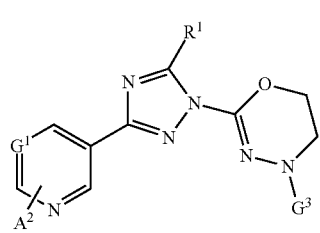

in which $A^2$, $G^1$, $G^3$ and $R^1$ have the meaning given above.

In a further preferred embodiment, the invention relates to compounds of the formula (I-5k)

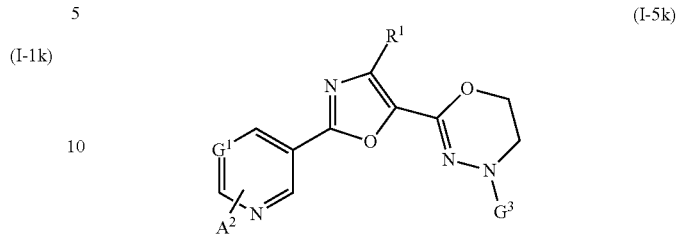

in which $A^2$, $G^1$, $G^3$ and $R^1$ have the meaning given above.

In a further preferred embodiment, the invention relates to compounds of the formula (I-6k)

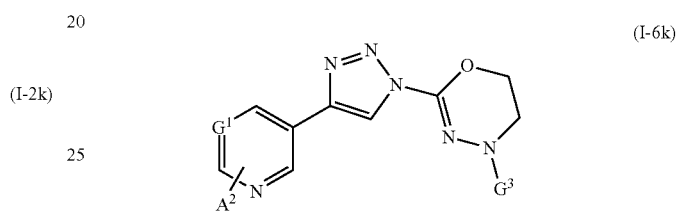

in which $A^2$, $G^1$, $G^3$ and $R^1$ have the meaning given above.

In a further preferred embodiment, the invention relates to compounds of the formula (I-7k)

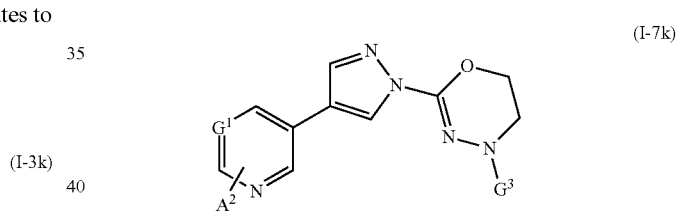

in which $A^2$, $G^1$ and $G^3$ have the meaning given above.

The compounds of the formula (I) according to the invention and their acid addition salts and metal salt complexes are highly active, in particular in the control of animal pests including arthropods and in particular insects.

The compounds of the formula (I) may, where appropriate, depending on the nature of the substituents, be in the form of stereoisomers, i.e. as geometric and/or optically active isomers or isomer mixtures of varying composition. The present invention provides both the pure stereoisomers and any mixtures of these isomers, even if reference is generally only made to compounds of the formula (I).

However, preference is given to using, according to the invention, the optically active stereoisomeric forms of the compounds of the formula (I) and their salts.

Accordingly, the invention relates both to the pure enantiomers and diastereomers and to their mixtures for controlling animal pests including arthropods and in particular insects.

Suitable salts of the compounds of the general formula (I) which may be mentioned are customary nontoxic salts, i.e. salts with appropriate bases and salts with added acids. Salts with inorganic bases, such as alkali metal salts, for example sodium, potassium or cesium salts, alkaline earth metal salts, for example calcium or magnesium salts, ammonium salts, salts with organic bases and also with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulfates, trihydrosulfates, or phosphates, salts with organic carboxylic acids or sulfonic acids, for example formates, acetates, trifluoroacetates, maleates, tartrates, methanesulfonates, benzenesulfonates or para-toluenesulfonates, salts with basic amino acids, for example arginates, aspartates or glutamates and the like may be mentioned as being preferred.

The compounds of the formula (I) can be prepared according to one or, if appropriate, also according to a plurality of the synthesis variants shown in Reaction Schemes 1 to 11.

Compounds of the formula (I) in which the heterocycle Q represents Q-1, Q-2, Q-3, Q-4, Q-5, Q-6, Q-7, Q-8, Q-9, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-32, Q-33, Q-34, Q-35, Q-36, Q-37, Q-38, Q-39, Q-40, Q-44, Q-45, Q-46 or Q-48 and the radical $G^2$ represents, for example, $G^2$-19, $G^2$-20, $G^2$-21, $G^2$-22, $G^2$-23, $G^2$-24, $G^2$-25 and $G^2$-26 can be prepared, for example, according to Reaction Scheme 1.

220272 A1); Q-1 and $G^2$-19 (cf. V. Pomel, *J. Med. Chem.* 2006, 49, 3857-3871); Q-24 and $G^2$-19 or $G^2$-22 (cf. M. P. Curtis et al., *Tetrahedron Lett.* 2009, 50, 5479-5481).

Corresponding coupling reactions have also been described for trialkyltin-substituted heteroaryl compounds (M=$SnR_3$) and can be applied in an analogous manner: Q-23 and $G^2$-19 (cf. US 2003/55085 A1); Q-16 and $G^2$-19 (cf. Y. Kondo et al., *Tetrahedron Lett.* 1989, 30, 4249-4250); Q-48 and $G^2$-19 (cf. B. C. Bookser, *Tetrahedron Lett.* 2000, 41, 2805-2809); Q-12 and $G^2$-23 (cf. D. L. Boger et al., *J. Med. Chem.* 2005, 48, 1849-1856); Q-4 and $G^2$-19 (cf. S. W. Thomas et al., *J. Am. Chem. Soc.* 2006, 128, 16641-16648).

Corresponding reactions with trialkylzinc-substituted heteroaryl compounds (M=$ZnR_3$) are also known and can be applied in an analogous manner: Q-1 and $G^2$-19 (cf. US 2008/171754 A1; D. R. Gauthier, *Org. Lett.* 2004, 4, 375-378).

Compounds of the formula (I) in which Q represents Q-1, Q-4, Q-6, Q-7, Q-12, Q-13, Q-14, Q-15, Q-16, Q-17, Q-18, Q-19, Q-20, Q-23, Q-24, Q-25, Q-26, Q-27, Q-28, Q-34, Q-35, Q-36, Q-37, Q-38, Q-39, Q-40, Q-41, Q-45, Q-46, Q-47, Q-49, Q-50, Q-53, Q-55 or Q-58 and the radical $G^2$ represents $G^2$-3, $G^2$-5, $G^2$-9, $G^2$-12, $G^2$-13, $G^2$-16, $G^2$-19, $G^2$-20, $G^2$-21, $G^2$-22, $G^2$-23, $G^2$-24, $G^2$-25 and $G^2$-26 can be prepared, for example, according to Reaction Scheme 2.

Reaction Scheme 1

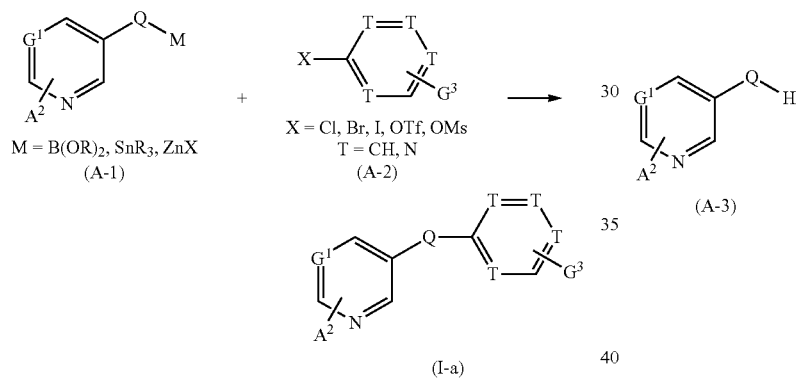

Reaction Scheme 2

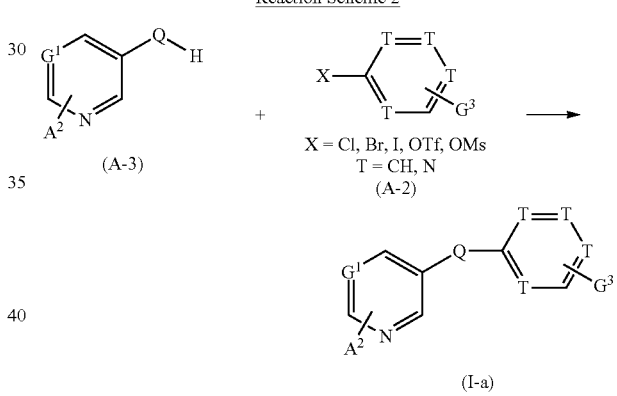

For example, (hetero)arylboronic acids (M=$B(OH)_3$) or (hetero)arylboronic esters (M=$B(OR)_3$) of the formula (A-1) can be reacted with the appropriate $G^3$-substituted heteroaryl compounds of the formula (A-2) which are either halogen-substituted (X=Cl, Br, I) or have another suitable leaving group X (for example X=O—$SO_2CF_3$, O—$SO_2CH_3$), according to generally known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), $2^{nd}$ ed., Wiley-VCH, Weinheim, 2004) in the presence of catalysts from the group of the transition metal salts, to give compounds of the formula (I-a).

The compounds of the formula (A-1) can be obtained by known preparation processes, cf., for example, for Q-4: 3-(5-tributylstannyl-2-thienyl)pyridine derivatives ($Sn(C_4H_9)_3$; H.-F. Lu et al. *Macromolecules* 2003, 36, 1543-1552).

Some of the compounds of the formula (A-2) are known, and/or can be obtained by known preparation processes, for 2-(6-bromopyridin-2-yl)pyrimidine cf., for example, WO 2010/006713, *Tetrahedron Letters* 2000, 41, 1653-1656.

Suitable coupling reactions are described, for example, for the following combinations of the heterocycles Q and a radical $G^2$ and can be applied in an analogous manner: Q-15 and $G^2$-19 (cf. H. Araki et al., *Synlett*, 2006, 4, 555-558); Q-4 and $G^2$-22 (cf. WO2004/13130 A1); Q-6 and $G^2$-22 (cf. US 2003/

For example, heterocyclic compounds of the formula (A-3) can be reacted with the appropriate $G^3$-substituted heterocycles of the formula (A-2) which are either halogen-substituted (X=Cl, Br, I) or have another suitable leaving group X (for example X=O—$SO_2CF_3$, O—$SO_2CH_3$), according to known methods (I. V. Seregin, V. Gevortgyan, *Chem. Soc. Rev.* 2007, 36, 1173-1193; G. P. McGlacken, L. M. Bateman, *Chem. Soc. Rev.* 2009, 38, 2447-2464; D. Alberico, M. E. Scott, M. Lautens, *Chem. Rev.* 2007, 107, 174-238) in the presence of suitable catalysts from the group of the transition metal salts, to give compounds of the formula (I-a) (cf. also the preparation examples, Example E).

Some of the compounds of the formula (A-3) are known, and/or they can be obtained by known preparation processes, cf., for example, for Q-1: 3-(2-furanyl)pyridine (DE 2052536); Q4: 3-(2-thienyl)pyridine; Q-6: (3-thienyl)pyridine (H. Wynberg et al., *J. Org. Chem.* 1969, 34, 3175-3178); Q-7: 1-(2-chloro-3-pyridinyl)-1H-pyrrole (U.S. Pat. No. 4,144,343); Q-12: 2-(3-pyridinyl)oxazole (DE 1112076); Q-13: 5-(3-pyridyl)oxazole (N. Primas et al., *Tetrahedron* 2009, 65, 6348-6353); Q-14: 2-(3-pyridinyl)oxazole (M. Dadkha, B. Prijs, *Helv. Chim. Acta* 1962, 42, 375-381); Q-15:

2-butoxy-5-(4-oxazolyl)pyridine (WO 2003/022821); Q-16: 5-(3-isoxazolyl)-2-methylpyridine (US 2006/287341); Q-17: 2-butoxy-5-(5-isoxazolyl)pyridine (WO 2003/022821); Q-18: 3-(5-thiazolyl)pyridine (WO 2000/009480); Q-19: 3-(2-thiazolyl)pyridine (WO 2010/006713); Q-20: 3-(4-thiazolyl)pyridine (EP 0 641 797); Q-23: 2-(1H-imidazol-1-yl)-2-methylpyridine (H. Chen et al., Synthesis 2010, 9, 1505-1511); Q-24: 3-(1H-pyrazol-1-yl)pyridine (WO 2005/066162); Q-25: 3-(1H-pyrazol-3-yl)pyridine (EP 525879); Q-26: 3-(1H-imidazol-5-yl)pyridine (WO 2000/002875); Q-27 and Q-28: 3-imidazol-2-ylpyridine (U.S. Pat. No. 2,847,417); Q-34: 3-(1,2,4-thiazol-5-yl)pyridine and Q-35: 3-(1,3,4-oxadiazol-2-yl)pyridine (EP 0 116 515); Q-36: 3-(1, 2,4-oxadiazol-3-yl)pyridine and Q-37: 3-(1,2,4-oxadiazol-5-yl)pyridine (K. Hemming, Science of Synthesis 2004, 13, 127-184); Q-38: 2-fluoro-5-(1H-1,2,3-triazol-1-yl)pyridine (WO 2009/129036); Q-39: 2-ethyl-5-(2H-1,2,3-triazol-2-yl)pyridine (WO 1997/01552); Q-40: 3-(1H-1,2,4-triazol-yl) pyridine (M. A. Khan, J. B. Polya, J. Chem. Soc. [Section]C: Organic 1970, 1, 85-91); Q-41: 3-(1H-1,2,3-triazol-5-yl)pyridine hydrochloride (WO 2009/127669); Q-45: 2-chloro-5-(1-methyl-1H-1,2,4-triazol-3-yl)pyridine (WO 2009/105500); Q-46: 3-(1H-1,2,4-triazol-5-yl)pyridine (EP 0 122 693); Q-47: 2-chloro-5-(2H-tetrazol-5-yl)pyridine (S. H. Watterson et al. J. Med. Chem. 2010, 53, 3814-3830); Q-49: 2-(2-thiazolin-2-yl)pyridine dihydrobromide (DD 42938); Q-50: 3-(2-oxazolin-2-yl)pyridine (DE 2158615); Q-53: 3-(phenyl-2-pyrazolin-1-yl)pyridine (R. Huisgen et al., Angew. Chem. 1962, 74, 30); Q-55: 1,3-dihydro-1-(3-pyridinyl-4H-imidazol-2-one (DE 1965320); Q-57: 1,2-dihydro-1-[2[3-(trifluoromethyl)-1H-pyrazol-1-yl]-3-3-pyridinyl]-5H-tetrazol-5-one (WO 98/25912) and Q-58: 2-(5-bromo-3-pyridinyl)-2,4-dihydro-5-methyl-3H-pyrazol-3-one (C. Zwart, J. P. Wibaut, Rec. Travaux Chim. Pays-Bas et de la Belgique 1955, 74, 1062-1069).

Some of the compounds of the formula (A-2) are known, and/or they can be obtained by known preparation processes. Here, the compounds of the formula (A-2) are at the same time representatives of the radicals $G^2$; the following may be mentioned by way of example: $G^2$-3: ethyl 2-bromo-4-oxazolecarboxylate (K. J. Hodgetts, M. T. Kershaw, Org. Lett. 2002, 4, 2905-2907); $G^2$-5: 2-bromo-4-nitrothiazole (DE 2252070); $G^2$-9: ethyl 3-bromo-1,2,4-oxadiazole-5-carboxylate (G. R. Humphrey et al., J. Heterocycl. Chem. 1989, 26, 23-24); $G^2$-12: 3-bromo-5-(methylsulfonyl)-1,2,4-thiadiazole (L. S. Wittenbrook et al., J. Org. Chem. 1973, 38, 465-471): $G^2$-12: 5-bromo-3-methyl-1,2,4-thiadiazole (J. Goerdeler et al., Chem. Ber. 1956, 89, 1534-1543); $G^2$-13: 3-chloro-1,4,5,6-tetrahydro-1-phenylpyridazine (H. A. Dowlatshahi, Synth. Commun. 1987, 17, 1253-1259) and $G^2$-16: 3-chloro-4,5-dihydro-1-phenyl-1H-pyrazole (S. C. Burford et al., EP 127 371).

Such coupling reactions have been described, for example, for the combinations of Q-15 and $G^2$-19 (cf. C. Verrier et al., J. Org. Chem. 2008, 73, 7383-7386); Q-20 and $G^2$-19 or $G^2$-23 (cf. T. Martin et al., Org. Lett. 2008, 10, 2909-2912) and can be applied in an analogous manner.

Compounds of the formula (I) in which Q represents Q-26, Q-29, Q32, Q-41, Q-42, Q-43, Q-47, Q-55 or Q-57 and the radical $G^2$ represents, for example, $G^2$-19, $G^2$-20, $G^2$-21, $G^2$-22, $G^2$-23, $G^2$-24, $G^2$-25 and $G^2$-26 can be prepared, for example, according to Reaction Scheme 3.

Reaction Scheme 3

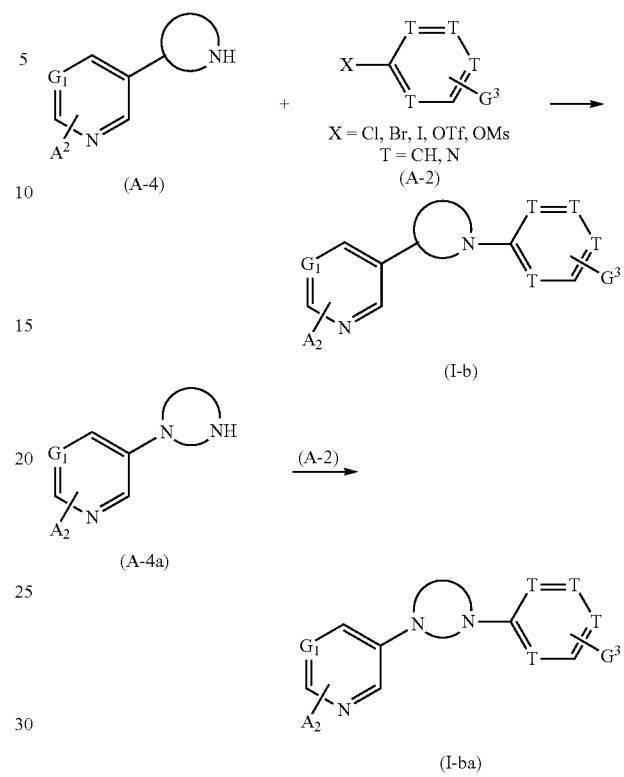

Initially, $G^3$-substituted heterocycles of the formula (A-2) which either are substituted by halogen (X=Cl, Br, I) or have another suitable leaving group X (for example X=O—$SO_2CF_3$, O—$SO_2CH_3$) are reacted with heterocyclic compounds of the formula (A-4) or (A-4-a) according to known methods (Mini-Reviews in Organic Chemistry 2008, 5, 323-330; Molecules 2009, 14, 5169-5178; Pyrazol: Eur. J. Org. Chem. 2004, 4, 695-709) in the presence of suitable catalysts from the group of the transition metal salts to give compounds of the formula (I-b) or (I-ba) (cf. also Preparation Examples C, D and F).

Some of the compounds of the formula (A-4) or (A-4-a) are known, and/or they can be obtained by known preparation processes, cf., for example, for Q-26: 3-(1H-imidazol-4-yl)-pyridine hydrochloride (WO 2000/002875), 5-(1H-imidazol-4-yl)pyrimidine dihydrochloride (WO 2003/004509); Q-29: 2-methyl-5-(1H-pyrazol-4-yl)pyridine (A. N. Kost et al., Zh. Obshchei Khim. 1962, 32, 2606-2612); Q-32: 3-(1H-pyrazol-3-yl)pyridine (EP 1 004 592 A1); Q-41/Q-42: 3-(1H-1,2, 3-triazol-4-yl)pyridine (EP 296 721 A2) Q-43: 3-(1H-1,2,4-triazol-3-yl)pyridine (J. Org. Chem. 1979, 44, 4160-4164); Q-47: 3-bromo-5-(2H-tetrazol-5-yl)pyridine hydrochloride (WO 2010/025553); Q-55: 1,3-dihydro-1-(3-pyridinyl)-2H-imidazol-2-one, 1,3-dihydro-4-methyl-1-(3-pyridinyl)-2H-imidazol-2-one (DE 1965320) or Q-57: 1,2-dihydro-1-(3-pyridinyl)-5H-tetrazol-5-one (EP 692 482).

Some of the compounds of the formula (A-2) are known, and/or they can be obtained by known preparation processes. Here, the compounds of the formula (A-2) are at the same time representatives of the radicals $G^2$, examples of which are mentioned above.

Coupling reactions of this type have been described, for example, for the combinations of Q-26 and $G^2$-22 or $G^2$-23 (cf. US 2003/125267); Q-32 and $G^2$-19 (cf. H. Brunner et al., Chem. Ber. 1992, 125, 701-710), Q-32 and G²-22 (cf. M. Ikeda et al., Chem. Pharm. Bull. 1996, 44, 1700-1706), and Q-47 and G²-19 (cf. WO 2010/5572), (cf. also Preparation Examples, Example C) and can be applied in an analogous manner.

In addition, for example, compounds of the formula (I) in which Q represents Q-1, Q-4, Q-5, Q-6, Q13, Q14, Q-18, Q20 or Q-48 and the radical G² represents G²-3, G²-4, G²-5, G²-6, G²-29, G²-30 can be prepared according to Reaction Scheme 4.

pyridine (M. T. Burger et al., J. Med. Chem. 2006, 49, 1730-1734); Q-5: 3-(4-bromo-2-thienyl)pyridine (WO 2005/005435); Q-6: 3-(5-bromo-3-thienyl)pyridine (Y. Zhang et al., J. Heterocycl. Chem. 1995, 32, 435-444); Q-16: 3-(5-chloro-3-isoxazolyl)pyridine (M. A. El-Badawi et al., Bulg. Chem. Commun. 2008, 40, 70-77); Q-18: 5-(2-chloro-5-thiazolyl)-2-methylpyridine (WO 2006/135604) and Q-19: 3-(4-bromo-5-methyl-2-thiazolyl)pyridine (M. Irie, S. Takami, J. Phys. Org. Chem. 2007, 20, 894-899).

Reaction Scheme 4

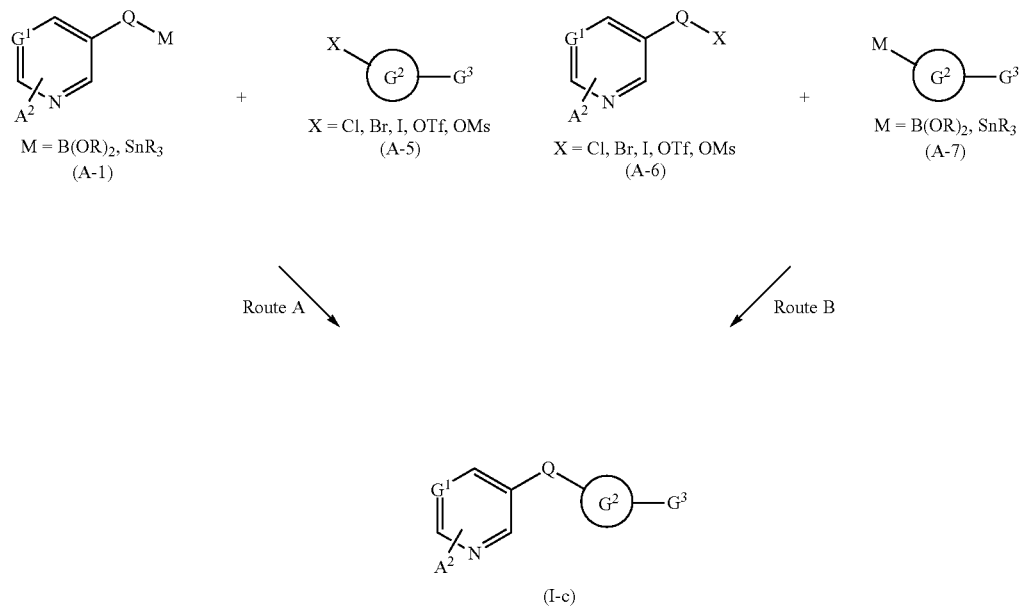

(Hetero)arylboronic acids (M=B(OH)₂), (hetero)arylboronic esters (M=B(OR)₂), trialkyltin-substituted heteroaryl compounds (M=SnR₃) or trialkylzinc-substituted heteroaryl compounds (M=ZnR₃) of the formula (A-1) can be reacted with G³-substituted heterocycles of the formula (A-5) which have either a halogen substituent (X=Cl, Br, I) or another suitable leaving group X (for example X=O—SO₂CF₃, O—SO₂CH₃) according to known methods (Chem. Rev. 1995, 95, 2457-2483; Tetrahedron 2002, 58, 9633-9695; Metal-Catalyzed Cross-Coupling Reactions (Eds.: A. de Meijere, F. Diederich), 2$^{nd}$ ed., Wiley-VCH, Weinheim, 2004) in the presence of suitable catalysts from the group of the transition metal salts, to give compounds of the formula (I-c) (Route A).

Some of the compounds of the formula (A-1) are known, and/or they can be obtained by the preparation processes described above.

Some of the compounds of the formula (A-5) used for Route A are known, and/or they can be obtained by known preparation processes. Here, the compounds of the formula (A-5) are at the same time representatives of the radicals G², examples of which are mentioned above.

Some of the compounds of the formula (A-6) are known, and/or they can be obtained by known preparation processes, cf., for example, starting materials with Q-1: 3-(5-bromo-2-furanyl)pyridine (L. Fisera et al., Coll. Czech. Chem. Commun. 1977, 42, 105-111); Q-2: 3-(4-bromo-3-furanyl)pyridine (WO 2005/005435); Q-4: 3-(5-bromo-2-furanyl)

Some of the compounds of the formula (A-7) required for Route B are known, and/or they can be obtained by known preparation processes. Here, the compounds of the formula (A-7) are at the same time representatives of the radicals G², examples of which are mentioned above, cf., for example, starting materials with G²-2: 1-ethyl-3-(4,4,5,5-tetramethyl-1,3,2-dioxaborolan-2-yl)-1H-pyrazole (WO 2010/075270); G²-3: (4-octyl-2-oxazolyl)boronic acid (JP 2005/223238); G²-4: 2-phenyl-4-(4,4,5,5-tetramethyl-1,3,2-dioxaborolan-2-yl)oxazole (JP 2007/145806); G²-6: 2-phenyl-4-(4,4,5,5-tetramethyl-1,3,2-dioxaborolan-2-yl)thiazole (M. Schnuerch et al., Synthesis 2010, 5, 837-843) and G²-20: (5-methyl-2-pyridinyl)boronic acid (WO 2010/018113);

coupling reactions of this type have been described, for example, for the combinations of Q-1 and G²-29 or G²-30 (Route B: cf. M. A. Ismail et al., J. Med. Chem. 2003, 46, 4761-4769); Q-4 and G²-5 (cf. WO 2008/54702 A1, Negishi coupling); Q-5 and G²-5 (cf. US 2009/149517, Suzuki coupling); Q-6 and G²-2 (cf. WO 2009/112845 A1, Stille coupling); Q-13 and G²-4 (cf E. Flegeau et al., J. Org. Chem. 2008, 73, 3303-3306, Stille coupling); Q-14 and G²-3 (cf. H. Araki et al., Synlett 2006, 555-558, Suzuki coupling); Q-18 and G²-6 (cf. N. F. Langille et al., Org. Lett. 2002, 4, 2485-2488, Stille coupling) and can be carried out in an analogous manner.

Alternatively, the compounds (I-c) according to the invention can also be prepared by Route B from (hetero)arylboronic acids (M=B(OH)₂), (hetero)arylboronic esters (M=B (OR)$_2$), trialkyltin-substituted heteroaryl compounds (M=SnR$_3$) or trialkylzinc-substituted heteroaryl compounds (M=ZnR$_3$) of the formula (A-7) with the appropriate G$^3$-substituted heterocycles of the formula (A-6) which have either a halogen substituent (X=Cl, Br, I) or another suitable leaving group X (for example X=O—SO$_2$CF$_3$, O—SO$_2$CH$_3$) according to the methods mentioned above.

Coupling reactions of this type have been described, for example, for the following combinations of the heterocycles Q and a radical G$^2$: Q-20 and G$^2$-6 (cf. J. Gebauer et al., *Eur. J. Org. Chem.* 2008, 16, 2701-2704; Stille coupling), Q-48 and G$^2$-5 (cf. US 2004/33970 A1, Stille coupling).

Compounds of the general formula (I) in which Q represents Q-1, Q-2, Q-4, Q-5, Q-6, Q-16, Q-18, Q-19, Q-20 and the radical G$^2$ represents G$^2$-1, G$^2$-8, G$^2$-27 or G$^2$-28 can be prepared, for example, according to Reaction Scheme 5.

For example, heterocycles of the formula (A-6) which have either a halogen substituent (X=Cl, Br, I) or another suitable leaving group X (for example X=O—SO$_2$CF$_3$, O—SO$_2$CH$_3$) can be reacted with G$^3$-substituted heterocycles (A-8) in the presence of suitable catalysts from the group of the transition metal salts to give compounds of the formula (I-d) (cf. also Reaction Scheme 3).

Some of the compounds of the formula (A-6) are known, and/or they can be obtained by known preparation processes. Here, the compounds of the formula (A-6) are at the same time representatives of the radicals Q, examples of which are mentioned above.

Some of the compounds of the formula (A-8) are known, and/or they can be obtained by known preparation processes. Here, the compounds of the formula (A-8) are at the same time representatives of the radicals G$^2$, examples of which are mentioned above, cf., for example, starting materials with G$^2$-27: ethyl 2,3-dihydro-2-oxo-1H-imidazole-1-carboxylate (N. J. Leonard, D. F. Wiemer, *J. Amer. Chem. Soc.* 1976, 98, 8218-8221) and G$^2$-28: 1-(4-chlorophenyl)-2-imidazolidinone (JP 07138258).

Coupling reactions of this type have been described, for example, for the combinations of Q-20 and G$^2$-1 or G$^2$-8 (cf. U.S. Pat. No. 6,468,979 B1).

Compounds of the formula (I) in which Q represents Q-16, Q-17, Q-21, Q-22, Q-25, Q-51 or Q-52 and the radical G represents G$^2$-2, G$^2$-3, G$^2$-4, G$^2$-5, G$^2$-6, G$^2$-7, G$^2$-8, G$^2$-9, G$^2$-10, G$^2$-11, G$^2$-12, G$^2$-19, G$^2$-20, G$^2$-21, G$^2$-22, G$^2$-23, G$^2$-24, G$^2$-25, G$^2$-26, G$^2$-29 or G$^2$-30 can be prepared, for example, according to Reaction Scheme 6.

Reaction Scheme 5

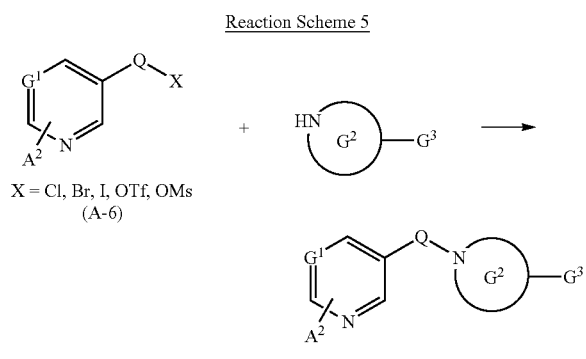

Reaction Scheme 6

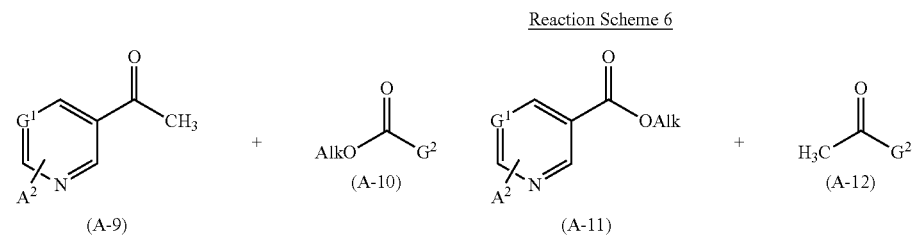

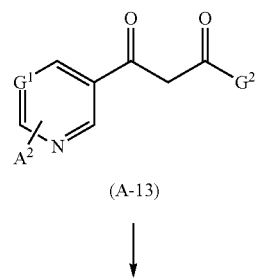

-continued

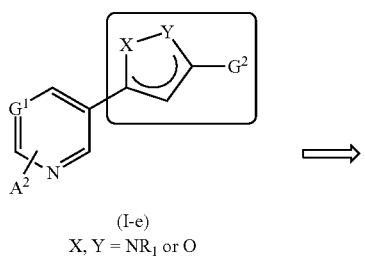

(I-e)
X, Y = NR₁ or O

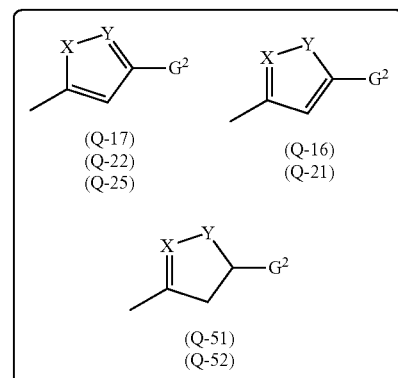

(Q-17)
(Q-22)
(Q-25)

(Q-16)
(Q-21)

(Q-51)
(Q-52)

To prepare the compounds (I-e) according to the invention, in a Claisen condensation (Route A; cf. C. R. Hauser, B. E. Hudson, *Org. Reactions* 1942, 1, 266), hetaryl methyl ketones of the formula (A-9) are reacted with the appropriately substituted carboxylic esters of the formula (A-10) according to methods known per se (cf. WO 2007/67836, cf. Preparation Example A) in the presence of basic reaction auxiliaries to give compounds of the formula (A-13). Alternatively, the compounds (A-13) can also be prepared by base-induced reaction of methyl ketones of the formula (A-12) with heterocyclic esters of the formula (A-11) (Route B; cf., for example, WO2008/4117). The compounds (I-e) according to the invention can be obtained by reacting the diketones (A-13) with bi-functionalized reagents, for example hydroxylamine (cf. E. Belgodere et al., *Heterocycles* 1983, 20, 501-504; cf. also Preparation Example A) or hydrazine derivatives (cf. M. R. D. Giudice et al., *Arch. Pharm.* 2003, 336, 143-154; cf. Preparation Example B), if appropriate in the presence of a suitable acidic reaction auxiliary in a suitable solvent.

Suitable acidic reaction auxiliaries are virtually all mineral acids, organic acids or Lewis acids. The mineral acids preferably include hydrohalic acids such as hydrofluoric acid, hydrochloric acid, hydrobromic acid or hydroiodic acid, and also sulfuric acid, phosphoric acid, phosphorous acid, nitric acid, and the Lewis acids preferably include aluminium(III) chloride, boron trifluoride or its etherate, titanium(V) chloride and tin(V) chloride. The organic acids include formic acid, acetic acid, propionic acid, malonic acid, lactic acid, oxalic acid, fumaric acid, adipinic acid, stearic acid, tartaric acid, oleic acid, methanesulfonic acid, benzoic acid, benzenesulfonic acid or para-toluenesulfonic acid.

The acidic reaction auxiliaries used are preferably organic acids, for example acetic acid.

Some of the compounds of the formula (A-9) are known, and/or they can be obtained by known preparation processes, for 1-(5-fluoro-3-pyridinyl)ethanone and 1-(5-chloro-3-pyridinyl)ethanone, see, for example, WO 2001/038332.

Some of the compounds of the formulae (A-10), (A-11) and (A-12) are likewise known, and/or they can be obtained by known preparation processes (cf. Preparation Example A).

Suitable for use as basic reaction auxiliaries for carrying out the process according to the invention according to Reaction Scheme 6 are all suitable acid binders, for example amines, in particular tertiary amines, and alkali metal and alkaline earth metal compounds.

Examples which may be mentioned are the hydroxides, hydrides, oxides and carbonates of lithium, sodium, potassium, magnesium, calcium and barium, furthermore further basic compounds such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyl-toluidine, N,N-dimethyl-p-aminopyridine, N-methyl-pyrrolidine, N-methyl-piperidine, N-methyl-imidazole, N-methyl-pyrazole, N-methyl-morpholine, N-methyl-hexamethylenediamine, pyridine, 4-pyrrolidinopyridine, 4-dimethylamino-pyridine, quinoline, α-picoline, β-picoline, isoquinoline, pyrimidine, acridine, N,N,N',N'-tetramethylenediamine, N,N',N'-tetraethylenediamine, quinoxaline, N-propyl-diisopropylamine, N-ethyl-diisopropylamine, N,N'-dimethylcyclohexylamine, 2,6-lutidine, 2,4-lutidine or triethylenediamine.

Preference is given to using hydroxides of lithium, potassium or sodium.

Compounds of the general formula (I) in which Q represents Q-38, Q-41, Q-47 or Q48 and the radical $G^2$ represents $G^2$-2, $G^2$-3, $G^2$-4, $G^2$-5, $G^2$-6, $G^2$-7, $G^2$-9, $G^2$-10, $G^2$-11, $G^2$-12, $G^2$-19, $G^2$-20, $G^2$-21, $G^2$-22, $G^2$-23, $G^2$-24, $G^2$-25, $G^2$-26, $G^2$-29 or $G^2$-30 can be prepared, for example, according to Reaction Scheme 7.

Reaction Scheme 7

Route A

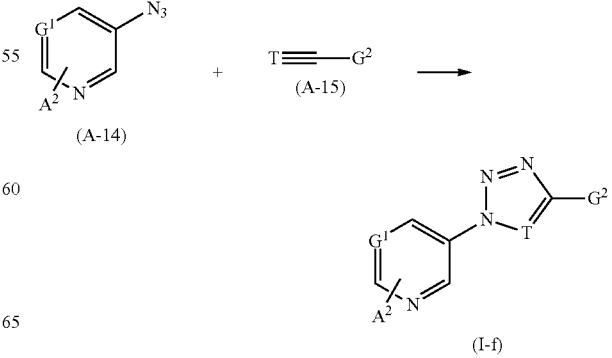

Route B

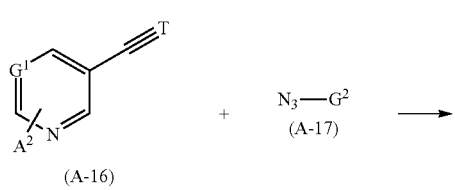

(A-16)

+ N₃—G² (A-17) →

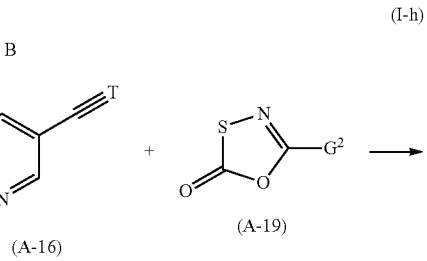

(I-g)

T = CH, N

To prepare the compounds (I-f) or (I-g) according to the invention, heterocyclic azides of the formula (A-14) (Route A) are reacted in a 1,3-dipolar cycloaddition with unsaturated compounds of the formula (A-15) according to methods known per se (cf. Preparation Example G) in the presence of transition metal salts, for example copper(II) sulfate. Alternatively, the unsaturated compounds (A-16) can be reacted with heterocyclic or aromatic azides of the formula (A-17) (Route B).

Some of the compounds of the formula (A-14) are known, and/or they can be prepared by known preparation processes, for 5-azidopyrimidine see K. D. Grimes et al., *Synthesis* 2010, 9, 1441-1448 and for 3-azidopyridine see WO 2005/085214).

Some of the compounds of the formula (A-15) are known, and/or they can be obtained by known preparation processes. $G^2$-6: 4-ethynyl-2-methylthiazole (K. C. Nicolau et al., *ChemBioChem* 2001, 2, 69-75); $G^2$-9: 3-ethynyl-5-[[(3,3,3-trifluoropropyl)thio]methyl]-1,2,4-oxadiazole (WO 2009/028727); $G^2$-11: 3-ethynyl-5-[[(3,3,3-trifluoropropyl)thio]methyl]-1,2,4-thiadiazole (WO 2009/028727) and $G^2$-19: 2-(6-ethynylpyridin-2-yl)pyrimidine (cf. Preparation Example G, step 2).

Some of the compounds of the formulae (A-16) and (A-17) are known, and/or they can be obtained by preparation processes known per se.

Compounds of the general formula (I) in which Q represents Q-21, Q-22, Q-33, Q-34, and the radical $G^2$ represents $G^2$-2, $G^2$-3, $G^2$-4, $G^2$-5, $G^2$-6, $G^2$-7, $G^2$-9, $G^2$-10, $G^2$-11, $G^2$-12, $G^2$-19, $G^2$-20, $G^2$-21, $G^2$-22, $G^2$-23, $G^2$-24, $G^2$-25, $G^2$-26, $G^2$-29 or $G^2$-30 can be prepared, for example, according to Reaction Scheme 8.

Reaction Scheme 8

Route A

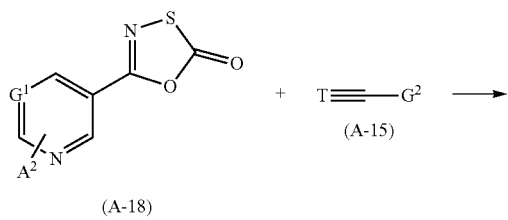

+ T≡≡—G² (A-15) →

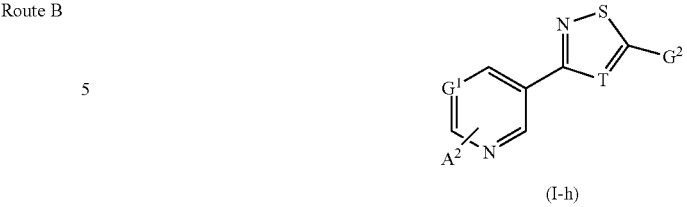

(I-h)

Route B (A-16) + (A-19) →

(I-i)

T = CH, N

To prepare the compounds (I-h) or (I-i) according to the invention, 3,4-oxathiazol-2-ones of the formula (A-18) (Route A) can be reacted in a 1,3-dipolar cycloaddition with unsaturated compounds of the formula (A-15) according to methods known per se (cf. K. S. A. Vallin et al., *J. Org. Chem.* 2009, 74, 9328-9336). Alternatively, the unsaturated compounds (A-16) can be reacted with 3,4-oxathiazol-2-ones of the formula (A-19) (Route B). By thermal decarboxylation, the respective 3,4-oxathiazol-2-ones afford nitrile sulfides which are unstable in situ and react with the compounds (A-15) or (A-16) in a 1,3-dipolar cycloaddition.

Some of the compounds of the formulae (A-15) and (A-16) are known, and/or they can be obtained by the preparation processes described above (cf. Preparation Example G; step 2). Some of the compounds of the formula (A-18) are known, and/or they can be obtained by known preparation processes, for 3-pyridinyl-1,3,4-oxathiazolone, for example, see WO 2000/007446.

Some of the compounds of the formula (A-19) are known, and/or they can be obtained by known preparation processes; cf., for example, $G^2$-20: 5-(2-pyridinyl)-1,3,4-oxathiazol-2-one (N. B. Islam, H. Kwart, *J. Chem. Engineering Data* 1985, 30, 507-509); $G^2$-24: 2-(2-pyridinyl)-1,3,4-oxathiazol-2-one (M. H. Gezginci et al., *J. Med. Chem.* 2001, 44, 1560-1563) and $G^2$-30: [4-(trifluoromethyl)phenyl]-1,2,4-oxadiazol-2-one (US 2005/096362).

Compounds of the general formula (I) in which Q represents Q-1, Q-2, Q-3, Q-4, Q-5, Q-6, Q-7, Q-8, Q-9, Q-10, Q-11, Q-12, Q-13, Q-14, Q-15, Q-16, Q-17, Q-18, Q-19, Q-20, Q-21, Q-22, Q-23, Q-24, Q-25, Q-26, Q-27, Q-28, Q-29, Q-30, Q-31, Q-32, Q-33, Q-34, Q-35, Q-36, Q-37, Q-38, Q-39, Q-40, Q-41, Q-42, Q-43, Q-44, Q-45, Q-46 or Q-48 and the radical $G^2$ represents $G^2$-13 or $G^2$-16 can be prepared according to Reaction Scheme 9.

Reaction Scheme 9

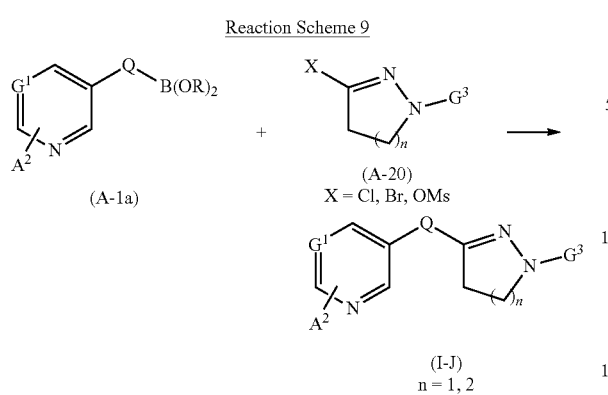

To prepare the compounds (I-j) according to the invention, the boronic acid derivatives of the general formula (A-1a) can be reacted with the appropriate G³-substituted heterocycles of the formula (A-20), which either are halogen-substituted (X=Cl, Br) or have another suitable leaving group X (for example X=O—SO₂CF₃, O—SO₂CH₃), according to known methods (palladium-catalyzed cross-coupling, Suzuki coupling) (cf. H.-J- Wang et al., Tetrahedron Lett. 2005, 46, 2631-2634).

Some of the compounds of the formula (A-1a) are known, and/or they can be obtained by the preparation processes described above.

Some of the compounds of the formula (A-20) are known, and/or they can be obtained by known preparation processes; for G²-13: 3-chloro-1,4,5,6-tetrahydro-1-phenylpyridazine, see H.-J- Wang et al., Tetrahedron Lett. 2005, 46, 2631-2634 and for G²-16: 3-chloro-4,5-dihydro-1-phenyl-1H-pyrazole, see EP 0 127 371.

Compounds of the general formula (I) in which Q represents Q-1, Q-2, Q-3, Q-4, Q-5, Q-6, Q-7, Q-8, Q-9, Q-10, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-33, Q-34, Q-35, Q-36, Q-37, Q-38, Q-39, Q-40, Q-44, Q-45, Q-46, Q-48 or Q-49 and the radical G² represents G²-17 or G²-18 can be prepared, for example according to Reaction Scheme 10.

Reaction Scheme 10

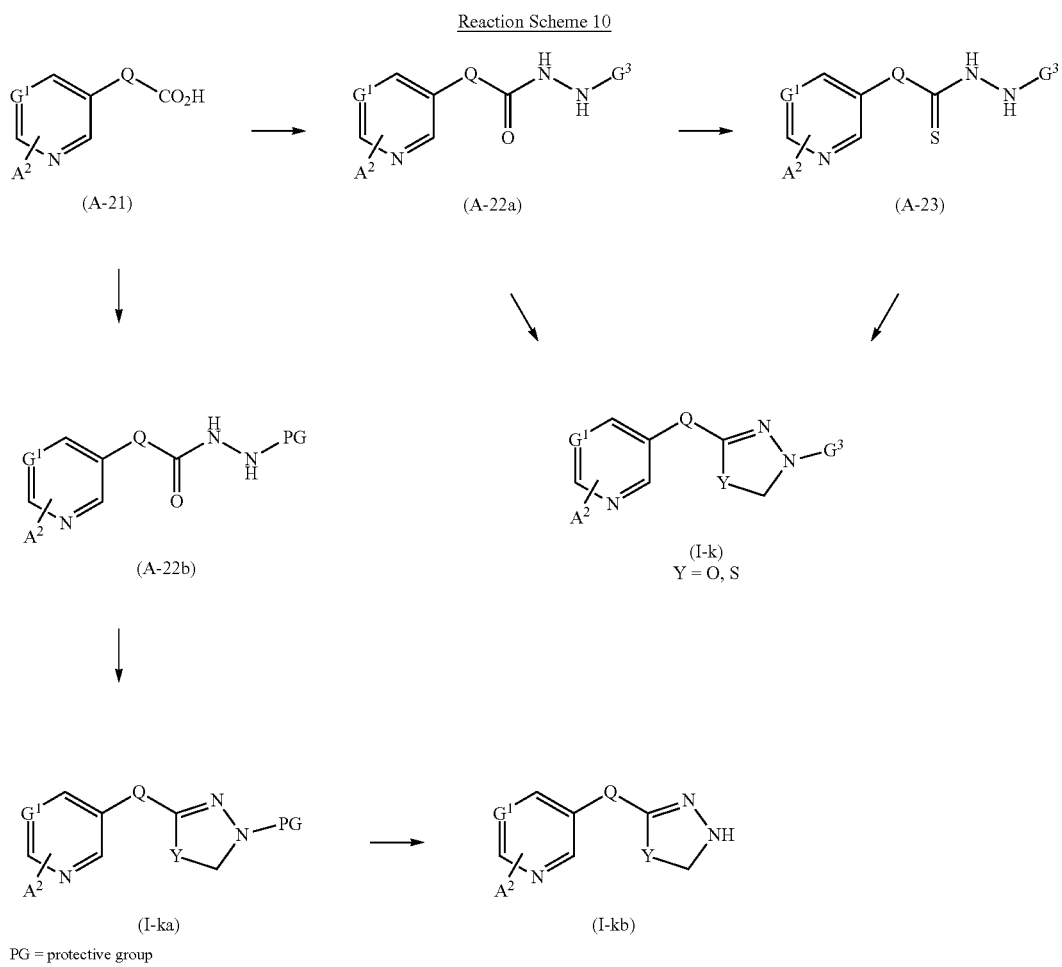

PG = protective group

To prepare the compounds (I-k) according to the invention, the heterocyclic carboxylic acids of the formula (A-21) can be converted by known activation methods into the corresponding G³-substituted or N-protective group-substituted carboxylic acid hydrazides of the formula (A-22a) or (A-22b) (PG=protective group), which can then be cyclized with formaldehyde with formation of 2,3-dihydro-1,3,4-oxazole derivatives (Y=O) (cf. G. M. Rosen et al., *J. Heterocycl. Chem.* 1975, 12, 619-622). In the case of the N-protective group-substituted 2,3-dihydro-1,3,4-oxazole derivatives (I-ka), after removal of the protective group (PG), (I-kb) can be N-derivatized. In an analogous manner, $G^3$-substituted thiocarboxylic acid hydrazides can cyclize in the presence of formaldehyde to give 2,3-dihydro-1,3,4-thiadiazole derivatives (Y=S) (cf. D. M. Evans et al., *J. Chem. Soc., Perkin Trans. 1: Organic and Bio-Organic Chem.* (1972-1999) 1986, 8, 1499-1505).

Suitable for use as activating reagents are all reagents suitable for forming an amide or hydrazide bond (cf., for example, Houben-Weyl, Methoden der organischen Chemie [Methods of Organic Chemistry], Volume 15/2; Bodansky et al., Peptide Synthesis $2^{nd}$ ed. (Wiley & Sons, New York 1976) or Gross, Meienhofer, The Peptides: Analysis, Synthesis, Biology (Academy Press, New York 1979). Coupling with phosphonium reagents, such as bis(2-oxo-3-oxazolidinyl)-phosphonium acid chloride (BOP-Cl), benzotriazol-1-yl-oxy-tris(dimethylamino-phosphonium) hexafluorophosphate (BOP), benzotriazol-1-yl-tris-pyrrolidino-phosphonium hexafluorophosphate (PyBOB®), bromo-tris-pyrrolidino-phosphonium hexafluorophosphate (PyBroP®), or with phosphonic acid ester reagents, such as diethyl cyanophosphonate (DEPC) or diphenylphosphoryl azide (DPPA), is preferred.

A preferred activating agent for the carboxylic acids of the formula (A-21) is, for example, N-(3-dimethylaminopropyl)-N'-ethylcarbodiimide.

Alternatively, activation may also be by acid halide formation using generally known methods.

To prepare compounds of the formula (A-22b), as suitable protective groups (PG) for amino groups, use may be made, for example, of substituted carbamates, amides, N-alkylamines, N-arylamines, imine derivatives, enamine derivatives, N-sulfenyl derivatives, N-sulfonyl derivatives or N-diarylphosphinyl derivatives (cf. Greene T. W., Wuts P. G. W. in Protective Groups in Organic Synthesis; John Wiley & Sons, Inc. 1999, "Protection for the Amino Group", p. 494).

Preference is given to using protective groups of the carbamate type.

In general, for deblocking protective groups, it is possible to use suitable acidic or basic reaction auxiliaries, according to procedures known from the literature. When protective groups of the carbamate type are used for amino groups, preference is given to using acidic reaction auxiliaries. When the t-butylcarbamate protective group (BOC group) is employed, for example, mixtures of mineral acids such as hydrochloric acid, hydrobromic acid, nitric acid, sulfuric acid, phosphoric acid or organic acids such as benzoic acid, formic acid, acetic acid, trifluoroacetic acid, methanesulfonic acid, benzenesulfonic acid or toluenesulfonic acid and a suitable diluent such as water and/or an organic solvent such as tetrahydrofuran, dioxane, dichloromethane, chloroform, ethyl acetate, ethanol or methanol are used. Preference is given to mixtures of hydrochloric acid or acetic acid with water and/or an organic solvent such as ethyl acetate.

Some of the compounds of the formula (A-21) are known, and/or they can be obtained by known preparation processes. Q-1: 5-(3-pyridinyl)-2-furancarboxylic acid (U.S. Pat. No. 3,927,008); Q-4: 5-(3-pyridinyl)-2-thiophenecarboxylic acid (WO 2004/013130); Q-11: 1-methyl-5-(3-pyridinyl)-1H-pyrrole-2-carboxylic acid (G. B. D. De Graaff et al., Rec. Travaux Chim. Des Pay-Bas 1964, 83, 910-918); Q-13: 5-(3-pyridinyl)-2-oxazolecarboxylic acid lithium salt (1:1) (WO 2005/061510); Q-18: 5-(3-pyridinyl)-2-thiazolecarboxylic acid lithium salt (1:1) (N. Haginoya et al., *Bioorg. Med. Chem.* 2004, 12, 5579-5586); Q-21: 3-(3-pyridinyl)-5-isothiazolecarboxylic acid (WO 2006/104141); Q-23: 1-(3-pyridinyl)-1H-imidazole-4-carboxylic acid (DE 3824658); Q-28: 4-methyl-2-(3-pyridinyl)-1H-imidazolecarboxylic acid (J. C. Yoburn, S. Baskaran, *Org. Lett.* 2005, 7, 3801-3803) and Q-38: 1-(3-pyridinyl)-1H-1,2,3-triazole-4-carboxylic acid (US 2010/160323).

Compounds of the general formula (I) in which Q represents Q-1, Q-2, Q-3, Q-4, Q-5, Q-6, Q-7, Q-8, Q-9, Q-10, Q-11, Q-12, Q-13, Q-14, Q-15, Q-16, Q-17, Q-18, Q-19, Q-20, Q-21, Q-22, Q-23, Q-24, Q-25, Q-27, Q-28, Q-30, Q-31, Q-33, Q-34, Q-35, Q-36, Q-37, Q-38, Q-39, Q-40, Q-44, Q-45, Q-46, Q-48 or Q-49 and the radical $G^2$ represents $G^2$-14 or $G^2$-15 can be prepared, for example according to Reaction Scheme 11.

Reaction Scheme 11

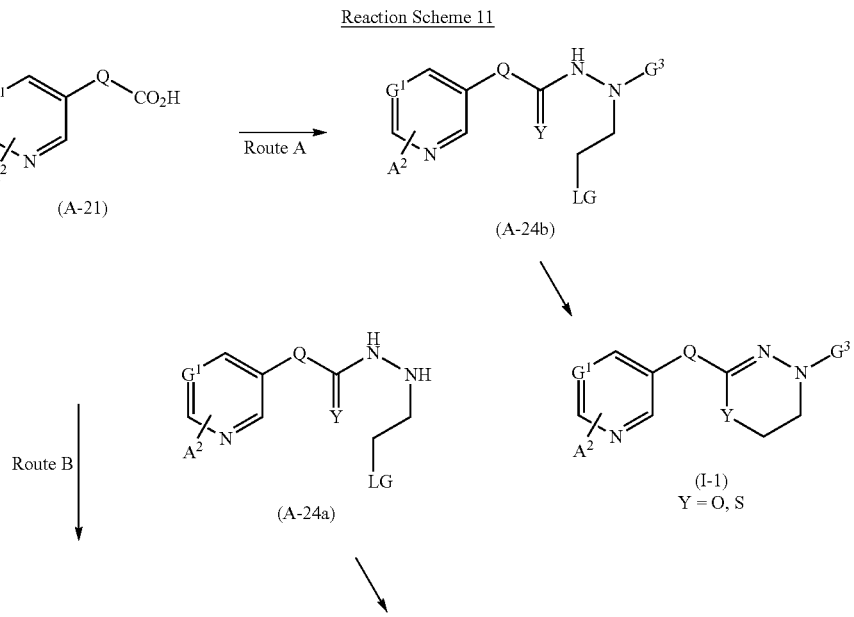

-continued

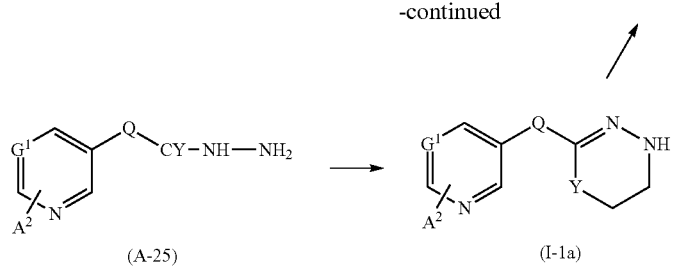

(A-25)

(I-1a)

LG = leaving group

To prepare the compounds of the formula (I-1) according to the invention, the heterocyclic carboxylic acids of the formula (A-21) can be converted by known methods into corresponding $G^3$-substituted N-2-LG-ethylcarboxylic acid hydrazides (Y=O) of the formula (A-24a) or (A-24b) which can then be cyclized with formation of 2,3-dihydro-1,3,4-oxazole derivatives (Y=O) (Route A). The leaving groups (LG) mentioned may be, for example, halogens (X=Cl, Br, I) or an activated hydroxyl group (for example O—$SO_2CF_3$, O—$SO_2CH_3$).

Alternatively (Route B), the carboxylic acids of the formula (A-21) can also initially be converted into the carboxylic acid hydrazides of the formula (A-25) (Y=O) which are then cyclized in the presence of suitable alkyl-bis-halo compounds, for example 1-bromo-2-fluoroethane (cf. U.S. Pat. No. 5,536,720) to give 2-substituted 4H-1,3,4-oxadiazines (Y=O) of the formula (I-Ia). The $G^3$-substituted 4H-1,3,4-thiadiazines (Y=S) of the formula (I-1) can be obtained in a corresponding manner.

Some of the compounds of the formula (A-21) are known, and/or they can be obtained by the preparation processes described above.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

It is furthermore possible to control protozoa, such as *Eimeria.*

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus* arundinis, *Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare, Oniscus asellus* and *Porcellio scaber.*

From the order of the Isoptera, for example, *Reticulitermes* spp. and *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp. and *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni* and *Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

The compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). They can also be used as intermediates or precursors for the synthesis of further active compounds.

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, i.e. liquid solvents, and/or solid carriers, optionally with the use of surfactants, i.e. emulsifiers and/or dispersants, and/or foam formers. The formulations are produced either in suitable plants or else before or during application.

Suitable for use as auxiliaries are substances which are suitable for imparting to the composition itself and/or to preparations derived therefrom (for example spray liquors, seed dressings) particular properties, such as certain technical properties and/or else particular biological properties. Typical auxiliaries include: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulfoxide, and also water.

Suitable Solid Carriers are:

for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulfates, alkyl- or arylsulfonates and alkyl or aryl phosphates or the corresponding PO-ether adducts. Furthermore, suitable oligomers or polymers, for example those derived from vinylic monomers, from acrylic acid, from EO and/or PO alone or in combination with, for example, (poly)alcohols or (poly)amines. It is also possible to use lignin and its sulfonic acid derivatives, unmodified and modified celluloses, aromatic and/or aliphatic sulfonic acids and also their adducts with formaldehyde.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The formulations generally comprise between 0.01 and 98% by weight of active compound, preferably between 0.5 and 90%.

The active compounds according to the invention may be used as such or in formulations thereof, including in a mixture with one or more suitable fungicides, bactericides, acaricides, nematicides, insecticides, microbicides, fertilizers, attractants, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. Furthermore, active compound combinations of this kind can improve plant growth, increase tolerance to high or low temperatures, to drought or to increased levels of water and/or soil salinity, improve flowering performance, facilitate harvesting and increase yields, accelerate ripening, increase the quality and/or nutritional value of the harvested products, prolong storage life and/or improve the processibility of the harvested products. In general, by combining the active compounds according to the invention and mixing partners, synergistic effects are obtained, i.e. the efficacy of the mixture in question is greater than the efficacy of the individual components. Generally, the combinations can be used either as seed treatments or in premixes, tankmixes or readymixes.

Particularly favourable mixing partners are, for example, the following:

Insecticides/Acaricides/Nematicides:

The active compounds identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists such as, for example, organochlorines, for example chlordane and endosulfan (alpha-); or fiproles (phenylpyrazoles), for example ethiprole, fipronil, pyrafluprole and pyriprole.

(3) Sodium channel modulators/voltage-dependent sodium channel blockers such as, for example, pyrethroids, for example acrinathrin, allethrin (d-cis-trans, d-trans), bifenthrin, bioallethrin, bioallethrin-S-cyclopentenyl, bioresmethrin, cyprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or DDT; or methoxychlor.

(4) Nicotinergic acetylcholine receptor agonists, such as, for example, neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists) such as, for example, spinosyns, for example spinetoram and spinosad.

(6) Chloride channel activators such as, for example, avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active compounds with unknown or nonspecific mechanisms of action, for example fumigants, for example methyl bromide and other alkyl halides; or chloropicrin; sulfuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, such as, for example, *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, such as, for example, diafenthiuron; or organotin compounds, for example azocyclotin, cyhexatin, fenbutatin oxide; or propargite; tetradifon.

(13) Oxidative phoshorylation decouplers acting by interrupting the H proton gradient such as, for example, chlorfenapyr and DNOC.

(14) Nicotinergic acetylcholine receptor antagonists such as, for example, bensultap, cartap (hydrochloride), thiocyclam, and thiosultap (sodium).

(15) Chitin biosynthesis inhibitors, type 0, such as, for example, benzoylureas, for example bistrifluoron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, such as, for example, buprofezin.

(17) Moulting disruptors, such as, for example, cyromazine.

(18) Ecdysone agonists/disruptors such as, for example, diacylhydrazines, for example chromafenozide, halofenozide, methoxyfenozide and tebufenozide.

(19) Octopaminergic agonists such as, for example, amitraz.

(20) Complex-III electron transport inhibitors such as, for example, hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or rotenone (Derris).

(22) Voltage-dependent sodium channel blockers, for example indoxacarb; metaflumizone.

(23) Inhibitors of acetyl-CoA carboxylase such as, for example, tetronic acid derivatives, for example spirodiclofen and spiromesifen; or tetramic acid derivatives, for example spirotetramat.

(24) Complex-IV electron transport inhibitors such as, for example, phosphines, for example aluminium phosphide, calcium phosphide, phosphine, zinc phosphide; or cyanide.

(25) Complex-II electron transport inhibitors such as, for example, cyenopyrafen.

(28) Ryanodine receptor effectors such as, for example, diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

Further active compounds with unknown mechanism of action such as, for example, azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulfonyl]-1,3-thiazole), flufenerim, pyridalyl and pyrifluquinazon; and also products based on *Bacillus firmus* (1-1582, BioNeem, Votivo) and the following known active compounds:

4-{[(6-bromopyrid-3-yl)methyl](2-fluoroethyl)amino}furan-2(5H)-one (known from WO 2007/115644),
4-{[(6-fluoropyrid-3-yl)methyl](2,2-difluoroethyl)amino}furan-2(5H)-one (known from WO 2007/115644),
4-{[(2-chloro-1,3-thiazol-5-yl)methyl](2-fluoroethyl)amino}furan-2(5H)-one (known from WO 2007/115644),
4-{[(6-chloropyrid-3-yl)methyl](2-fluoroethyl)amino}furan-2(5H)-one (known from WO 2007/115644),
4-{[(6-chloropyrid-3-yl)methyl](2,2-difluoroethyl)amino}furan-2(5H)-one (known from WO 2007/115644),
4-{[(6-chloro-5-fluoropyrid-3-yl)methyl](methyl)amino}furan-2(5H)-one (known from WO 2007/115643),
4-{[(5,6-dichloropyrid-3-yl)methyl](2-fluoroethyl)amino}furan-2(5H)-one (known from WO 2007/115646),
4-{[(6-chloro-5-fluoropyrid-3-yl)methyl](cyclopropyl)amino}furan-2(5H)-one (known from WO 2007/115643),
4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [1-(6-chloropyridin-3-yl)ethyl](methyl)oxido-$\lambda^4$-sulfanylidenecyanamide (known from WO 2007/149134) and its diastereomers {[(1R)-1-(6-chloropyridin-3-yl)ethyl](methyl)oxido-lambda-sulfanylidene}cyanamide (A) and {[(1S)-1-(6-chloropyridin-3-yl)ethyl](methyl)oxido-lambda-sulfanylidene}cyanamide (B) (likewise known from WO 2007/149134) and sulfoxaflor (likewise known from WO 2007/149134) and its diastereomers {(R)-1-[6-(trifluoromethyl)pyridin-3-yl]ethyl}-(R)-(methyl)oxido-lambda$^4$-sulfanylidenecyanamide (A$^1$) and {(S)-1-[6-(trifluoromethyl)pyridin-3-yl]ethyl}-(S)-(methyl)oxido-lambda$^4$-sulfanylidenecyanamid (A$^2$), referred to as diastereomer group A (known from WO 2010/074747, WO 2010/074751), {(R)-1-[6-(trifluoromethyl)pyridin-3-yl]ethyl}-(S)-(methyl)oxido-lambda$^4$-sulfanylidenecyanamide (B$^1$) and {(S)-1-[6-(trifluoromethyl)pyridin-3-yl]ethyl}-(R)-(methyl)oxido-lambda$^4$-sulfanylidenecyanamide (B$^2$), referred to as diastereomer group B (likewise known from WO 2010/074747, WO 2010/074751), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulfinyl]phenyl]-3-(trifluoromethyl)-1H-1,2,4-triazole-5-amine (known from WO 2006/043635),

[(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,1H-benzo[f]pyrano[4,3-b]chromen-4-yl]methyl cyclopropanecarboxylate (known from WO 2006/129714), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazole-3-amine 1,1-dioxide (known from WO2007/057407) and N-[1-(2,3-dimethylphenyl)-2-(3,5-dimethylphenyl)ethyl]-4,5-dihydro-1,3-thiazole-2-amine (known from WO2008/104503).

In a preferred embodiment of the invention, a penetrant is additionally added to the crop protection compositions to enhance the action. Suitable penetrants also include, for example, substances which promote the availability of the compounds of the formula (I) in the spray coating. These include, for example, mineral and vegetable oils. Suitable oils are all mineral or vegetable oils—modified or otherwise—which can usually be used in agrochemical compositions. By way of example, mention may be made of sunflower oil, rapeseed oil, olive oil, castor oil, colza oil, corn seed oil, cottonseed oil and soybean oil or the esters of said oils. Preference is given to rapeseed oil, sunflower oil and their methyl or ethyl esters, especially rapeseed oil methyl ester.

The concentration of penetrant in the compositions of the invention can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentrations are generally between 0.1 and 10 g/l, preferably between 0.5 and 5 g/l.

When used as insecticides, the active compounds according to the invention may also be present in their commercially available formulations and in the use forms, prepared from these formulations, as a mixture with synergists. Synergists are compounds which enhance the action of the active compounds, without any need for the synergist added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations may vary within wide limits. The active compound concentration of the application forms may be from 0.00000001 to 95% by weight of active compound, preferably between 0.00001 and 1% by weight.

The compounds are employed in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants can thus be plants which can be obtained by conventional breeding and optimization methods or by biotechnological and genetic engineering methods or combinations of these methods, including the transgenic plants and including the plant varieties which can or cannot be protected by varietal property rights. Examples which may be mentioned are the important crop plants, such as cereals (wheat, rice), maize, soya beans, potatoes, sugar beet, tomatoes, peas and other vegetable species, cotton, tobacco, oilseed rape and also fruit plants (with the fruits apples, pears, citrus fruits and grapes). Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and vegetative and generative propagation material, for example cuttings, tubers, rhizomes, slips and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are to be understood as meaning plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, increased flowering performance, easier harvesting, accelerated ripening, higher yields, higher quality and/or higher nutrient value of the harvested products, increased storage life and/or processibility of the harvested products, which exceed the effects normally to be expected.

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other types of vegetable, cotton, tobacco, oilseed rape and also fruit plants (with the fruits apples, pears, citrus fruits and grapes), with particular emphasis being given to maize, soya beans, potatoes, cotton, tobacco and oilseed rape. Traits that are emphasized in particular are increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal compounds, for example imidazolinones, sulfonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soy bean varieties which are sold under the trade names Roundup Ready® (tolerance against glyphosate, for example maize, cotton, soya beans), Liberty Link® (tolerance against phosphinothricin, for example oilseed rape), IMI® (tolerance against imidazolinones) and STS® (tolerance against sulfonylurea, for example maize). Herbicide-resistant plants (plants bred in a conventional manner for herbicide tolerance) which may be mentioned include the varieties sold under the name Clearfield® (for example maize). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula (I) and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp. (*Ctenocephalides canis, Ctenocephalides felis*), *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals such as, for example, dogs, cats, caged birds, aquarium fish, and experimental animals, for example hamsters, guinea pigs, rats and mice. The control of these arthropods is intended to reduce cases of death and reduced productivity (of meat, milk, wool, hides, eggs, honey etc.), and so more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of 1 to 80% by weight, either directly or after 100 to 10 000-fold dilution, or they may be used as a chemical bath.

It has also been found that the compounds according to the invention have strong insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;* dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensisi Zootermopsis nevadensis, Coptotermes formosanus;* bristletails, such as *Lepisma saccharina.*

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional partners for mixing, reference is made to the insecticides and fungicides mentioned above.

Moreover, the compounds according to the invention can be employed for protecting objects which come into contact with saltwater or brackish water, in particular hulls, screens, nets, buildings, moorings and signalling systems, against fouling.

Furthermore, the compounds according to the invention can be used alone or in combinations with other active compounds as antifouling compositions.

The active compounds are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active compounds and auxiliaries in domestic insecticide products. They are effective against sensitive and resistant species, and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

Example A

2-Bromo-6-[3-(pyridin-3-yl)-1,2-oxazol-5-yl]pyridine

Step 1: 1-(6-Bromopyridin-2-yl)-3-(pyridin-3-yl)propane-1,3-dione

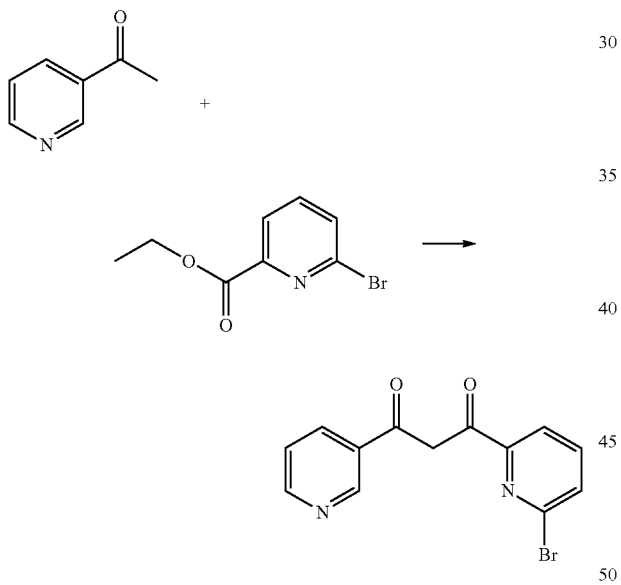

3.71 g (33.0 mmol) of potassium tert-butoxide were added to a mixture of 4.00 g (33.0 mmol) of 3-acetopyridine and 7.60 g (33.0 mmol) of ethyl 6-bromo-2-pyridinecarboxylate in 100 ml of tetrahydrofuran. The solution was stirred at room temperature until a solid mixture has formed. 100 ml of water and 10 ml of acetic acid were then added, and the aqueous phase was subsequently extracted with dichloromethane. The combined organic phases were dried over magnesium sulfate, and the solvent was then removed under reduced pressure. The residue that remained was purified chromatographically (mobile phase: cyclohexane/ethyl acetate), the solid was then washed with diethyl ether. This gave 6.91 g (69% of theory) of 1-(6-bromopyridin-2-yl)-3-(pyridin-3-yl)propane-1,3-dione.

Mass (m/z) 305.0; 307.0 (M+H)$^+$ $^1$H-NMR (d$_6$-DMSO): 4.8; 7.41; 7.57-7.61; 7.86-7.89; 7.94-8.01; 8.15-8.17; 8.32-8.39; 8.80-8.81; 9.16-9.19 ppm. (Some of the compound is present in the enol form).

Step 2: 2-Bromo-6-[3-(pyridin-3-yl)-1,2-oxazol-5-yl]pyridine

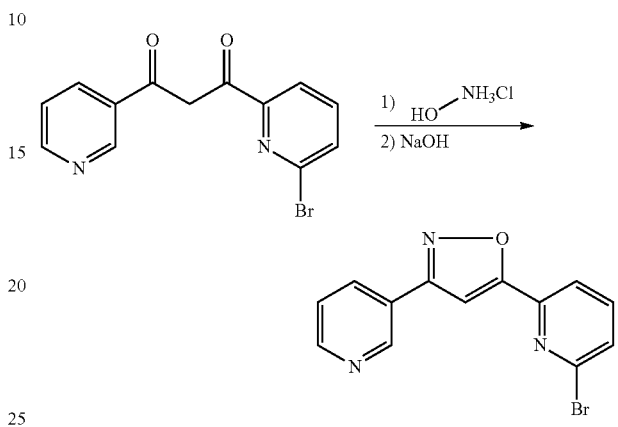

A mixture of 1.10 g (3.61 mmol) of 1-(6-bromopyridin-2-yl)-3-(pyridin-3-yl)propane-1,3-dione, 0.75 g (10.8 mmol) of hydroxylamine hydrochloride and 20 ml of methanol was stirred at reflux temperature for 90 minutes. The reaction mixture was then cooled to room temperature and the solvent was removed under reduced pressure on a rotary evaporator. The residue that remained was stirred in 20 ml of 10% strength aqueous sodium hydroxide solution at reflux temperature for one hour. The reaction mixture was then cooled, and the solid was filtered off and purified by HPLC. This gave 264 mg (24% of theory) of 2-bromo-6-[3-(pyridin-3-yl)-1,2-oxazol-5-yl]pyridine.

HPLC-MS: log P (HCOOH)=2.23; mass (m/z): 302.0 (M+H)$^+$;

$^1$H-NMR (d$_6$-DMSO): 7.58-7.61 (m, 1H), 7.82-7.84 (m, 1H), 7.90 (s, 1H), 7.99-8.02 (m, 1H), 8.06-8.08 (m, 1H), 8.38-8.41 (m, 1H), 8.73-8.74 (m, 1H), 9.20-9.21 ppm (m, 1H).

Example B

2-{6-[1-Methyl-5-(pyridin-3-yl)-1H-pyrazol-3-yl]pyridin-2-yl}pyrimidine

Step 1: 2-Bromo-6-[1-methyl-5-(pyridin-3-yl)-1H-pyrazol-3-yl]pyridine

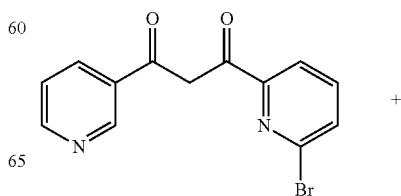

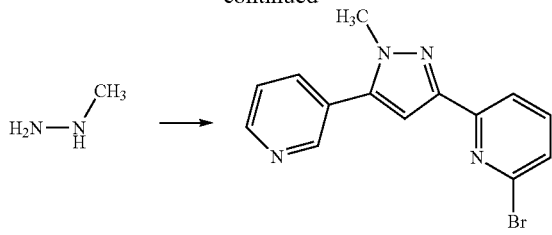

4.00 g (13.1 mmol) of 1-(6-bromopyridin-2-yl)-3-(pyridin-3-yl)propane-1,3-dione were initially charged in 100 ml of methanol, and the mixture was heated. 1.69 g (36.7 mmol) of N-methylhydrazine and 2 ml of acetic acid were then added, and the reaction mixture was stirred at reflux temperature for 4 hours. The solvent was then removed under reduced pressure on a rotary evaporator, and the residue was purified by column chromatography on silica gel (mobile phase: cyclohexane/ethyl acetate). This gave 3.62 g (87% of theory) of 2-bromo-6-[1-methyl-5-(pyridin-3-yl)-1H-pyrazol-3-yl]pyridine which, according to HPLC-MS, also contained about 32% of the regioisomer.

HPLC-MS: log P (HCOOH)=1.94; mass (m/z): 315.0 (M+H)$^+$ $^1$H-NMR (d$_6$-DMSO): 3.97 (s, 3H), 7.07 (s, 1H), 7.55-7.59 (m, 2H), 7.79-7.83 (m, 1H), 7.96-7.98 (m, 1H), 8.08-8.11 (m, 1H), 8.67-8.68 (m, 1H), 8.85-8.86 ppm (m, 1H);

regioisomer: HPLC-MS: log P (HCOOH)=1.67.

Step 2: 2-{6-[1-Methyl-5-(pyridin-3-yl)-1H-pyrazol-3-yl]pyridin-2-yl}pyrimidine

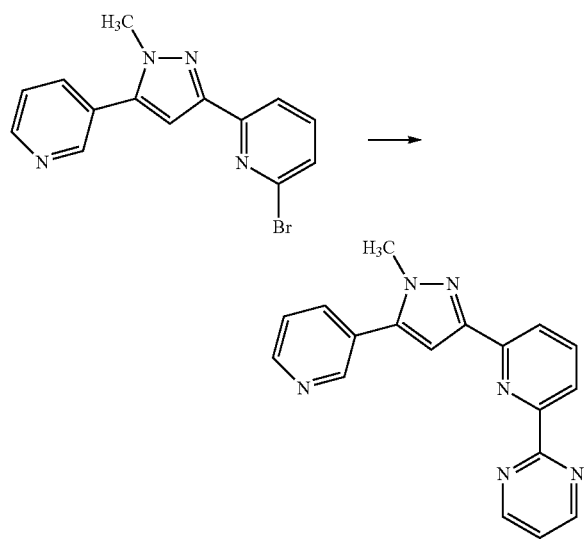

600 mg (1.90 mmol, comprising 32% of regioisomer) of 2-bromo-6-[1-methyl-5-(pyridin-3-yl)-1H-pyrazol-3-yl]pyridine, 773 mg (2.09 mmol) of 2-(tributylstannyl)pyrimidine, 6.7 mg (38 mol) of PdCl$_2$, 76 μl (76 mol, 1 M solution in toluene) of P(t-Bu)$_3$, 14.5 mg (76 mol) of CuI and 578 mg (3.81 mmol) of CsF were initially charged in 6 ml of N,N-dimethylformamide. The reaction mixture was stirred at 45° C. for 15 hours. A saturated solution of potassium fluoride was then added, and the mixture was stirred at room temperature for about 18 hours. The aqueous phase was then extracted with dichloromethane and dried over magnesium sulfate, and the solvent was removed under reduced pressure on a rotary evaporator. The residue that remained was purified on silica gel, and the regioisomers were separated by HPLC. This gave 3.62 g (87% of theory) of 2-{6-[1-methyl-5-(pyridin-3-yl)-1H-pyrazol-3-yl]pyridin-2-yl}pyrimidine.

HPLC-MS: log P (HCOOH)=1.26; mass (m/z): 315.1 (M+H)$^+$ $^1$H-NMR (d$_6$-DMSO): 4.00 (s, 3H), 7.14 (s, 1H), 7.57-7.60 (m, 2H), 8.03-8.06 (m, 1H), 8.10-8.14 (m, 2H), 8.30-8.32 (m, 1H), 8.67-8.69 (m, 1H), 8.88-8.89 (m, 1H), 9.01-9.02 ppm (m, 2H);

regioisomer: HPLC-MS: log P (HCOOH)=1.12.

Example C

2-{6-[4-(Pyridin-3-yl)-1H-imidazol-1-yl]pyridin-2-yl}pyrimidine

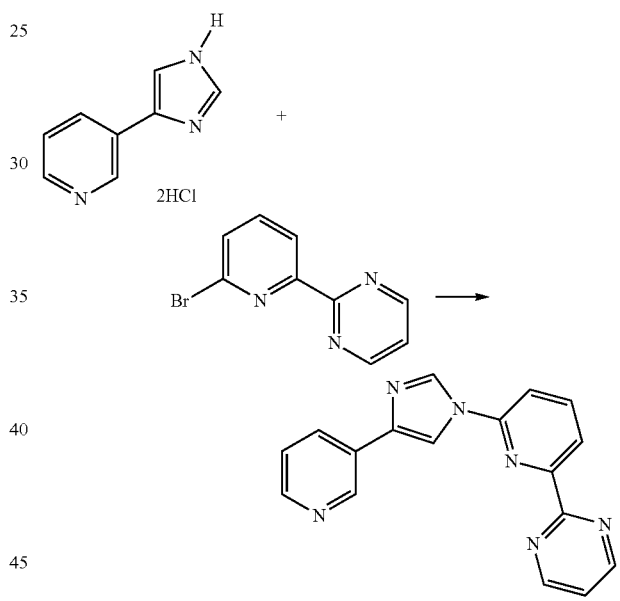

500 mg (2.29 mmol) of 3-(1H-imidazol-4-yl)pyridine dihydrochloride were initially charged in 5.4 ml of 1-methyl-2-pyrrolidone, and 951 mg (6.87 mmol) of potassium carbonate were added. The mixture was stirred at room temperature for 30 minutes. 541 mg (2.29 mmol) of 2-(6-bromopyridin-2-yl)pyrimidine (preparation cf. WO 2010/006713, *Tetrahedron Letters* 2000, 41, 1653-1656.) were then added, and the reaction mixture was stirred at 130° C. for three days. The solvent was then removed under reduced pressure on a rotary evaporator (water bath at 90° C.) and the residue was purified by column chromatography on silica gel (mobile phase: cyclohexane/ethyl acetate/methanol). This gave 140 mg (20% of theory) of 2-{6-[4-(pyridin-3-yl)-1H-imidazol-1-yl]pyridin-2-yl}pyrimidine.

HPLC-MS: log P (HCOOH)=0.75; mass (m/z): 301.2 (M+H)$^+$ $^1$H-NMR (d$_6$-DMSO): 7.44-7.47 (m, 1H), 7.62-7.64 (m, 1H), 8.02-8.04 (m, 1H), 8.24-8.28 (m, 2H), 8.39-8.41 (m, 1H), 8.48-8.49 (m, 1H), 8.66-8.67 (m, 1H), 8.73-8.74 (m, 1H), 9.05-9.06 (m, 2H), 9.12-9.13 ppm (m, 1H).

Example D

2-[3-(Pyridin-3-yl)-1H-1,2,4-triazol-1-yl]-6-(trifluoromethyl)pyridine

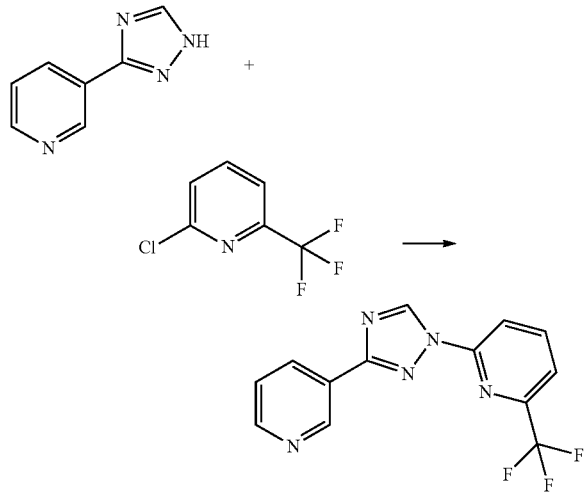

100 mg (684 µmol) of 3-(1H-1,2,4-triazol-3-yl)pyridine (preparation cf. *J. Org. Chem.* 1979, 44, 4160-4164), 124 mg (683 µmol) of 2-chloro-6-(trifluoromethyl)pyridine and 142 mg (1.03 mmol) of potassium carbonate were initially charged in 5 ml of N,N-dimethylformamide, and the mixture was stirred at 120° C. for about 18 hours. After cooling, water was added and the mixture was extracted three times with ethyl acetate. The organic phases were washed with saturated sodium chloride solution, dried over sodium sulfate, filtered and concentrated. This gave 180 mg (90% of theory) of 2-[3-(pyridin-3-yl)-1H-1,2,4-triazol-1-yl]-6-(trifluoromethyl)pyridine as a white solid.

HPLC-MS: log P=2.11; mass (m/z) 292.1 (M+H)+

$^1$H-NMR (d$_6$-DMSO) 7.59 (ddd, 1H), 8.02 (d, 1H), 8.29 (d, 1H), 8.42 (t, 1H), 8.47 (dt, 1H), 8.72 (dd, 1H), 9.32 ppm (dd, 1H).

Example E

2-{6-[2-(Pyridin-3-yl)-1,3-oxazol-5-yl]pyridin-2-yl}pyrimidine

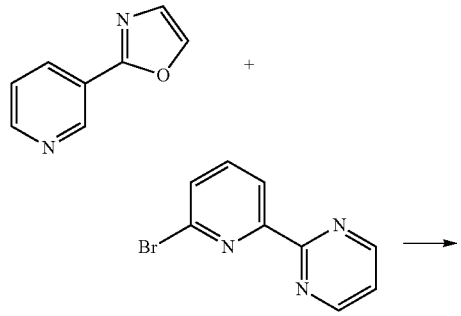

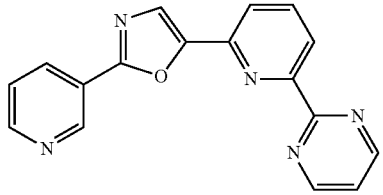

Under argon, 130 mg (0.88 mmol) of 2-(3-pyridinyl)oxazole (*Hel. Chim. Acta* 1962, 42, 375-381), 175 mg (0.74 mmol) of 2-(6-bromo-2-pyridyl)pyrimidine, 11 mg (0.02 mmol) of [(t-Bu)$_2$P(OH)]$_2$PdCl$_2$ (POPd) and 205 mg (1.48 mmol) of potassium carbonate were initially charged in 5 ml of N,N-dimethylformamide, and the mixture was stirred at 120° C. for 16 hours. For work-up, the reaction mixture was concentrated under reduced pressure and the crude product that remained was purified by chromatography on silica gel (mobile phase: dichloromethane/methanol). This gave 126 mg (54% of theory) of 2-{6-[2-(pyridin-3-yl)-1,3-oxazol-5-yl]pyridin-2-yl}pyrimidine.

HPLC-MS: log P=1.39; mass (m/z): 302.1 (M+H)+

$^1$H-NMR (400 MHz, d$_6$-DMSO) 7.62 (m, 2H), 8.08 (m, 1H), 8.15 (m, 2H), 8.39 (m, 1H), 8.50 (m, 1H), 8.79 (m, 1H), 9.04 (m, 2H), 9.32 ppm (m, 1H).

Example F

2-{6-[4-(Pyridin-3-yl)-1H-pyrazol-1-yl]pyridin-2-yl}pyrimidine

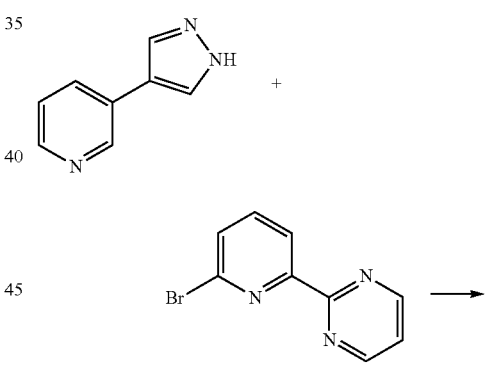

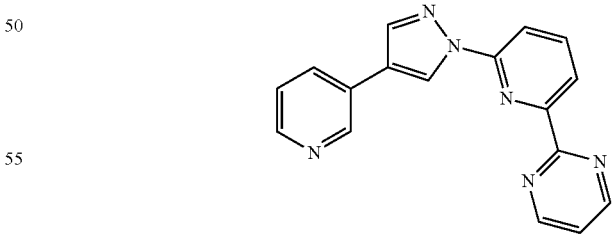

DMF was added to 0.8 g (5.5 mmol) of 3-(1H-pyrazol-4-yl)pyridine (*Angew. Chemie*, 2006, 118 (8) 1304), 1.3 g (5.5 mmol) of 2-(6-bromopyridin-2-yl)pyrimidine (WO 2010/006713), 0.29 g (0.82 mmol) of copper-8-hydroxyquinoline complex (cf. *Tetrahedron Lett*, 2006, 149) and 2.28 g (16.5 mmol) of potassium carbonate, and the mixture was stirred at 120° C. under argon for 16 hours. The entire reaction mixture was then concentrated under reduced pressure. The residue was admixed with aqueous citric acid, aqueous sodium chloride, ethyl acetate and diluted aqueous sodium hydroxide solution until the mixture gave an alkaline reaction (pH=9), the mixture was extracted four times with ethyl acetate and the combined organic phases were dried with sodium sulfate and concentrated under reduced pressure. The residue was purified by chromatography on silica gel (mobile phase: cyclohexane/acetone). This gave 0.56 g (32% of theory) of 2-{6-[4-(pyridin-3-yl)-1H-pyrazol-1-yl]pyridin-2-yl}pyrimidine.

HPLC-MS: log P=1.04; mass (m/z): 301.1 (M+H)$^+$ $^1$H-NMR (400 MHz, d6-DMSO) 7.45 (1H), 7.6 (m, 1H), 8.1-8.2 (m, 3H), 8.35 (m, 2H), 8.5 (m, 1H), 9.05 (m, 3H), 9.15 (s, 1H)

Example G

2-{6-[1-(Pyridin-3-yl)-1H-1,2,3-triazol-4-yl]pyridin-2-yl}pyrimidine

Step 1: 2-{6-[(Trimethylsilyl)ethynyl]pyridin-2-yl}pyrimidine

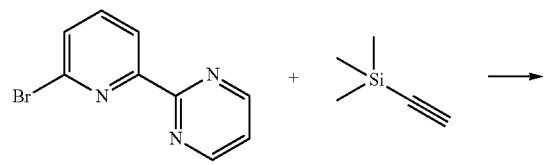

1.00 g (3.99 mmol) of 2-(6-bromopyridin-2-yl)pyrimidine, 45.5 mg (239 μmol) of copper(I) iodide and 670 μl (4.78 mmol) of N-isopropylpropane-2-amine were initially charged in 15 ml of tetrahydrofuran and degassed in an ultrasonic bath under argon. The reaction mixture was then heated to 50° C., 168 mg (239 mol) of dichloro[bis(triphenylphosphoranyl)]palladium were added and 1.70 ml (12.0 mmol) of ethynyl(trimethyl)silane were added dropwise over a period of one hour. The mixture was then stirred at 60° C. for a further two hours. For work-up, the mixture was added to semiconcentrated sodium chloride solution, the mixture was filtered through Celite and the aqueous phase was extracted repeatedly with ethyl acetate. The combined organic phases were dried over magnesium sulfate, filtered, concentrated and purified chromatographically. This gave 520 mg (51% of theory) of 2-{6-[(trimethylsilyl)ethynyl]pyridin-2-yl}pyrimidine.

HPLC-MS: log P=3.11; mass (m/z) 254.1 (M+H)$^+$ $^1$H-NMR (d$_6$-DMSO) 0.29 (s, 9H), 7.59 (t, 1H), 7.67 (dd, 1H), 8.00 (t, 1H), 8.37 (dd, 1H), 8.99 ppm (d, 2H).

Step 2: 2-(6-Ethynylpyridin-2-yl)pyrimidine

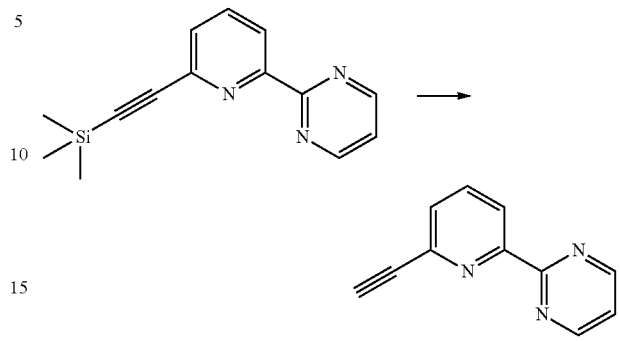

Under argon, 500 mg (1.97 mmol) of 2-{6-[(trimethylsilyl)ethynyl]pyridin-2-yl}pyrimidine were initially charged in 20 ml of tetrahydrofuran at −5° C., 2.37 ml (2.37 mmol) of a 1 M solution of N,N,N-tributylbutane-1-ammonium fluoride in tetrahydrofuran were added and the mixture was stirred at this temperature for 2 hours. For work-up, the reaction mixture was filtered through silica gel (ethyl acetate), concentrated under reduced pressure and purified chromatographically. This gave 311 mg (87% of theory) of 2-(6-ethynylpyridin-2-yl)pyrimidine.

HPLC-MS: log P=1.05; mass (m/z) 182.0 (M+H)$^+$ $^1$H-NMR (d$_6$-DMSO) 4.40 (s, 1H), 7.59 (t, 1H), 7.71 (dd, 1H), 8.02 (t, 1H), 8.38 (d, 1H), 8.99 (d, 2H) ppm.

Step 3: 2-{6-[1-(Pyridin-3-yl)-1H-1,2,3-triazol-4-yl]pyridin-2-yl}pyrimidine

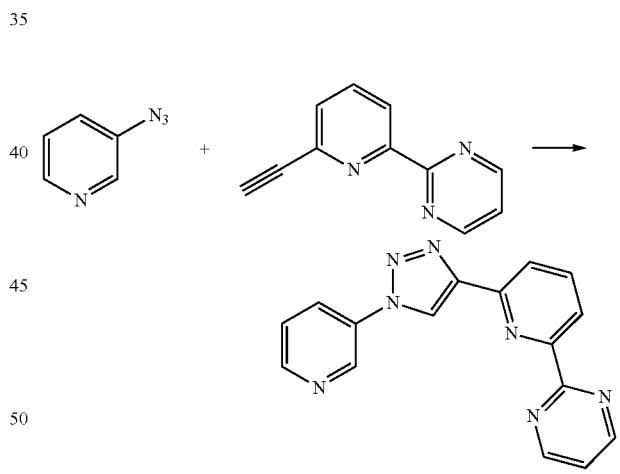

100 mg (833 μmol) of 3-azidopyridine (for preparation see U.S. Pat. No. 4,775,762, CAUTION explosive!) and 151 mg (833 μmol) of 2-(6-ethynylpyridin-2-yl)pyrimidine were initially charged in a mixture of 1 ml of water and 1 ml of tert-butanol, 16.5 mg (83.3 μmol) of the sodium salt of L-ascorbic acid and 20.8 mg (83.3 μmol) of copper(II) sulfate pentahydrate were added, and the mixture was stirred at room temperature for 23 hours. The reaction mixture was then added to water and extracted repeatedly with dichloromethane. The separated organic phases were then dried over magnesium sulfate, filtered and concentrated. Chromatographic purification gave 26.0 mg (10% of theory) of 2-{6-[1-(pyridin-3-yl)-1H-1,2,3-triazol-4-yl]pyridin-2-yl}pyrimidine.

HPLC-MS: log P=1.39; mass (m/z): 302.0 (M+H)+
1H-NMR (d6-DMSO) 7.61 (t, 1H), 7.69 (dd, 1H), 8.16 (t, 1H), 8.29 (d, 1H), 8.38 (d, 1H), 8.51 (m, 1H), 8.73 (dd, 1H), 9.03 (d, 2H), 9.31 (d, 1H), 9.44 (s, 1H) ppm.

Example H

2-{6-[5-(Pyridin-3-yl)-3-furyl]pyridin-2-yl}pyrimidine

Step 1: 3-[4-(4,4,5,5-Tetramethyl-1,3,2-dioxaborolan-2-yl)-2-furyl]pyridine

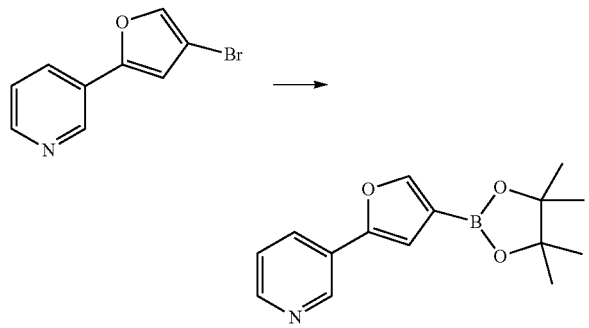

Under argon, 1.25 g (4.91 mmol) of 4,4,4',4',5,5,5',5'-octamethyl-2,2'-bi-1,3,2-dioxaborolane, 1.31 g (13.4 mmol) of potassium acetate, 182 mg (223 mol) of 1,1'-bis(diphenylphosphino)-ferrocene]dichloropalladium(II) and 80 ml of dioxane were added to 1.00 g (4.46 mmol) of 3-(4-bromo-2-furyl)pyridine (preparation cf. WO 2005/005435 A1) in a flask which had been dried by heating, and the mixture was stirred at 100° C. for four hours and then at room temperature overnight. The reaction mixture was filtered through a glass frit filled with silica gel, the filtercake was washed with cyclohexane/ethyl acetate and the filtrate was concentrated under reduced pressure on a rotary evaporator. Chromatographic purification gave 757 mg (63% of theory) of 3-[4-(4,4,5,5-tetramethyl-1,3,2-dioxaborolan-2-yl)-2-furyl]pyridine.

HPLC-MS: log P=2.25; mass (m/z) 272.2 (M+H)+
1H-NMR (d6-DMSO) 1.29 (s, 12H), 7.20 (s, 1H), 7.45 (dd, 1H), 8.07 (s, 1H), 8.10 (m, 1H), 8.49 (dd, 1H), 8.96 (d, 1H) ppm.

Step 1: 2-{6-[5-(Pyridin-3-yl)-3-furyl]pyridin-2-yl}pyrimidine

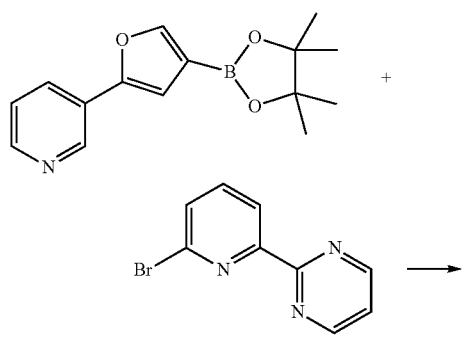

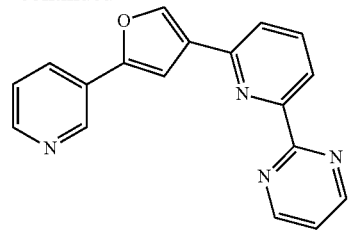

400 mg (1.38 mmol) of 3-[4-(4,4,5,5-tetramethyl-1,3,2-dioxaborolan-2-yl)-2-furyl]pyridine and 347 mg (1.38 mmol) of 2-(6-bromopyridin-2-yl)pyrimidine were initially charged in 20 ml of dioxane, and 3.46 ml of a 2 molar aqueous sodium carbonate solution were added. The reaction mixture was degassed in an ultrasonic bath under argon and then heated to reflux temperature, and, at 80° C., 48.0 mg (42.0 µmol) of tetrakis(triphenylphosphine)palladium(0) were added. The reaction mixture was stirred under reflux for 8 hours and then at room temperature overnight. The mixture was then poured into 100 ml of water and extracted with dichloromethane. The light-yellow organic phases were combined, washed with 100 ml of water and then dried over MgSO4. The mixture was then filtered and concentrated under reduced pressure on a rotary evaporator. Chromatographic purification gave 206 mg (50% of theory) of 2-{6-[5-(pyridin-3-yl)-3-furyl]pyridin-2-yl}pyrimidine.

HPLC-MS: log P=1.26; mass (m/z) 301.2 (M+H)+
1H-NMR (d6-DMSO) 7.51 (ddd, 1H), 7.61 (t, 1H), 7.77 (s, 1H), 7.94 (dd, 1H), 8.06 (t, 1H), 8.19 (m, 1H), 8.28 (dd, 1H), 8.55 (dd, 1H), 8.57 (d, 1H), 9.03 (s, 1H), 9.04 (s, 1H), 9.05 (dd, 1H) ppm.

Example I

2-{6-[3-(Pyridin-3-yl)-1H-pyrazol-1-yl]pyridin-2-yl}pyrimidine

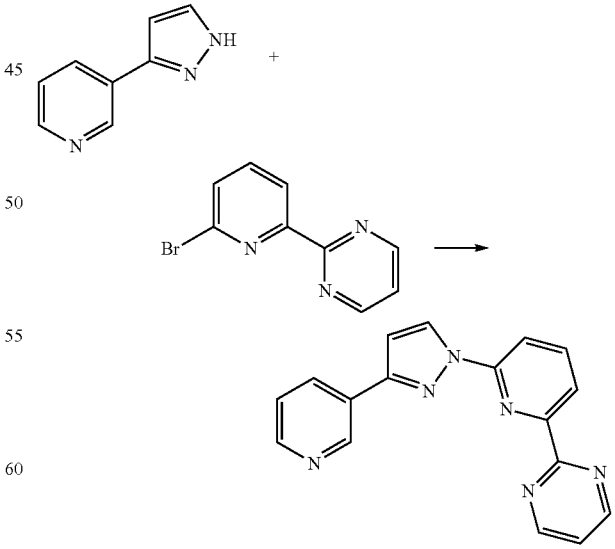

10 ml of DMF were added to 515.5 mg (3.55 mmol) of 3-(1H-pyrazol-3-yl)pyridine (preparation cf. WO 94/29300 A1), 838.5 mg (3.55 mmol) of 2-(6-bromopyridin-2-yl)pyrimidine (WO 2010/006713), 28.2 mg (0.35 mmol) of copper (II) oxide, 2.31 g (7.10 mmol) of cesium carbonate and 276.3 mg (1.06 mmol) of iron(III) acetylacetonate, and the mixture was stirred at 90° C. for 60 hours. The entire reaction mixture was then cooled to room temperature, and water was added. The reaction mixture was then extracted with ethyl acetate. The organic phase was separated off, dried and concentrated under reduced pressure. The residue was purified by chromatography on silica gel. This gave 334 g (31.3% of theory) of 2-{6-[3-(pyridin-3-yl)-1H-pyrazol-1-yl]pyridin-2-yl}pyrimidine.

HPLC-MS: log P=1.20; mass (m/z) 301.2 (M+H)+

$^{13}$C- with $^1$H-NMR decoupling (CPD) (d$_6$-DMSO) 113.6, 121.8, 124.1, 128.3, 133.1, 140.8, 147.1, 149.6, 150.8, 153.6 (pyridine-C), 106.4, 129.2, 150.7 (pyrazole-C), 121.5, 158.2, 158.2, 162.4 (pyrimidine-C) ppm.

Example J

5-Isopropyl-2-(pyridin-3-yl)-4-[6-(pyrimidin-2-yl)pyridin-2-yl]-2,4-dihydro-3H-1,2,4-triazol-3-one

Step 1: 4-Amino-5-ethyl-2-(pyridin-3-yl)-2,4-dihydro-3H-1,2,4-triazol-3-one

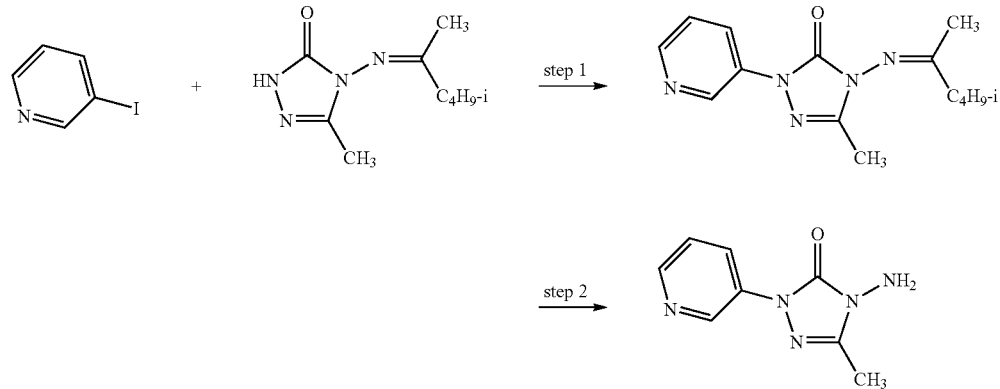

Reaction Step 1:

For 20 min, a weak stream of argon was passed through a mixture of 1.23 g (6.0 mmol) of 3-iodopyridine, 981 mg (5.0 mmol) of 5-methyl-4-[(4-methylpentan-2-ylidene)amino]-2,4-dihydro-3H-1,2,4-triazol-3-one (preparation cf. EP 511569, WO 1993/004050) and 1.037 g (7.5 mmol) of powdered potassium carbonate in 5 ml of N,N-dimethylformamide. 205 mg (1.0 mmol) of copper(I) iodide were then added, and under protective gas the mixture was heated at 150° C. for 2 hours. Analytically, by thin-layer chromatography, no more triazolinone starting material was found. With stirring, 5 ml of 25% strength ammonia solution and 10 ml of water were added to the cooled reaction mixture, which was then extracted three times in each case with 20 ml of ethyl acetate.

Reaction Step 2:

The combined organic phases were concentrated, the residue was taken up in 20 ml of ethanol and 3 ml of concentrated hydrochloric acid were added. Under slight superatmospheric pressure, the reaction mixture was concentrated slowly on a rotary evaporator. This operation (addition of ethanol and hydrochloric acid followed by concentration) was repeated three more times. The residue was then taken up in ethyl acetate and adjusted with 5% strength sodium carbonate solution to a pH of from 8 to 9. The organic phase was then separated off and the aqueous phase was extracted three more times. The combined organic phases were dried and concentrated under reduced pressure. This gave 470 mg of 4-amino-5-methyl-2-(pyridin-3-yl)-2,4-dihydro-3H-1,2,4-triazol-3-one as a colorless solid.

HPLC-MS: log P=could not be determined; mass (m/z) 192.1 (M+H)+

$^1$H-NMR (d$_6$-DMSO) 2.25 (s, 3H); 3.36 (br. s, 2H); 7.49-7.51 (m, 1H); 8.23-8.25 (m, 1H); 8.42-8.43 (m, 1H); 9.12 (m, 1H) ppm.

The following compounds were obtained in an analogous manner:

(a) 4-Amino-5-ethyl-2-(pyridin-3-yl)-2,4-dihydro-3H-1,2,4-triazol-3-one from 5-ethyl-4-[(4-methylpentan-2-ylidene)amino]-2,4-dihydro-3H-1,2,4-triazol-3-one HPLC-MS: log P=0.32; mass (m/z) 206.1 (M+H)+

$^1$H-NMR (d$_6$-DMSO) 1.22-1.25 (t, 3H); 2.62-2.66 (q, 2H); 3.3-3.6 (br. s, 2H); 7.57 (br. s, 1H); 8.27-8.28 (m, 1H); 8.4-8.65 (br. s, 1H); 9.1-9.4 (br. s) ppm.

(b) 4-Amino-5-isopropyl-2-(pyridin-3-yl)-2,4-dihydro-3H-1,2,4-triazol-3-one from 5-isopropyl-4-[(4-methylpentan-2-ylidene)amino]-2,4-dihydro-3H-1,2,4-triazol-3-one HPLC-MS: log P=0.85; mass (m/z) 220.1 (M+H)+

$^1$H-NMR (d$_6$-DMSO) 1.26-1.29 (d, 6H); 3.04-3.11 (m, 1H); 5.45 (br. s, 2H); 7.52 (br. s, 1H); 8.22-8.25 (d, 1H); 8.35-8.6 (br. s, 1H); 9.05-9.3 (br. s, 1H).

Step 2: 5-Methyl-2-(pyridin-3-yl)-2,4-dihydro-3H-1,2,4-triazol-3-one

Step 3: 5-Isopropyl-2-(pyridin-3-yl)-4-[6-(pyrimidin-2-yl)pyridin-2-yl]-2,4-dihydro-3H-1,2,4-triazol-3-one

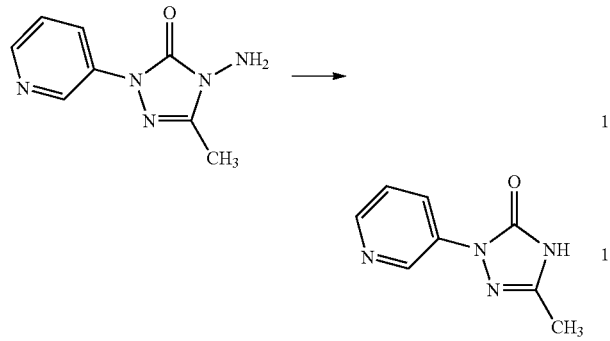

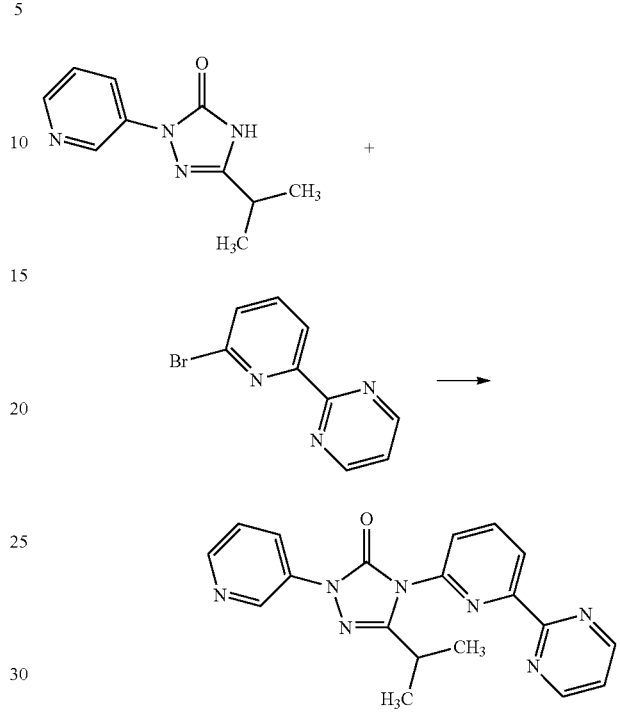

750 mg (3.923 mmol) of 4-amino-5-methyl-2-(pyridin-3-yl)-2,4-dihydro-3H-1,2,4-triazol-3-one were dissolved in a mixture of 9 ml of water and 3 ml of concentrated hydrochloric acid. At 5° C., a solution of 314 mg (4.55 mmol) of sodium nitrite in 1 ml of water was then added dropwise. The reaction mixture was then allowed to warm to room temperature and stirred for another 1 hour. The reaction mixture was neutralized using 30% strength aqueous sodium hydroxide solution and a few drops of an aqueous sodium bisulfite solution were added such that the test with potassium iodide/starch paper is negative. The mixture was extracted repeatedly with ethyl acetate, and the combined organic phases were dried with sodium sulfate and concentrated. This gave 253 mg of 5-methyl-2-(pyridin-3-yl)-2,4-dihydro-3H-1,2,4-triazol-3-one in the form of a white solid (content LC-MS: 100%) which was used for the next reaction.

HPLC-MS: log P=−0.21; mass (m/z) 177.1 (M+H)$^+$ $^1$H-NMR (d$_6$-DMSO) 2.20 (s, 3H); 7.45-7.48 (dd, 1H); 8.20-8.22 (d, 1H); 8.39-8.40 (d, 1H); 9.08-9.09 (m, 1H); 12.0 (br. s, 1H) ppm.

The following compounds were obtained in an analogous manner:

(a) 5-Ethyl-2-(pyridin-3-yl)-2,4-dihydro-3H-1,2,4-triazol-3-one

HPLC-MS: log P=0.30; mass (m/z) 191.1 (M+H)$^+$ $^1$H-NMR (d$_6$-DMSO) 1.19-1.23 (t, 3H); 2.52-2.58 (q, 2H); 7.45-7.48 (m, 1H); 8.20-8.23 (m, 1H); 8.40 (br. s, 1H); 9.10 (br. s); 12.0 (br. s, 1H) ppm.

(b) 5-Isopropyl-2-(pyridin-3-yl)-2,4-dihydro-3H-1,2,4-triazol-3-one

HPLC-MS: log P=0.71; mass (m/z) 205.1 (M+H)$^+$ $^1$H-NMR (d$_6$-DMSO) 1.18-1.28 (d, 6H); 2.82-2.89 (m, 1H); 7.45-7.49 (m, 1H); 8.20-8.23 (m, 1H); 8.39-8.41 (m, 1H); 9.10-9.11 (br. s, 1H); 12.0 (br. s, 1H) ppm.

For 20 min, a weak stream of argon was passed through a mixture of 278 mg (1.359 mmol) of 5-isopropyl-2-(pyridin-3-yl)-2,4-dihydro-3H-1,2,4-triazol-3-one (cf. step 1), 401 mg (1.699 mmol) of 2-(6-bromopyridin-2-yl)pyrimidine and 293 mg (2.12 mmol) of powdered potassium carbonate in 3.2 ml of N,N-dimethylformamide. 58.7 mg (0.286 mmol) of copper (I) iodide were then added, and under protective gas the reaction mixture was heated at 150° C. for 2 hours. Analytically, by thin-layer chromatography, both starting materials were still detectable. A further 120 mg (0.585 mmol) of copper(I) iodide were added, and the mixture was heated at 150° C. for 16 hours. The cooled reaction mixture was then concentrated under reduced pressure, taken up in 30 ml of ethyl acetate and titrated with 0.5 ml of 25% strength ammonia solution and 2 ml of water. The water was bound by addition of sodium sulfate. Filtration and concentration gave 247 mg of a brown viscous oil which was pre-purified by chromatography on a Combiflash system (Redisept column, silica 4 g; mobile phase: dichloromethane/methanol). Re-purification by HPLC gave 30 mg of 5-isopropyl-2-(pyridin-3-yl)-4-[6-(pyrimidin-2-yl)pyridin-2-yl]-2,4-dihydro-3H-1,2,4-triazol-3-one (content LC-MS: 96%).

HPLC-MS: log P=1.77; mass (m/z) 360.1 (M+H)$^+$ $^1$H-NMR (d$_6$-DMSO) 2.50-2.52 (t, 6H); 3.43-3.47 (m, 1H); 7.56-7.58 (dd, 1H); 7.61-7.63 (t, 1H); 7.94-7.95 (d, 1H); 8.29-8.33 (m, 2H); 8.49-8.50 (m, 1H); 8.54-8.56 (d, 1H); 9.03 (br. s, 2H); 9.19 (br. s, 1H) ppm.

The Following Compounds were Obtained in an Analogous Manner:

(a) 5-Ethyl-2-(pyridin-3-yl)-4-[6-(pyrimidin-2-yl)pyridin-2-yl]-2,4-dihydro-3H-1,2,4-triazol-3-one (cf. Table 1, Example 15) and (b) 5-methyl-2-(pyridin-3-yl)-4-[6-(pyrimidin-2-yl)pyridin-2-yl]-2,4-dihydro-3H-1,2,4-triazol-3-one (cf. Table 1, Example 16)

Example K

2-{6-[5-(Pyridin-3-yl)-1,3-thiazol-2-yl]pyridin-2-yl}pyrimidine

Step 1:
2-[6-(1,3-Thiazol-2-yl)pyridin-2-yl]pyrimidine

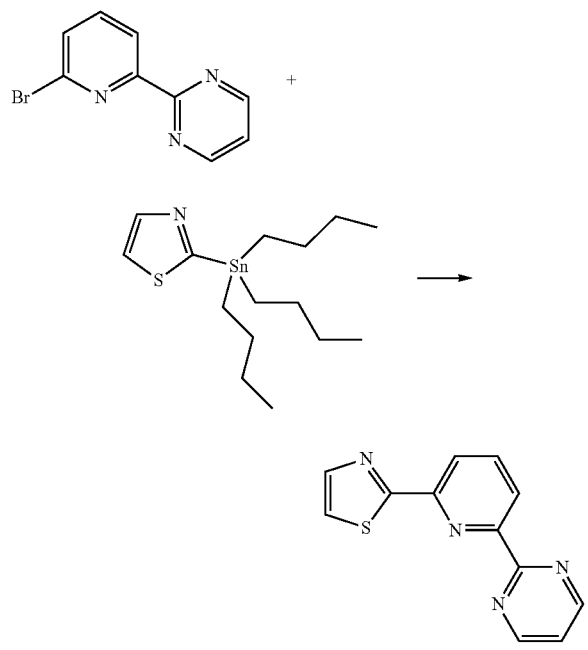

Under argon, 2.69 g (7.18 mmol) of 2-tributylstannylthiazole, 1.69 g (7.18 mmol) of 2-bromo-6-pyrimidylpyridine and 0.49 g (0.43 mmol) of tetrakis(triphenylphosphine)palladium were stirred in 100 ml of toluene at 100° C. for 16 hours. For work-up, the solvent was removed under reduced pressure, the crude product was dissolved in dichloromethane and stirred with saturated potassium fluoride solution for 16 hours, the mixture was filtered through Celite and the organic phase was concentrated. Further purification by column chromatography on silica gel (mobile phase: cyclohexane/ethyl acetate). This gave 0.93 g (54% of theory) of 2-[6-(1,3-thiazol-2-yl)pyridin-2-yl]pyrimidine which was used for subsequent reactions.

HPLC-MS: log P=1.43; mass (m/z) 241.1 (M+H)+

$^1$H-NMR (DMSO): 7.92 (m, 1H), 8.05 (m, 1H), 8.18 (m, 2H), 8.39 (m, 1H), 8.45 (m, 1H), 9.08 (m, 2H) ppm.

Step 2: 2-{6-[5-(Pyridin-3-yl)-1,3-thiazol-2-yl]pyridin-2-yl}pyrimidine

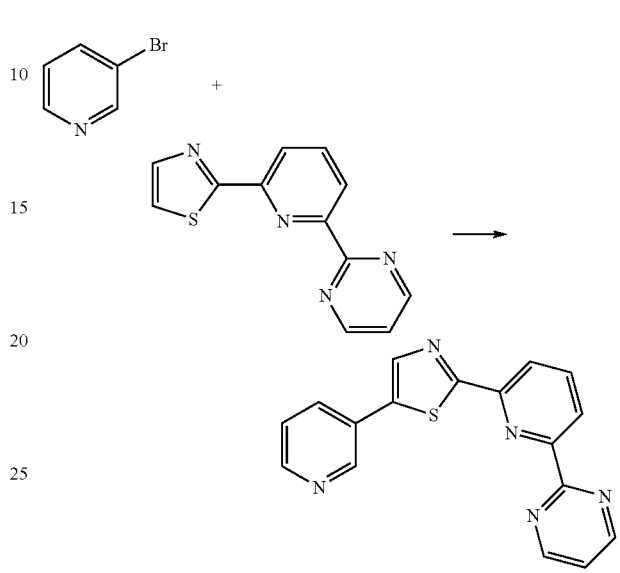

Under argon, 79 mg (0.50 mmol) of 3-bromopyridine, 120 mg (0.50 mmol) of 2-[6-(1,3-thiazol-2-yl)pyridin-2-yl]pyrimidine (cf. step 1), 326 mg (1.0 mmol) of cesium carbonate and 8 mg (0.01 mmol) of [(t-Bu)$_2$P(OH)]$_2$PdCl$_2$ ("POPd") in 10 ml of N,N-dimethylformamide were stirred at 120° C. for 16 hours. For work-up, the solvent was removed under reduced pressure, the residue was partitioned between ethyl acetate and water and the organic phase was dried, concentrated under reduced pressure and purified by column chromatography on silica gel RP-18 (mobile phase: water/acetonitrile/formic acid). This gave 28 mg (18% of theory) of 2-{6-[5-(pyridin-3-yl)-1,3-thiazol-2-yl]pyridin-2-yl}pyrimidine.

HPLC-MS: log P=1.79; mass (m/z) 318.0 (M+H)+

$^1$H-NMR (DMSO): 7.51 (m, 1H), 7.63 (m, 1H), 8.20 (m, 3H), 8.48 (m, 1H), 8.58 (m, 2H), 9.05 (m, 3H) ppm.

Example L

2-{6-[5-(5-Fluoropyridin-3-yl)-1,3-thiazol-2-yl]pyridin-2-yl}pyrimidine

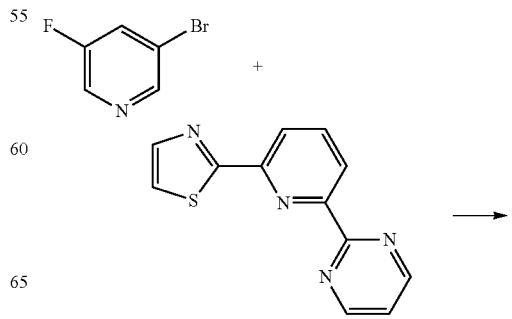

-continued

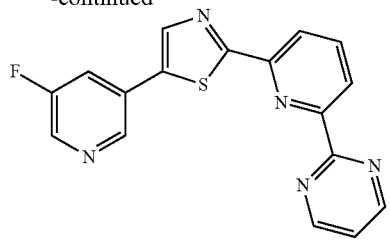

Under argon, 88 mg (0.50 mmol) of 3-bromo-5-fluoropyridine, 120 mg (0.50 mmol) of 2-[6-(1,3-thiazol-2-yl)pyridin-2-yl]pyrimidine (cf. Example K, step 1), 326 mg (1.0 mmol) of cesium carbonate and 8 mg (0.01 mmol) of [(t-Bu)$_2$P(OH)]$_2$PdCl$_2$ ("POPd") in 10 ml of N,N-dimethylformamide were stirred at 120° C. for 16 hours. For work-up, the solvent was removed under reduced pressure, the residue was partitioned between ethyl acetate and water and the organic phase was dried, concentrated under reduced pressure and purified by column chromatography on silica gel RP-18 (mobile phase: water/acetonitrile/formic acid). This gave 11 mg (7% of theory) of 2-{6-[5-(5-fluoropyridin-3-yl)-1,3-thiazol-2-yl]pyridin-2-yl}pyrimidine.

HPLC-MS: log P=2.13; mass (m/z) 336.0 (M+H)$^+$ $^1$H-NMR (DMSO): 7.63 (m, 1H), 8.20 (m, 1H), 8.29 (m, 2H), 8.49 (m, 1H), 8.62 (m, 2H), 8.93 (m, 1H), 9.06 (m, 2H) ppm.

Example M

6-[3-(5-Fluoro-3-pyridinyl)-1H-pyrazol-1-yl]-N-[(dimethylamino)sulfonyl]-2-pyridinecarboxamide Step 1: (E/Z)-3-(Dimethylamino)-1-(5-fluoro-3-pyridinyl)-2-propen-1-one

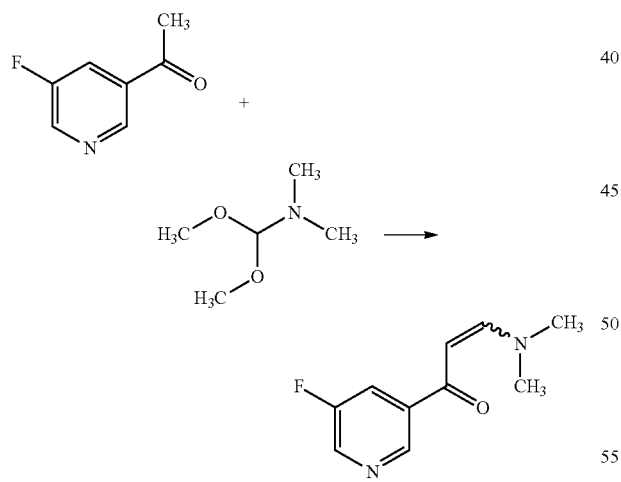

5.00 g (35.9 mmol) of 1-(5-Fluoro-3-pyridinyl)ethanone and 4.70 g (35.9 mmol) of N,N-dimethylformamide dimethyl acetal were initially charged in 40 ml of DMF and stirred at 130° C. for 4 hours. Excess solvent was then removed under reduced pressure and the reside that remained was titrated with methyl-tert-butyl ether. This gave 5.52 g (79% of theory) of (E/Z)-3-(dimethylamino)-1-(5-fluoro-3-pyridinyl)-2-propen-1-one which was used without further purification for the cyclization reaction.

HPLC-MS: log P=0.91; mass (m/z) 195.1 (M+H)$^+$

Step 2: 3-(5-Fluoro-3-pyridinyl)-1H-pyrazole

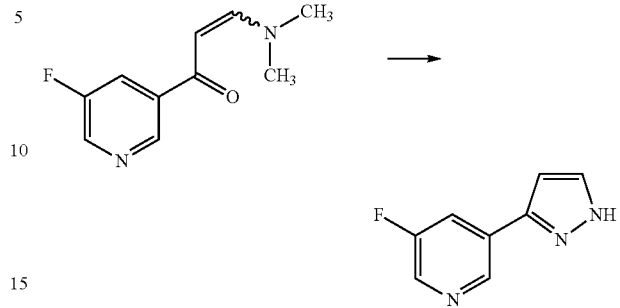

5.52 g (28.4 mmol) of (E/Z)-3-(Dimethylamino)-1-(5-fluoro-3-pyridinyl)-2-propen-1-one (preparation cf. step 1) were stirred in 50 ml of methanol. 1.42 g (28.4 mmol) of hydrazine hydrate were then added dropwise, and the reaction mixture was stirred at room temperature for 48 hours. Concentration under reduced pressure gave 4.60 g (99% of theory) of 3-(5-fluoro-3-pyridinyl)-1H-pyrazole which was used without further purification for the next reaction.

HPLC-MS: log P=0.92; mass (m/z) 164.2 (M+H)$^+$

Step 3: Methyl 6-[3-(5-fluoro-3-pyridinyl)-1H-pyrazol-1-yl]-2-pyridinecarboxylate

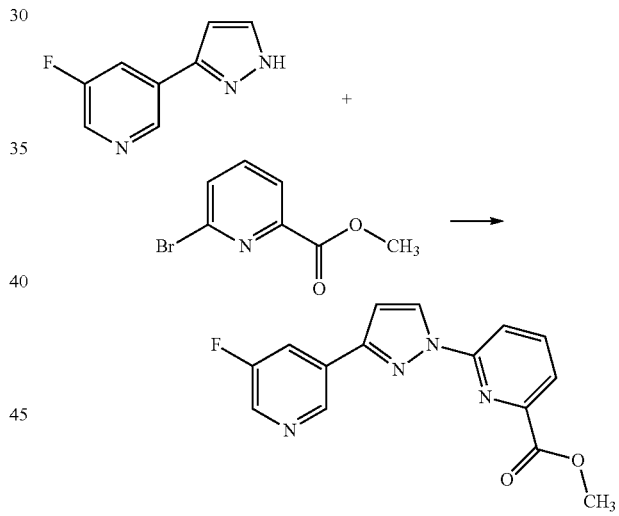

30 ml of DMF were added to 1.88 g (11.5 mmol) of 3-(5-fluoro-3-pyridinyl)-1H-pyrazole (preparation cf. step 2), 2.50 g (11.5 mmol) of methyl 6-bromo-2-pyridinecarboxylate, 92.0 mg (1.15 mmol) of copper (II) oxide, 7.54 g (23.10 mmol) of cesium carbonate and 1.22 g (3.47 mmol) of iron (III) acetylacetonate, and the mixture was stirred at 90° C. for 60 hours. The entire reaction mixture was then cooled to room temperature, and water was added. The reaction mixture was then extracted with ethyl acetate. The organic phase was separated off, dried, filtered and concentrated under reduced pressure. The residue was purified by chromatography on silica gel. This gave 191 mg (5.0% of theory) of methyl 6-[3-(5-fluoro-3-pyridinyl)-1H-pyrazol-1-yl]-2-pyridinecarboxylate.

HPLC-MS: log P=1.07; mass (m/z) 299.0 (M+H)$^+$ $^1$H-NMR (CD$_3$CN) 3.96 (s, 3H), 7.03 (d, 1H), 8.01-8.13 (m, 3H), 8.29 (dd, 1H), 8.48 (d, 1H), 8.67 (d, 1H), 9.01 (dd, 1H) ppm.

Step 4: 6-[3-(5-Fluoro-3-pyridinyl)-1H-pyrazol-1-yl]-2-pyridinecarboxylate

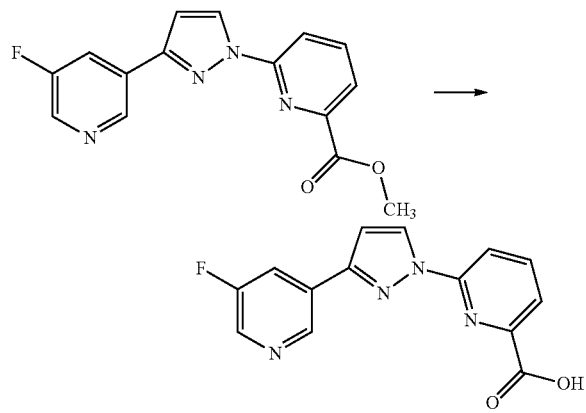

180 mg (0.60 mmol) of methyl 6-[3-(5-fluoro-3-pyridinyl)-1H-pyrazol-1-yl]-2-pyridinecarboxylate (preparation cf. step 3) were initially charged in 3.3 ml of dioxane, and 0.33 ml of water and 178 mg (4.46 mmol) of a 45% strength sodium hydroxide solution were added with stirring. The entire reaction mixture was then heated at reflux temperature for 5 hours. For work-up, the reaction mixture was cooled to room temperature and the dioxane was distilled off under reduced pressure. A little cold water was then added to the residue that remained, and the pH was adjusted to 3 using concentrated hydrochloric acid. The resulting precipitate was separated off and dried. This gave 121 mg (66.8% of theory) of 6-[3-(5-fluoro-3-pyridinyl)-1H-pyrazol-1-yl]-2-pyridinecarboxylate, which can be used for subsequent reactions.

HPLC-MS: log P=1.81; mass (m/z) 285.1 (M+H)$^+$

Step 5: 6-[3-(5-Fluoro-3-pyridinyl)-1H-pyrazol-1-yl]-N-[(dimethylamino)sulfonyl]-2-pyridinecarboxamide

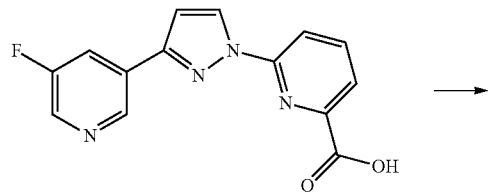

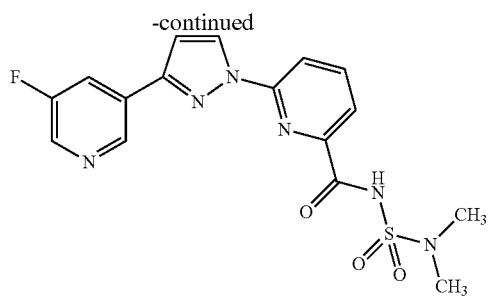

110 mg (0.38 mmol) of 6-[3-(5-fluoro-3-pyridinyl)-1H-pyrazol-1-yl]-2-pyridinecarboxylic acid (preparation cf. step 4) were initially charged in 10 ml of tetrahydrofuran (THF), and 94.1 mg (0.58 mmol) of N,N-carbonylimidazole were added with stirring. The reaction mixture was then heated at reflux temperature for one hour. After cooling of the reaction solution, 72.0 mg (0.58 mmol) of N,N-dimethylsulfonamide, dissolved in 6 ml of THF, were added dropwise and the mixture was stirred at room temperature for 10 minutes. After the addition of 1,8-diazabicyclo(5.4.0)-undec-7-ene, the reaction mixture was stirred at room temperature for a further 12 hours. For work-up, the entire reaction mixture was concentrated under reduced pressure, and water was added to the residue that remained. The aqueous phase was extracted with methylene chloride. The organic phase were discarded and the aqueous phase was acidified with concentrated hydrochloric acid and once more extracted with methylene chloride. The organic phase was separated off and dried and then concentrated under reduced pressure, and the residue that remained was purified by chromatography on silica gel (mobile phase: cyclohexane/acetone). This gave 36 g (23.8% of theory) of 6-[3-(5-fluoro-3-pyridinyl)-1H-pyrazol-1-yl]-N-[(dimethyl-amino)sulfonyl]-2-pyridinecarboxamide.

HPLC-MS: log P=2.61; mass (m/z) 391.1 (M+H)$^+$ $^{13}$C- with $^1$H-NMR decoupling (CPD) (CD$_3$CN) 38.8 (2× CH$_3$), 117.7, 122.1, 142.2, 147.7 (2-pyridinyl), 120.5, 131.1, 138.5, 144.3, 160.3 (5-F-pyrinin-3-yl), 107.3, 131.1, 151.2 (1H-pyrazol-1-yl), 163.2 (C=O) ppm.

According to the NMR spectra, the compound is present as a mixture with a dimethylammonium salt; cf. $^{13}$C-NMR (CD$_3$CN) 38.6 (2×CH$_3$) ppm, $^1$H-NMR (CD$_3$CN) 2.57 (s, 2×CH$_3$), 5.05 (br., NH) ppm.

TABLE 1

Compounds of the formula (I)

(I)

$$G^1 \diagdown \text{—} Q$$
$$A^2 \diagdown N$$

in which A$^2$ represents hydrogen and G$^1$ represents CH

| Compound No. | Q | logP$^a$ | NMR Data$^b$ |
|---|---|---|---|
| 1 (Example A) | 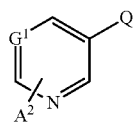 | 2.23 | 7.58-7.61 (m, 1H), 7.82-7.84 (m, 1H), 7.90 (s, 1H), 7.99-8.02 (m, 1H), 8.06-8.08 (m, 1H), 8.38-8.41 (m, 1H), 8.73-8.74 (m, 1H), 9.20-9.21 (m, 1H). |

TABLE 1-continued
Compounds of the formula (I)
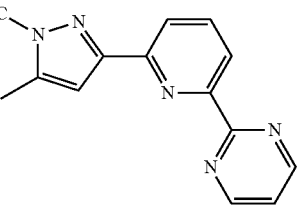
(I)
in which A² represents hydrogen and G¹ represents CH
| Compound No. | Q | logP$^a$ | NMR Data$^b$ |
|---|---|---|---|
| 2 (Example B) | 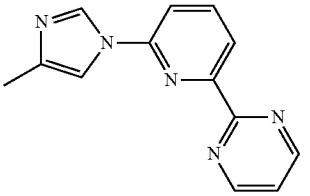 | 1.26 | 4.00 (s, 3H), 7.14 (s, 1H), 7.57-7.60 (m, 2H), 8.03-8.06 (m, 1H), 8.10-8.14 (m, 2H), 8.30-8.32 (m, 1H), 8.67-8.69 (m, 1H), 8.88-8.89 (m, 1H), 9.01-9.02 (m, 2H). |
| 3 (Example C) | 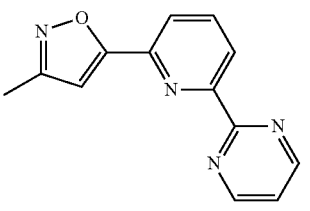 | 0.73 | 7.44-7.47 (m, 1H), 7.62-7.64 (m, 1H), 8.02-8.04 (m, 1H), 8.24-8.28 (m, 2H), 8.39-8.41 (m, 1H), 8.48-8.49 (m, 1H), 8.66-8.67 (m, 1H), 8.73-8.74 (m, 1H), 9.05-9.06 (m, 2H), 9.12-9.13 (m, 1H). |
| 4 | 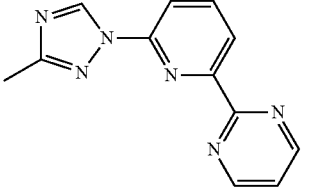 | 1.50 | 7.60-7.65 (m, 2H), 7.86 (s, 1H), 8.17-8.26 (m, 2H), 8.41-8.44 (m, 1H), 8.50-8.52 (m, 1H), 8.73-8.75 (m, 1H), 9.05-9.06 (m, 2H), 9.22-9.23 (m, 1H). |
| 5 | 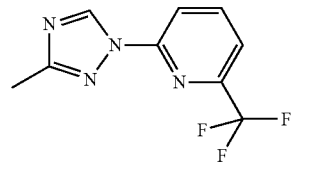 | 1.23 | 7.60 (dd, 1H), 7.65 (t, 1H), 8.15 (d, 1H), 8.32 (t, 1H), 8.49 (m, 2H), 8.71 (dd, 1H), 9.06 (d, 2H), 9.33 (d, 1H), 9.49 (s, 1H). |
| 6 (Example D) | 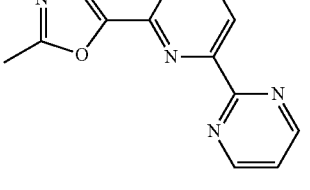 | 2.11 | 7.59 (ddd, 1H), 8.02 (d, 1H), 8.29 (d, 1H), 8.42 (t, 1H), 8.47 (dt, 1H), 8.72 (dd, 1H), 9.32 (dd, 1H). |
| 7 (Example E) |  | 1.39 | 7.62 (m, 2H), 8.08 (m, 1H), 8.15 (m, 2H), 8.39 (m, 1H), 8.50 (m, 1H), 8.79 (m, 1H), 9.04 (m, 2H), 9.32 (m, 1H). |

TABLE 1-continued

Compounds of the formula (I)

(I)

in which A² represents hydrogen and G¹ represents CH

| Compound No. | Q | logP$^a$ | NMR Data$^b$ |
|---|---|---|---|
| 8 | (structure: 2-methyl-oxazol-5-yl pyridine with 1,3-dioxane) | 1.62 | 2.05 (m, 2H), 4.04 (m, 2H), 4.18 (m, 2H), 5.60 (s, 1H), 7.60 (m, 2H), 8.0 (m, 3H), 8.45 (m, 1H), 8.75 (m, 1H), 9.30 ppm (m, 1H). |
| 9 (Example F) | (structure: 4-methylpyrazol-1-yl pyridine with pyrimidine) | 1.04 | 7.45 (m, 1H), 7.6 (m, 1H), 8.1-8.2 (m, 3H), 8.35 (m, 2H), 8.5 (m, 1H), 9.05 (m, 3H), 9.15 (s, 1H). |
| 10 (Example G) | (structure: 1-methyl-triazol-4-yl pyridine with pyrimidine) | 1.39 | 7.61 (t, 1H), 7.69 (dd, 1H), 8.16 (t, 1H), 8.29 (d, 1H), 8.38 (d, 1H), 8.51 (m, 1H), 8.73 (dd, 1H), 9.03 (d, 2H), 9.31 (d, 1H), 9.44 (s, 1H). |
| 11 (Example H) | (structure: furan-3-yl pyridine with pyrimidine) | 1.26 | 7.51 (ddd, 1H), 7.61 (t, 1H), 7.77 (s, 1H), 7.94 (dd, 1H), 8.06 (t, 1H), 8.19 (m, 1H), 8.28 (dd, 1H), 8.55 (dd, 1H), 8.57 (d, 1H), 9.03 (s, 1H), 9.04 (s, 1H), 9.05 (dd, 1H). |
| 12 | (structure: furan-3-yl pyridine with 1,3-dioxane) | 1.57 | 1.49 (dt, 1H), 2.05 (m, 1H), 3.99 (dt, 2H), 4.17 (m, 2H), 5.54 (s, 1H), 7.43 (dd, 1H), 7.49 (ddd, 1H), 7.68 (d, 1H), 7.76 (dd, 1H), 7.90 (t, 1H), 8.15 (dt, 1H), 8.47 (d, 1H), 8.53 (dd, 1H), 9.02 ppm (d, 1H). |
| 13 (Example I) | (structure: pyrazol-1-yl pyridine with pyrimidine) | 1.20 | 7.02 (d, 1H), 7.43-7.48 (m, 1H), 8.13 (t, 1H), 8.22 (dd, 2H), 8.28-8.31 (2t, 2H), 8.40 (dd, 1H), 8.79 (d, 1H), 8.95 (d, 2H), 9.18 (d, 2H).$^c$ |

TABLE 1-continued

Compounds of the formula (I)

in which A² represents hydrogen and G¹ represents CH

| Compound No. | Q | logP[a] | NMR Data[b] |
|---|---|---|---|
| 14 (Example J) | (structure) | 1.77 | 2.50-2.52 (t, 6H); 3.43-3.47 (m, 1H); 7.56-7.58 (dd, 1H); 7.61-7.63 (t, 1H); 7.94-7.95 (d, 1H); 8.29-8.33 (m, 2H); 8.49-8.50 (m, 1H); 8.54-8.56 (d, 1H); 9.03 (br. s, 2H); 9.19 (br. s, 1H). |
| 15 | (structure) | 1.48 | 1.18-1.23 (t, 3H); 2.94-2.98 (q, 2H); 7.56-7.58 (m, 1H); 7.61-7.63 (m, 1H); 8.29-8.32 (m, 2H); 8.49-8.54 (m, 1H); 9.03 (br. s, 1H); 9.19 (br. s, 1H). |
| 16 | (structure) | 1.17 | 2.56 (s, 3H); 7.54-7.58 (dd, 1H); 7.60-7.63 (t, 1H); 7.96-7.98 (d, 1H); 8.27-8.32 (m, 2H); 8.48-8.52 (m, 1H); 9.03-9.04 (m, 1H); 9.17-9.18 (m, 1H). |
| 17 (Example K) | (structure) | 1.79 | 7.51 (m, 1H), 7.63 (m, 1H), 8.20 (m, 3H), 8.48 (m, 1H), 8.58 (m, 2H), 9.05 (m, 3H). |
| 18 | (structure) | 0.72 | 1.48-1.52 (m, 1H), 2.05-2.09 (m, 1H); 3.97-4.04 (m, 2H), 4.16-4.21 (m, 2H), 5.56 (s, 1H), 7.48-7.55 (m, 2H), 7.85-7.88 (m, 1H), 8.08-8.13 (m, 1H), 8.18-8.22 (m, 1H), 8.59 (s, 1H), 8.63-8.64 (m, 1H), 8.68-8.71 (m, 1H), 9.02-9.03 (m, 1H). |

TABLE 1-continued

Compounds of the formula (I)

in which A² represents hydrogen and G¹ represents CH

| Compound No. | Q | logP[a] | NMR Data[b] |
|---|---|---|---|
| 19 | (pyrazolyl-pyridine-CF₃ structure) | 1.33 | 7.43-7.47 (m, 1H), 7.92 (d, 1H), 8.20 (d, 1H), 8.24-8.27 (m, 1H), 8.36 (t, 1H), 8.48-8.50 (m, 1H), 8.63-8.64 (m, 1H), 8.68-8.70 (m, 1H), 9.02-9.03 (m, 1H). |

[a] HCOOH,
[b] ¹H-NMR (DMSO-d₆) in ppm,
[c] ¹H-NMR (CD₃CN) in ppm
[d] The arrow marks the bond to the adjacent ring.

TABLE 2

Compounds of the formula (I)

in which A² represents hydrogen and G¹ represents CF

| Compound No. | Q | logP[a] | NMR Data[b] |
|---|---|---|---|
| 20 | (pyrazolyl-pyridine-pyrimidine structure) | 2.21 | |
| 21 (Example L) | (thiazolyl-pyridine-pyrimidine structure) | 2.13 | 7.63 (m, 1H), 8.20 (m, 1H), 8.29 (m, 2H), 8.49 (m, 1H), 8.62 (m, 2H), 8.93 (m, 1H), 9.06 (m, 2H). |
| 22 (Example M) | 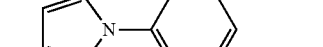 | 2.61 | 2.99 (s, 6H), 7.05 (d, 1H), 8.09-8.10 (br, 2H), 8.18 (t, 1H), 8.38 (dd, 1H), 8.49 (d, 1H), 9.93 (d, 1H), 9.01 (br, 1H), 10.1 (br., 1H).[c] |

TABLE 2-continued

Compounds of the formula (I)

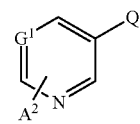

(I)

in which $A^2$ represents hydrogen and $G^1$ represents CF

| Compound No. | Q | logP[a] | NMR Data[b] |
|---|---|---|---|
| 23 | 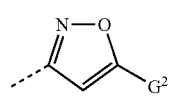 | 2.38 | 7.07 (d, 1H), 7.74 (dd, 1H), 8.02-8.06 (2m, 1H), 8.50 (m, 1H), 8.74 (m, 2H), 8.98 (t, 1H), 9.11 (dd, 1H).[c] |

[a]HCOOH,
[b]1H-NMR (DMSO-d6) in ppm,
[c]1H-NMR (CD3CN) in ppm
[d]The arrow marks the bond to the adjacent ring.

Myzus Test (Spray Treatment)

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Discs of Chinese cabbage (Brassica pekinensis) infected by all stages of the green peach aphid (*Myzus persicae*) are sprayed with an active compound preparation of the desired concentration.

After 6 days, the effect in % is determined. 100% means that all of the aphids have been killed; 0% means that none of the aphids have been killed.

In this test, for example, the following compounds of the Preparation Examples show, at an application rate of 500 g/ha, an effect of 100%: 1, 2, 3, 4, 6, 7, 8, 9, 10, 17, 18, 19

In this test, for example, the following compounds of the Preparation Examples show, at an application rate of 500 g/ha, an effect of 90%: 12, 20, 21

Tetranychus Test (OP-Resistant/Spray Treatment)

Solvents: 78.0 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration. Discs of bean leaves (*Phaseolus vulgaris*) which are infested by all stages of the greenhouse red spider mite (*Tetranychus urticae*) are sprayed with an active compound preparation of the desired concentration.

After 6 days, the effect in % is determined. 100% means that all of the spider mites have been killed; 0% means that none of the spider mites have been killed.

In this test, for example, the following compound of the Preparation Examples shows, at an application rate of 500 g/ha, an effect of 100%: 7

3. A compound according to claim 1 wherein
G¹ represents CH,
A² represents hydrogen, and Q represents
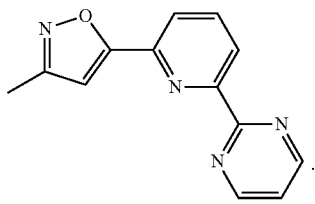 [SMILES: Cc1cc(-c2cccc(-c3ncccn3)n2)on1]

The invention claimed is:
1. A compound of the formula (I)

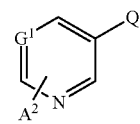

(I)

or a salt, tautomeric and/or isomeric form, or N-oxide thereof,
wherein
$G^1$ represents $C-A^1$,
$A^1$ represents hydrogen,
$A^2$ represents hydrogen, and
Q represents

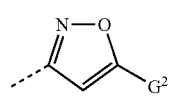

(Q-16)

in which
$G^2$ represents

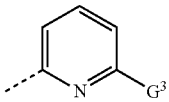

(G²-19)

where the broken line marks the bond to the heterocycle, and
$G^3$ represents pyrimidyl, which is optionally substituted by halogen, nitro, alkyl, haloalkyl, alkoxy, haloalkoxy, alkoxyalkyl, alkylthio, alkylthioalkyl or cycloalkyl.

2. A method for controlling pests selected from the order of the Homoptera and the order of the Thysanoptera, wherein a pesticidal effective amount of a compound of the formula (I) according to claim 1 is allowed to act on the pests and/or their habitat.